(12) United States Patent
Zwingenberger et al.

(10) Patent No.: US 10,004,820 B2
(45) Date of Patent: Jun. 26, 2018

(54) CONTAINER FOR WASHING STERILIZATION, TRANSPORTATION AND STERILE STORAGE OF ARTICLES

(71) Applicant: SciCan Ltd., Toronto (CA)

(72) Inventors: Arthur Zwingenberger, Lucerne (CH); Robert Biermann, Blackstock (CA); Andy Kwan-Leung Sun, Toronto (CA)

(73) Assignee: SciCan Ltd., Toronto, Ontario (CA)

( * ) Notice: Subject to any disclaimer, the term of this patent is extended or adjusted under 35 U.S.C. 154(b) by 414 days.

(21) Appl. No.: 14/419,490

(22) PCT Filed: Aug. 7, 2013

(86) PCT No.: PCT/CA2013/050605
§ 371 (c)(1),
(2) Date: Feb. 4, 2015

(87) PCT Pub. No.: WO2014/022933
PCT Pub. Date: Feb. 13, 2014

(65) Prior Publication Data
US 2015/0217008 A1  Aug. 6, 2015

Related U.S. Application Data

(60) Provisional application No. 61/680,482, filed on Aug. 7, 2012.

(51) Int. Cl.
*A61L 2/07* (2006.01)
*A61L 2/16* (2006.01)
(Continued)

(52) U.S. Cl.
CPC ............... *A61L 2/07* (2013.01); *A61B 50/00* (2016.02); *A61B 50/20* (2016.02); *A61B 50/22* (2016.02);
(Continued)

(58) Field of Classification Search
CPC ..... A61L 2/07; A61L 2/26; A61L 2/16; A61B 50/30; A61B 50/34; A61B 50/20; A61B 50/22; A61B 50/33; A61B 50/00
See application file for complete search history.

(56) References Cited

U.S. PATENT DOCUMENTS 4,113,098 A  9/1978  Howard
4,126,224 A  11/1978  Laauwe et al.
(Continued)

FOREIGN PATENT DOCUMENTS

CA  2 133464  10/1993
DE  202 13 523  11/2002
(Continued)

OTHER PUBLICATIONS

StenlContainer S™ Mini Size Container, AESCULAP® Brochure, 2 pages, 2010.
(Continued)

*Primary Examiner* — Regina M Yoo
(74) *Attorney, Agent, or Firm* — Clark & Brody

(57) ABSTRACT

A container for washing, sterilization, transportation and sterile storage of articles for sterilization is provided. The container includes a sleeve and a frame adapted to receive articles for sterilization. The container includes at least one filtered opening to permit communication between the sterilization apparatus and the sterilization chamber for the communication of steam and air. In a first configuration, a front and rear wall of the frame engage the sleeve to create a sterilization chamber. The container may be stacked and stored in any orientation. In a second configuration, the frame rests or nests on top of the sleeve to permit access to and use of the sterilized articles. The container, may include one or a plurality of openings for communication between a (Continued)

sterilization apparatus and the sterilization chamber and one or more filters adjacent to the pluralities of openings.

31 Claims, 54 Drawing Sheets

(51) Int. Cl.
*A61L 2/26* (2006.01)
*A61B 50/00* (2016.01)
*A61B 50/20* (2016.01)
*A61B 50/22* (2016.01)
*A61B 50/30* (2016.01)
*A61B 50/33* (2016.01)
*A61B 50/34* (2016.01)

(52) U.S. Cl.
CPC .............. *A61B 50/30* (2016.02); *A61B 50/33* (2016.02); *A61B 50/34* (2016.02); *A61L 2/16* (2013.01); *A61L 2/26* (2013.01); *A61B 2050/006* (2016.02); *A61L 2202/182* (2013.01)

(56) References Cited

U.S. PATENT DOCUMENTS

| | | | |
|---|---|---|---|
| 4,296,852 A | 10/1981 | Amantrout et al. | |
| 4,541,992 A | 9/1985 | Jerge et al. | |
| 4,551,311 A | 11/1985 | Lorenz | |
| 4,583,643 A | 4/1986 | Sanderson | |
| 4,754,595 A * | 7/1988 | Sanderson | A61L 2/26 53/425 |
| 4,900,519 A | 2/1990 | Nichols | |
| 4,915,913 A * | 4/1990 | Williams | A61L 2/26 220/324 |
| 4,959,199 A | 9/1990 | Brewer | |
| 5,080,874 A | 1/1992 | Nichols | |
| 5,178,278 A | 1/1993 | Oliverius | |
| 5,279,800 A * | 1/1994 | Berry, Jr. | A61L 2/26 206/363 |
| 5,340,551 A | 8/1994 | Barry, Jr. | |
| 5,346,677 A | 9/1994 | Rlsk | |
| 5,372,787 A | 12/1994 | Ritter | |
| 5,384,103 A | 1/1995 | Miller | |
| 5,424,048 A | 6/1995 | Riley | |
| 5,433,929 A | 7/1995 | Riihimaki et al. | |
| 5,451,379 A | 9/1995 | Bowlin, Jr. | |
| 5,451,380 A * | 9/1995 | Zinnanti | A61L 2/26 206/370 |
| 6,164,738 A | 12/2000 | Dane et al. | |
| 6,217,835 B1 | 4/2001 | Riley et al. | |
| 6,247,609 B1 | 6/2001 | Gabele et al. | |
| 6,368,565 B1 | 4/2002 | Michaelson et al. | |
| 6,379,631 B1 | 4/2002 | Wu | |
| 6,450,328 B1 * | 9/2002 | Machacek | A61C 19/02 206/45.2 |
| 6,534,000 B1 | 3/2003 | Michaelson et al. | |
| 6,759,017 B2 | 7/2004 | Wu et al. | |
| 6,874,634 B2 | 4/2005 | Riley | |
| 6,896,149 B1 | 5/2005 | Berry, III | |
| 7,021,485 B1 | 4/2006 | Baker et al. | |
| 7,247,183 B2 | 7/2007 | Connor et al. | |
| 7,544,336 B2 | 6/2009 | Powell | |
| 7,757,843 B2 * | 7/2010 | Katsis | A24F 27/00 206/1.5 |
| 7,914,751 B2 | 3/2011 | Oertmann | |
| 2005/0263422 A1 * | 12/2005 | Kohler | A61L 2/186 206/459.1 |
| 2006/0064956 A1 | 3/2006 | Connor et al. | |
| 2007/0062830 A1 | 3/2007 | Oertmann | |
| 2010/0065456 A1 * | 3/2010 | Junk | A61L 2/26 206/363 |
| 2011/0266280 A1 | 11/2011 | Thomas et al. | |
| 2012/0057810 A1 * | 3/2012 | De Klerk | A61L 2/26 383/41 |
| 2012/0195792 A1 | 8/2012 | Duddy et al. | |

FOREIGN PATENT DOCUMENTS

| | | |
|---|---|---|
| EP | 1 122 510 | 8/2001 |
| EP | 1735015 | 12/2006 |
| EP | 2 163 219 | 3/2010 |
| JP | 2001-289629 | 10/2001 |
| JP | 2002-272821 | 9/2002 |
| JP | 2010-063889 | 3/2010 |
| WO | 1992/07588 | 5/1992 |
| WO | 1997/30737 | 8/1997 |
| WO | 2005/102849 | 11/2005 |
| WO | 2008/003177 | 1/2008 |
| WO | 2010/042847 | 4/2010 |
| WO | 2010/066035 | 6/2010 |
| WO | 2012/106506 | 8/2012 |
| WO | 2013/060667 | 5/2013 |

OTHER PUBLICATIONS

Aesculap Sterile Technologies—PrimeLine, AESCULAP® Brochure, 2 pages, 2006.
Aesculap Sterile Technologies—SterilContainer System, General Catalog, AESCULAR®, 84 pages, 2009.
Aesculap Sterile Technology—SterilContainer™ System Overview, AESCULAP®, 8 pages, 2009.
Sterile Container System—Barrier Model, BAHADIR® Brochure, 12 pages, Aug. 6, 2012.
MicroStop® Mini-Set Sterile Containers, KLS Martin Group Brochure, 12 pages, Aug. 6, 2012.
Sterilization Containers and SPD Supplies, Catalog, Miltex, 28 pages, Aug. 6, 2012.
Polysterbox®, Ritter Medical Supply Brochure, 2 pages, Aug. 6, 2012.
Sterilization Container System from STERIS, STERIS® Brochure, 6 pages, Aug. 2007.
Stenset® & TASKIT® Sterilization Containers, MEDLINE Brochure, 12 pages, 2005.
Aesculap Sterile Technology—PrimeLine Clear Lid, AESCULAP® Brochure, 4 pages, Aug. 8, 2012.

* cited by examiner

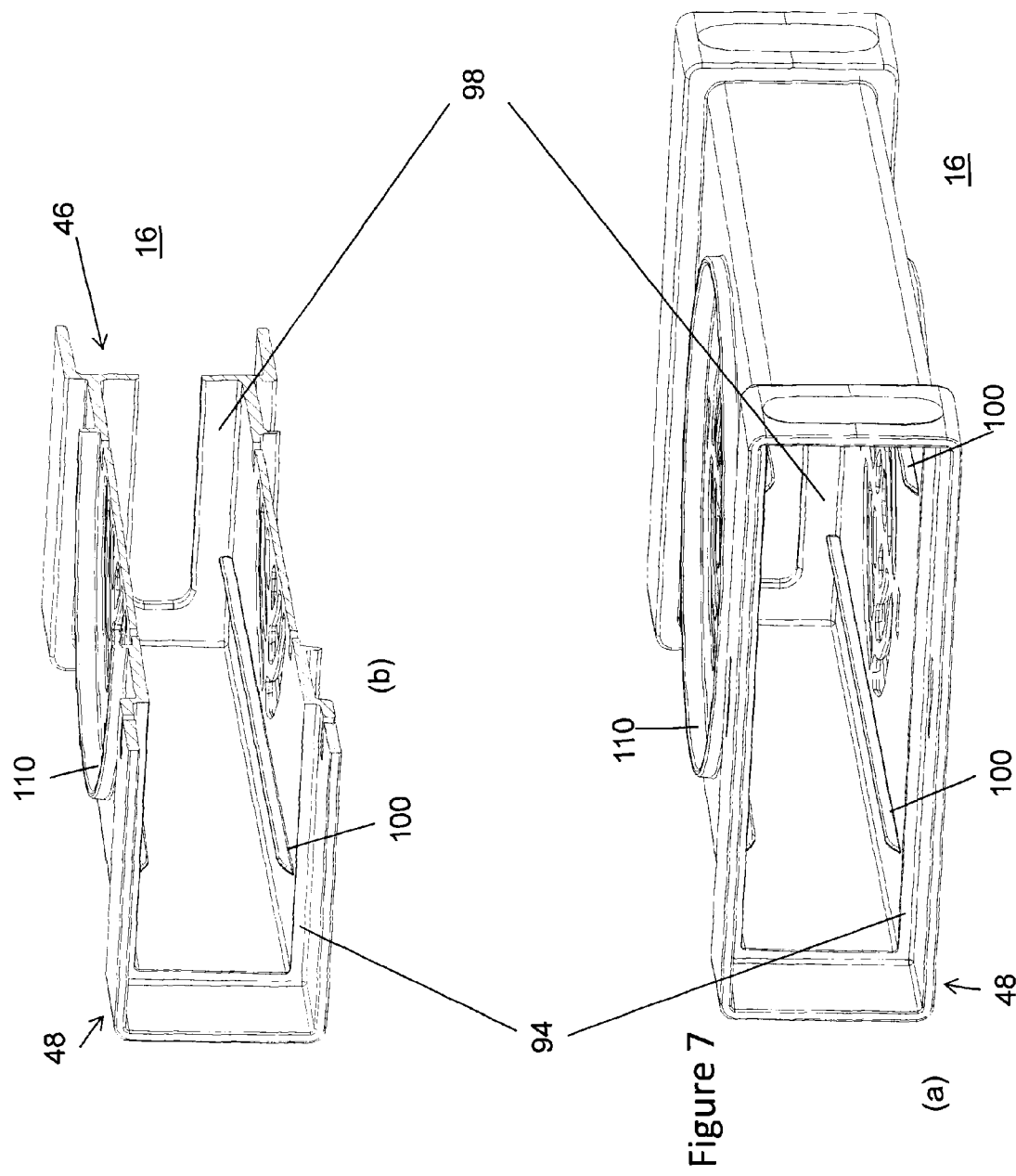

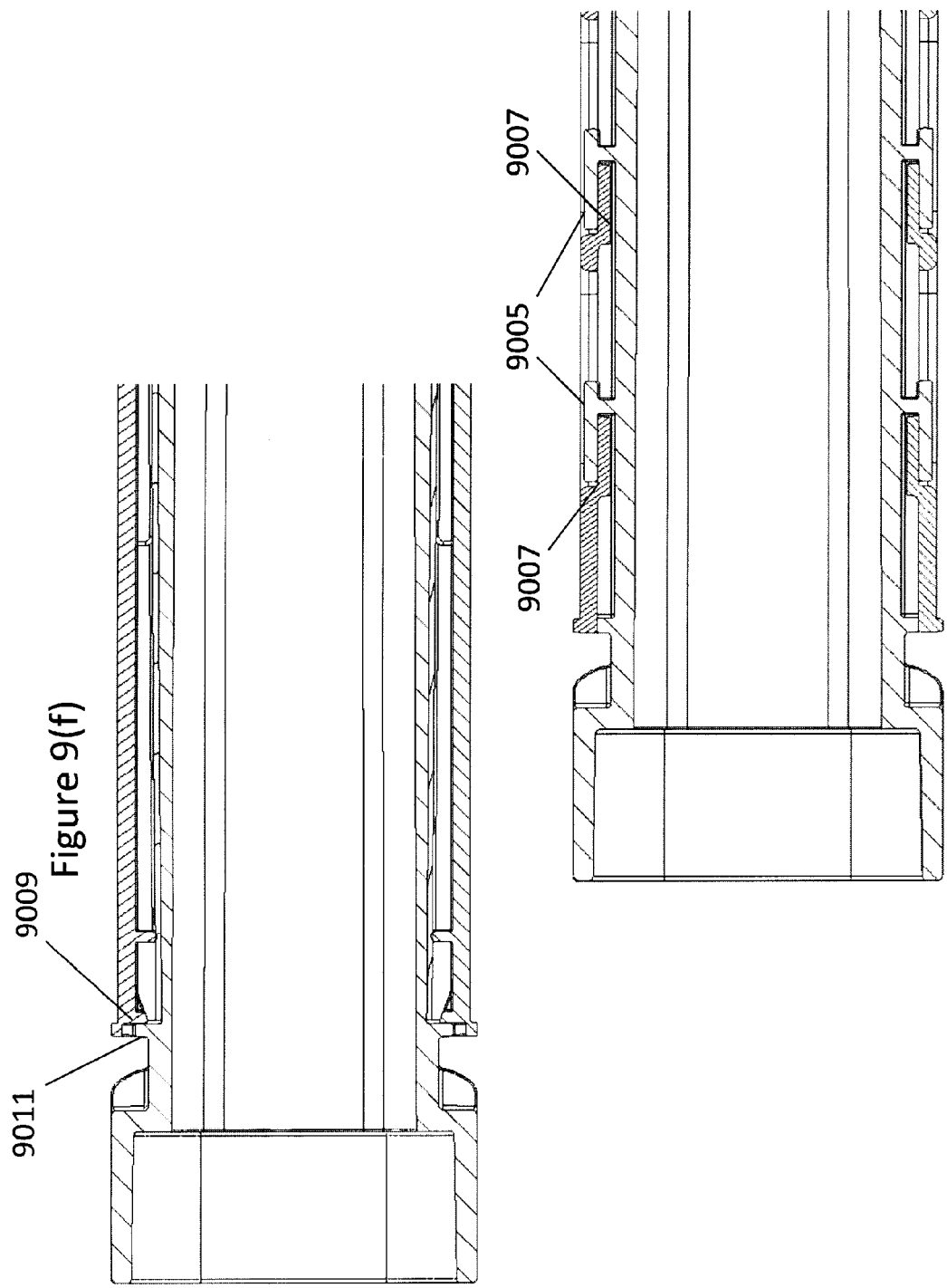

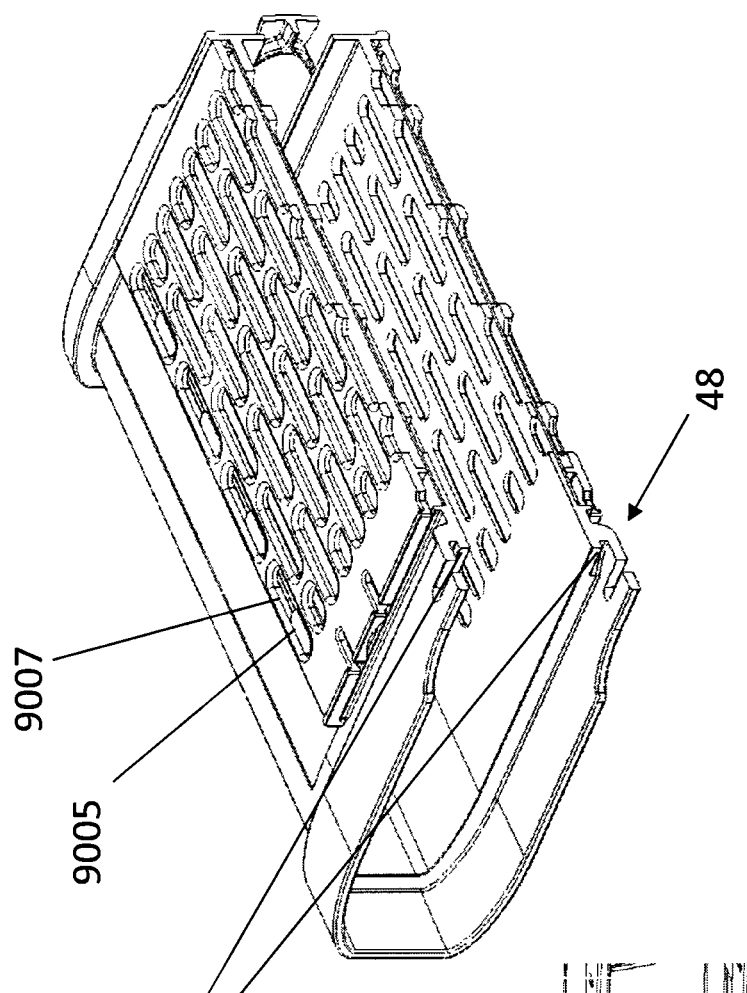
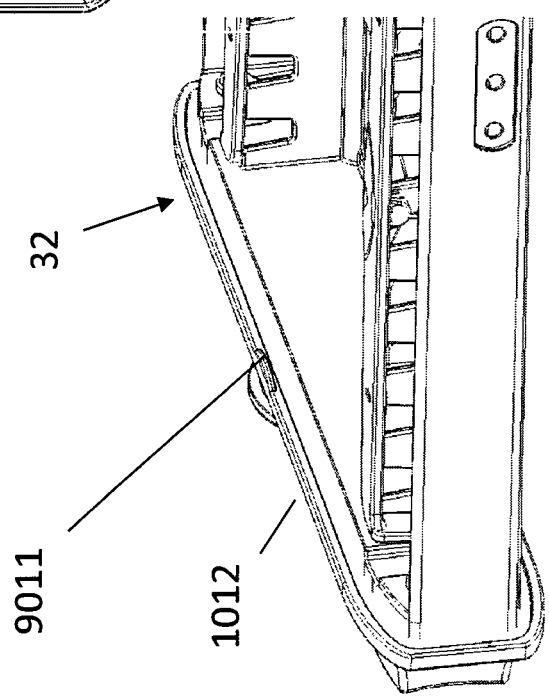
Figure 9(j)
Figure 9(i)

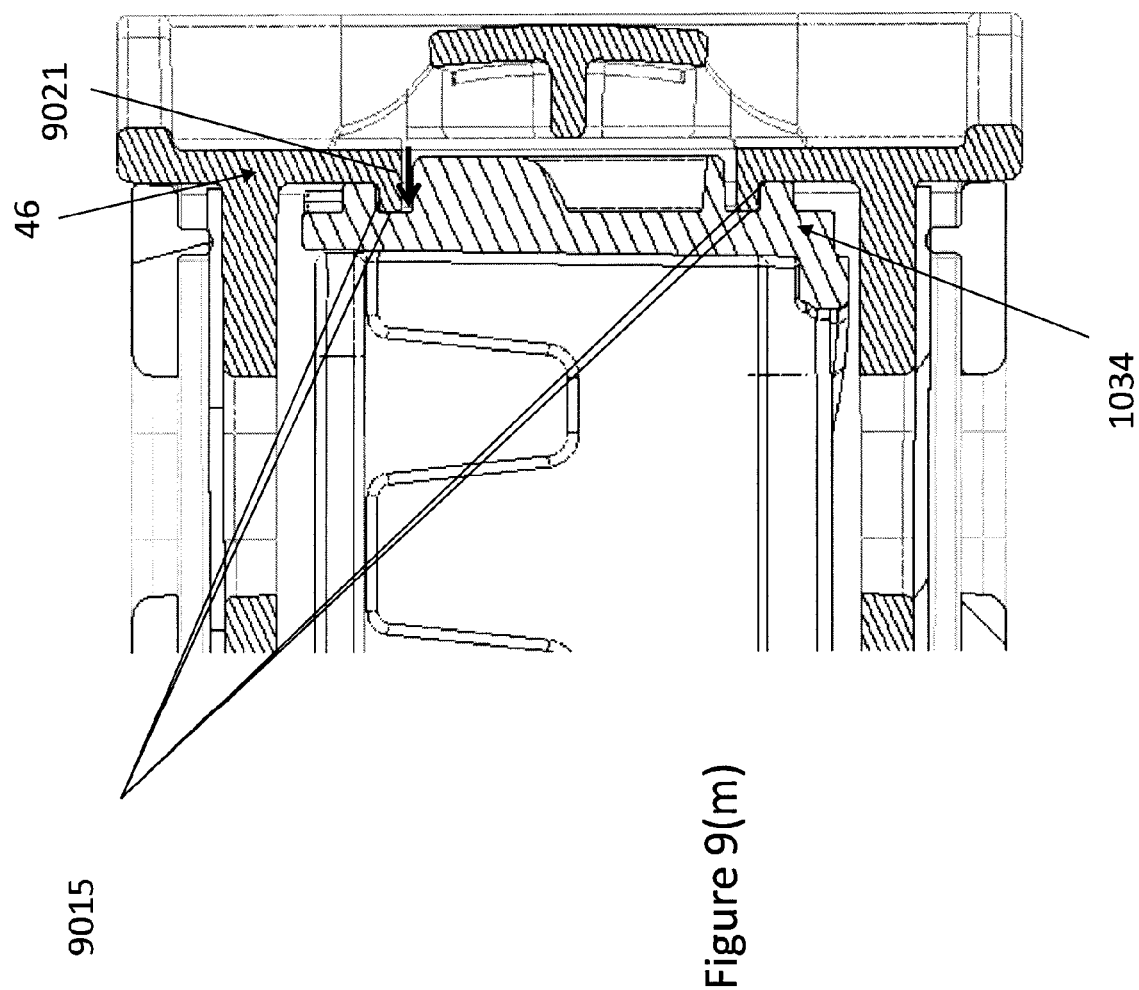

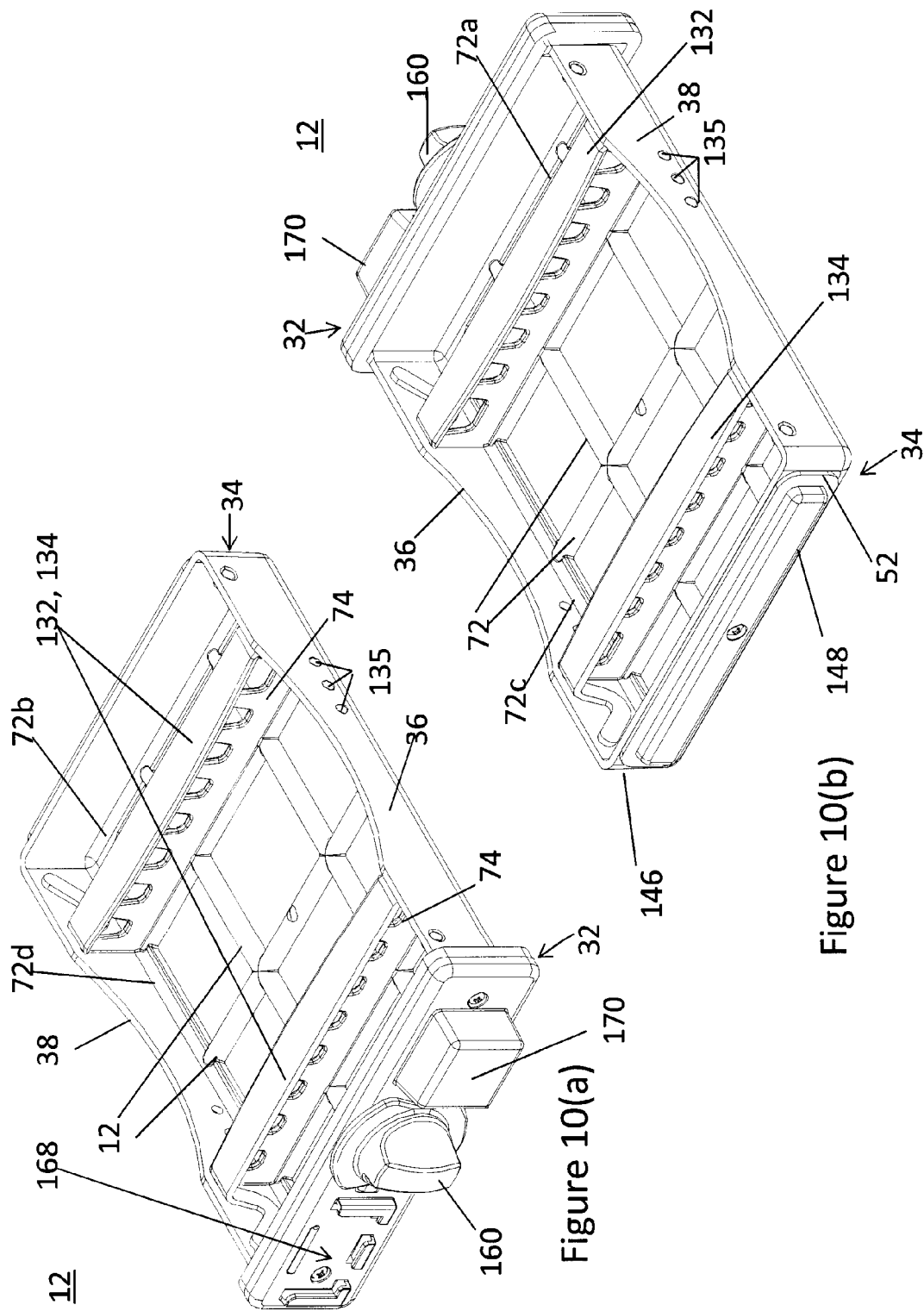

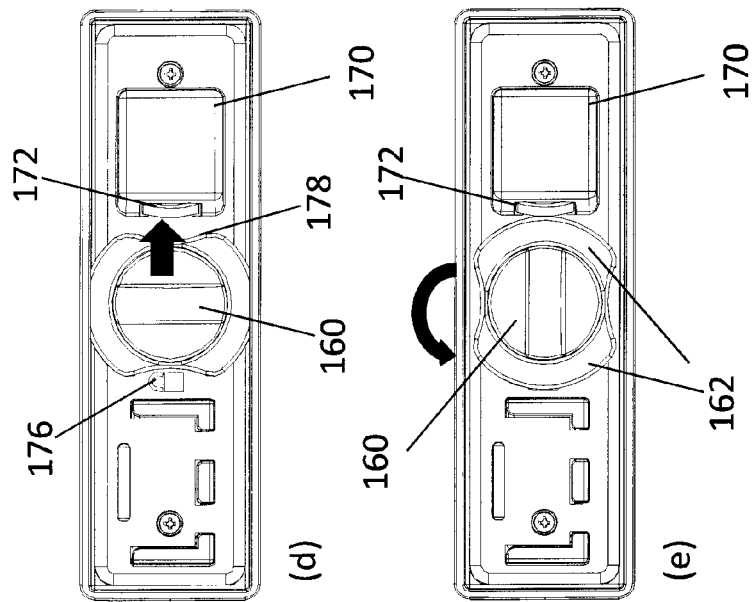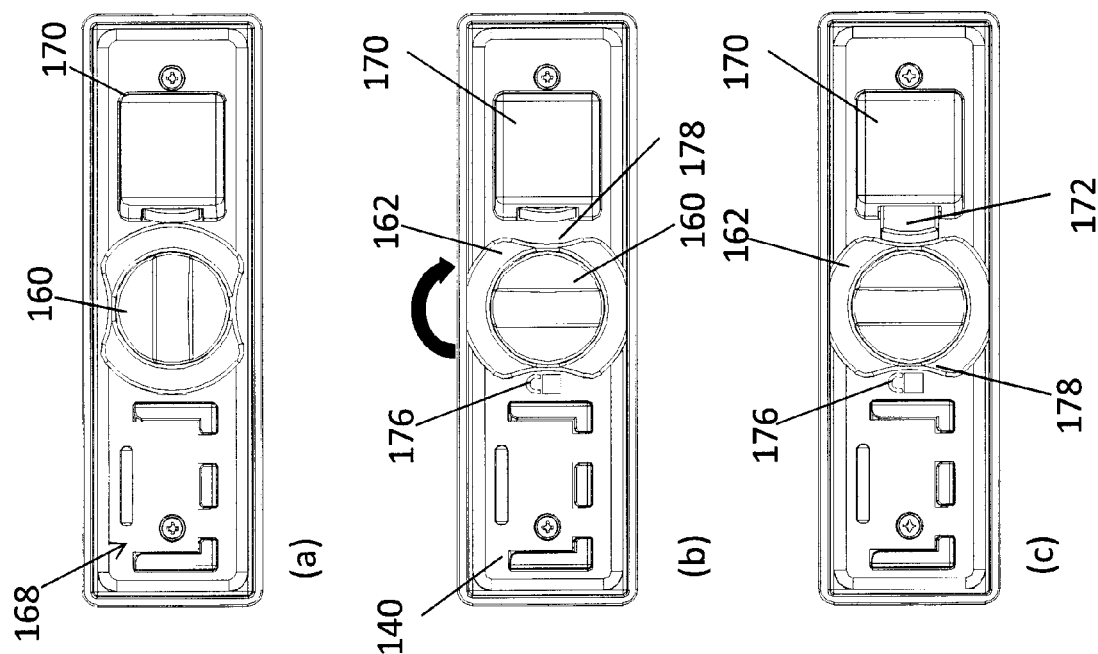
Figure 16

CONTAINER FOR WASHING STERILIZATION, TRANSPORTATION AND STERILE STORAGE OF ARTICLES

RELATED APPLICATION

This application claims the benefit of U.S. Provisional Application No. 61/680,482 filed on Aug. 7, 2012, which is herein incorporated by reference.

FIELD OF THE INVENTION

The present invention relates to a container for washing, sterilization, transportation and sterile storage of articles, such as medical or dental instruments, including containers which permit the passage of air and steam for sterilization of instruments held within the container and maintain sterile conditions for storage of instruments after sterilization.

BACKGROUND

Existing sterilization containers typically comprise a lid and a tray. Instruments for sterilization or procedural cassettes containing a set of instruments are placed within the container for sterilization and sterile storage. Other containers may be placed in a sterilization pouch or wrapped in sterilization wrap for sterilization and sterile storage.

Containers which comprise a lid and a tray may require additional work area during use since the lid must be removed from the tray and the instruments are usually removed from the tray and placed on a counter or other work surface during use. The storage of such containers also may be limited as the containers may be difficult to stack or may be stacked only in one orientation. Most containers are comprised of metal, such as stainless steel, or are wrapped as described above and do not permit the contents of the containers to be viewed. Some sterilization containers do not have adequate openings to allow effective cleaning of the articles contained therein during, for example, a wash process in an automatic instrument washer.

SUMMARY

A container for washing, sterilization, transportation and sterile storage of articles for sterilization, such as medical or dental instruments, is provided. The container includes a sleeve and a frame adapted to receive articles for sterilization. The container may be placed in a sterilization apparatus such as an autoclave. The container includes at least one opening equipped with a microbial filter or tortuous paths to permit communication between the sterilization apparatus and the sterilization chamber for the communication of steam. At least one portion of the container is transparent or semi-transparent to allow visual identification of contents and assessment of sterility. In a first configuration, a front wall and rear wall of the frame engage the sleeve to create a sterilization chamber. The container may be stacked and stored in any orientation. In a second configuration, the frame rests or nests on top of the sleeve to permit access to and use of the sterilized articles. The container may include one or a plurality of openings for communication between a sterilization apparatus and the sterilization chamber and one or more filters adjacent to the pluralities of openings.

According to an embodiment of the present disclosure there is provided a container for washing, sterilization, transportation and sterile storage of articles. The container comprises a frame adapted to receive articles for sterilization, the frame having at least a front wall and a rear wall; a sleeve having a top panel, a bottom panel and first and second side panels, the top panel, bottom panel and two side panels defining a cavity for receiving the frame, the sleeve being engaged with the front and rear walls of the frame to define a sterilization chamber; and at least one opening to permit communication between a sterilization apparatus and the sterilization chamber.

According to another embodiment, there is provided a container for washing, sterilization, transportation and sterile storage of articles. The container comprises: a frame adapted to receive articles for sterilization, the frame having at least a front wall and a rear wall; a sleeve having a top panel, a bottom panel and first and second side panels, the top panel, bottom panel and two side panels defining a cavity for receiving the frame, the sleeve being sealably engaged with the front and rear walls of the frame to define a sterilization chamber; and at least one opening to permit communication between a sterilization apparatus and the sterilization chamber.

In some embodiments, the sleeve further comprises a first region, a second region disposed discretely from said first region, and a third region disposed discretely from said second region; a front interface configured between the first and second regions for engaging the front wall; and a rear interface configured between the second and third regions for engaging the rear wall.

In another embodiment, there is provided a method for washing and sterilization of articles. The method comprises: placing articles in a frame, the frame being adapted to receive articles for sterilization, the frame having at least a front wall and a rear wall; washing the frame and articles placed therein in a washing apparatus; inserting the washed frame and articles into a sleeve to form a container. The sleeve has a top panel, a bottom panel and first and second side panels. The top panel, bottom panel and two side panels define a cavity for receiving the frame. In some embodiments, the sleeve is sealably engaged with the front and rear walls of the frame to define a sterilization chamber. The container has at least one filtered opening to permit communication between a sterilization apparatus and the sterilization chamber. The method includes sterilizing the container and articles contained therein in a sterilization apparatus

BRIEF DESCRIPTION OF THE DRAWINGS

These and other advantages of the present disclosure will become apparent upon reading the following detailed description and upon referring to the drawings in which:

FIG. 7(a) is a view of a sleeve in accordance with the present disclosure and FIG. 7(b) is a sectional view of FIG. 7(a);

FIGS. 10(a) and (b) are front and rear isometric views of a frame in accordance with an embodiment of the present disclosure;

FIGS. 16(a) to (e) are front views of a container in accordance with an embodiment of the present disclosure;

Figure 1A:
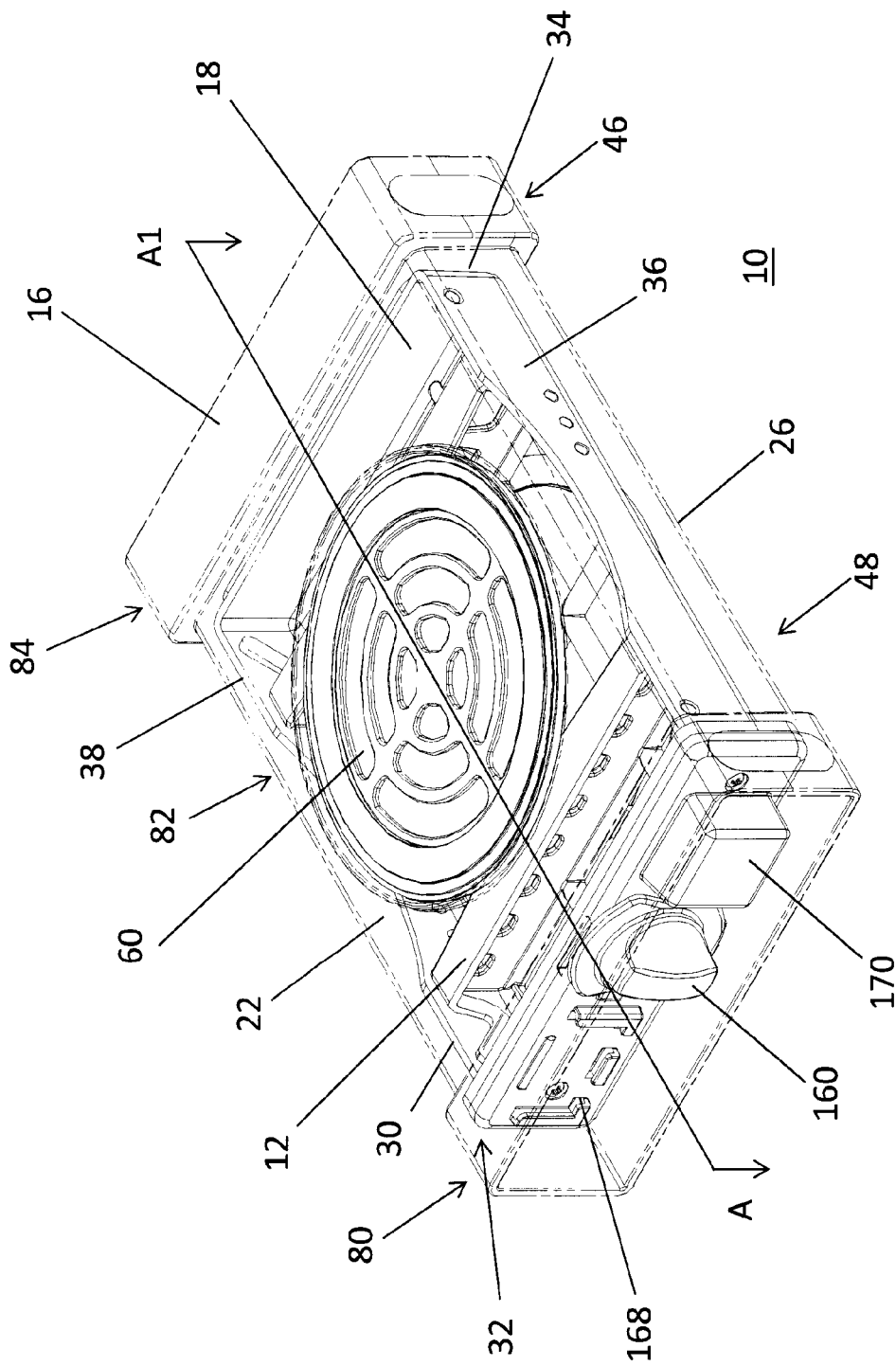
FIGS. 1 (*a*), (*b*) and (*c*) are perspective view of embodiments of a container in accordance with the present disclosure in a first configuration.

While the invention will be described in conjunction with the illustrated embodiments, it will be understood that it is not intended to limit the invention to such embodiments. On the contrary, it is intended to cover all alternatives, modifications and equivalents as may be included within the spirit and scope of the invention as defined by the appended claims.

DETAILED DESCRIPTION OF THE PREFERRED EMBODIMENTS

In the following description, similar features in the drawings have been given identical reference numerals where appropriate. Terms such as "front" and "rear", "top" and "bottom", "first" and "second", "right" and "left" may be used to identify opposing ends or different configurations of structures. Such terms are used for illustration purposes and are not intended to limit the present disclosure.

An embodiment of the present disclosure provides a container assembly which holds articles for sterilization such as medical and dental instruments. The components of the assembly may be placed in a washer apparatus to wash the instruments and remove debris prior to a sterilization process. One or more containers may be placed in a sterilization apparatus such as an autoclave or a cassette sterilization apparatus such as the STATIM™ for sterilization of the articles in the container. The container also allows for sterile storage and transport of instruments and provides improved access to instruments during use. The container comprises a sleeve, and a frame adapted to receive articles for sterilization. The sleeve has a top panel, a bottom panel and two side panels which define a cavity for receiving the frame. The sleeve and the frame are engaged to create a sterilization chamber. In one embodiment, the sleeve and the frame are sealably engaged. In another embodiment, tortuous paths are configured at the engagement between the frame and the sleeve. The container includes at least one opening to permit communication between a sterilization apparatus and the sterilization chamber, such as for the communication of steam. In one embodiment, the container includes a plurality of openings for communication between a sterilization apparatus and the sterilization chamber and one or more filters adjacent to the pluralities of openings.

In one embodiment, the container has two configurations. In a first configuration, the frame is housed within the sleeve and a front wall and rear wall of the frame engage the sleeve to create the sterilization chamber. In one embodiment, the front wall and rear wall are adapted to attach to opposing ends of a tray, cassette or basket configured to fit within a suitably sized sleeve of the container. In another embodiment, the frame comprises a front wall, a rear wall and first and second side walls which are adapted to receive articles for sterilization as described herein. The frame may be inserted or slid into the sleeve in order to assemble the container in the first configuration. In the first configuration, the container and articles contained therein may be sterilized and stored efficiently by standing and stacking multiple containers in any orientation. Sterile articles held within the container in the first configuration may remain in the container and transported to a point of use.

In a second configuration, the frame rests or nests on top of the sleeve to permit access to and use of the sterilized articles. After sterilization, or after a sterilized container is removed from storage, the sterile seal may be broken at the point of use, such as in the presence of a medical or dental patient, and the frame and articles contained therein may be removed from the sleeve. For example, the frame and articles contained therein may be removed from the sleeve by sliding the frame out of the sleeve. The frame is sized to rest atop either a top panel or bottom panel of sleeve. In one embodiment, the frame nests within or partially within the top panel or bottom panel of the sleeve. The second configuration permits use of the container and articles using a minimal area or footprint since the frame may rest on top of the sleeve and the sleeve need not be stored elsewhere.

After the articles or instruments are used, they may be returned to the frame and the frame and articles contained therein may be placed into the sleeve to assemble the container in the first configuration for transport, thus reducing the risk of infection due to exposure and minimizing the risk of instrument damage due to improper handling. The frame and articles contained therein may be removed from the sleeve and the components washed, such as in an automatic washer, without removing the articles from the frame. The sleeve and frame may be reassembled in the first configuration for sterilization of the articles in the frame and subsequent sterile storage.

In some embodiments, the sleeve or at least a portion of the sleeve comprises a transparent material to enable visibility of the articles held or stored in the container. In other embodiments, mechanisms are provided to indicate whether the container has undergone a sterilization cycle and remains in a sterile condition or whether it has been accessed.

FIGS. 1(a), (b) and (c) illustrate embodiments of a container 10, 1000 according to the present disclosure. The container 10, 1000 comprises a frame 12 and a sleeve 16. The container 10, 1000 is shown in a first configuration with the frame 12 contained within the sleeve 16. The sleeve 16 and frame 12 engage to create a sterilization chamber 18.

As shown in FIGS. 1(a)-(c) and 2, the sleeve 16 comprises a top panel 22, a bottom panel 24, a first side panel 26 and a second side panel 28. The top panel 22, bottom panel 24, first side panel 26 and second side panel 28 define a cavity 30 for receiving and housing the frame 12. In one embodiment, the cavity 30 is generally rectangular in shape. The sleeve 16 may be constructed from one or more individual panels or constructed as one piece.

In one embodiment, the frame 12 includes at least a front wall 32 and a rear wall 34 which are adapted to receive or hold articles for sterilization. In one embodiment (not shown), the front wall 32 and rear wall 34 may be attached or affixed to an existing sterilization cassette or basket which is suitably sized and configured with openings for sterilization of instruments contained therein when inserted in a sleeve 16. In another embodiment (not shown), the front wall 32 and rear wall 34 may be attached or affixed to an existing sterilization cassette which can be inserted in a suitably sized sleeve (not shown). In yet another embodiment, the frame 12 includes the front wall 32, the rear wall 34 and a first side wall 36 and a second side wall 38. The frame 12 is configured or adapted to receive articles for sterilization as described in further detail below.

Figure 3A:
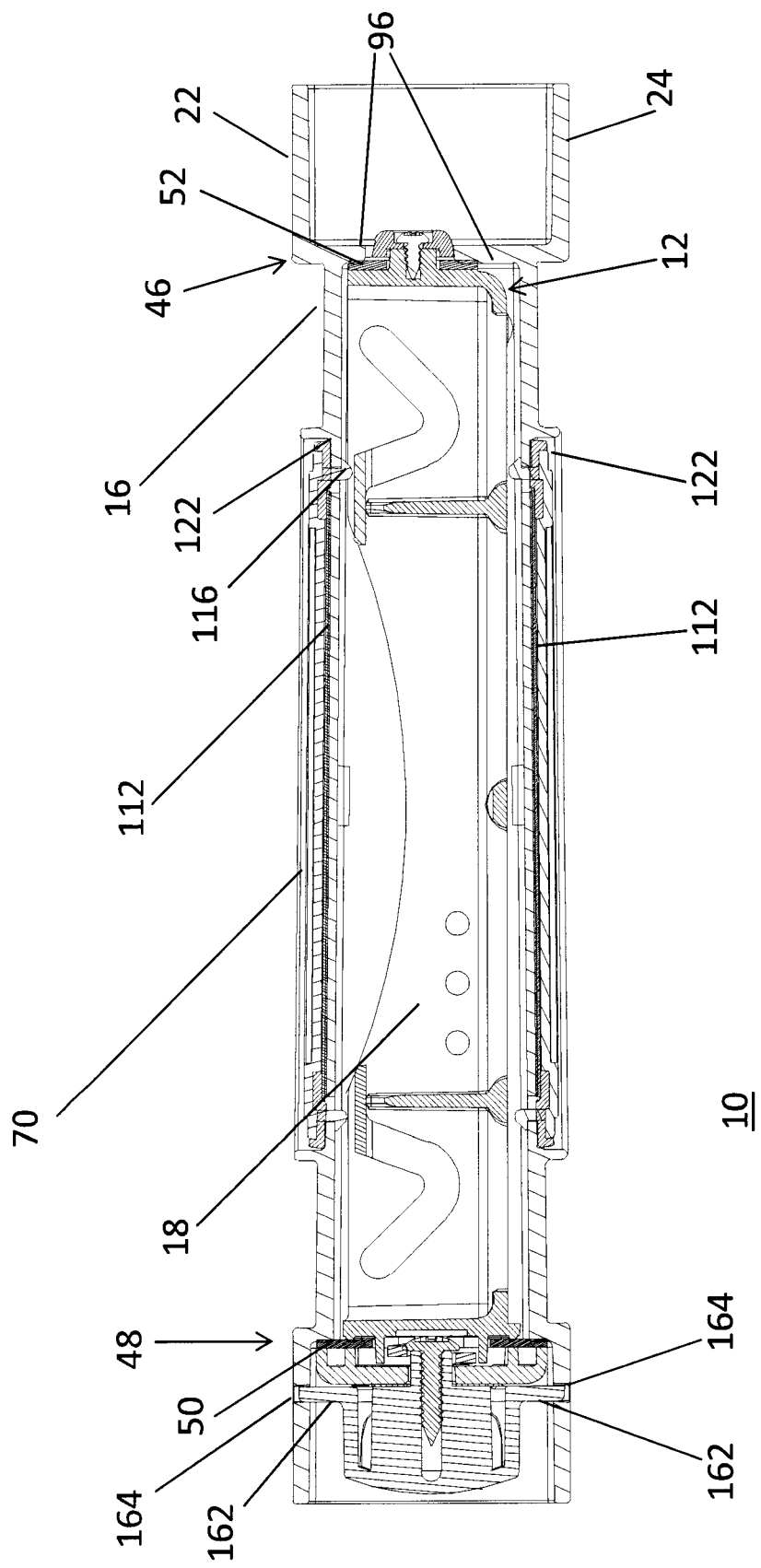
FIG. 3(*a*) is a longitudinal cross-section view of the container at line A-A' of FIG. 1(*a*), and FIG. 3(*b*) is a longitudinal cross-section view of the container of FIG. 1(*b*)
Figure 3B:
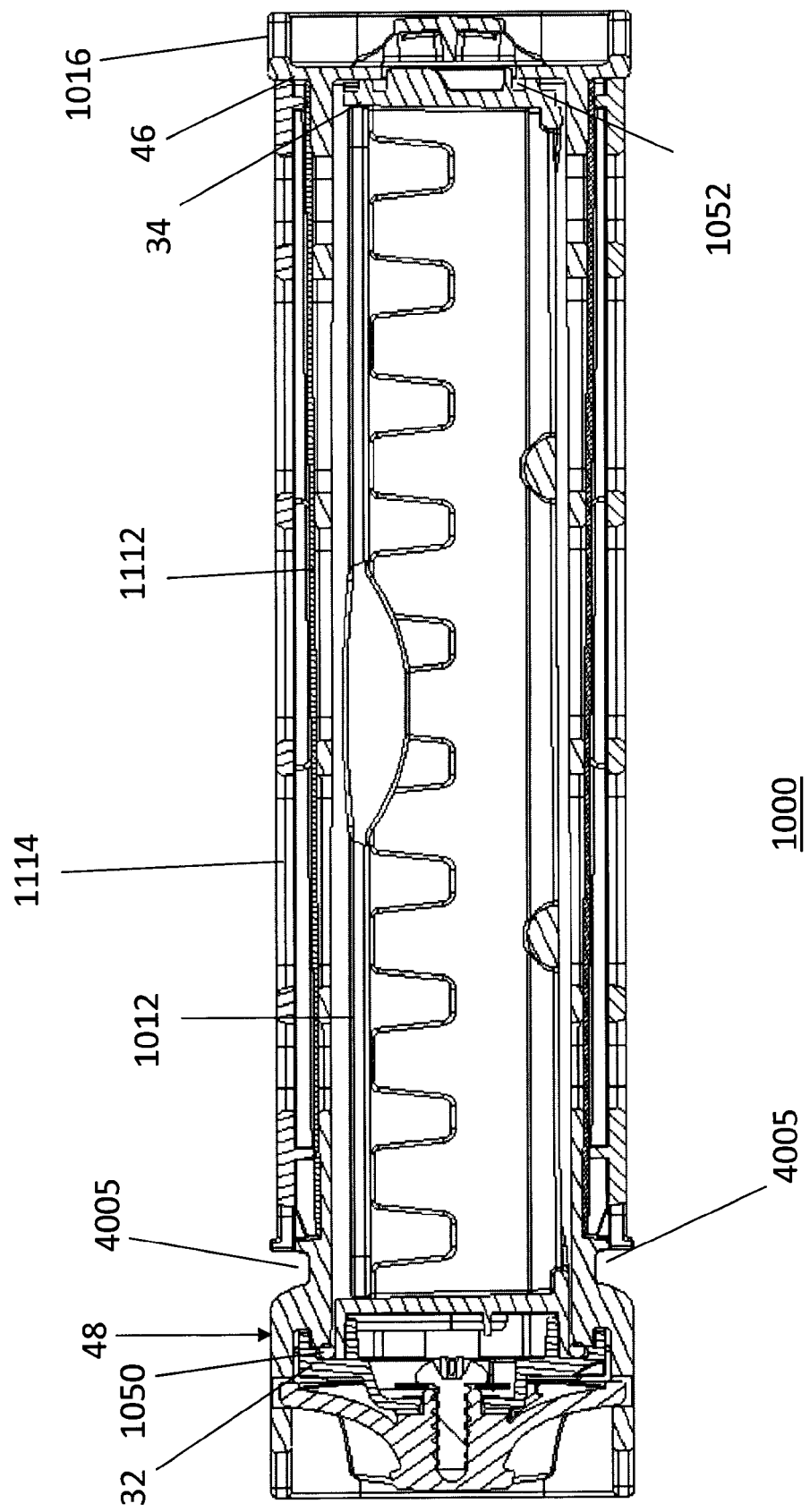
Figure 4A:
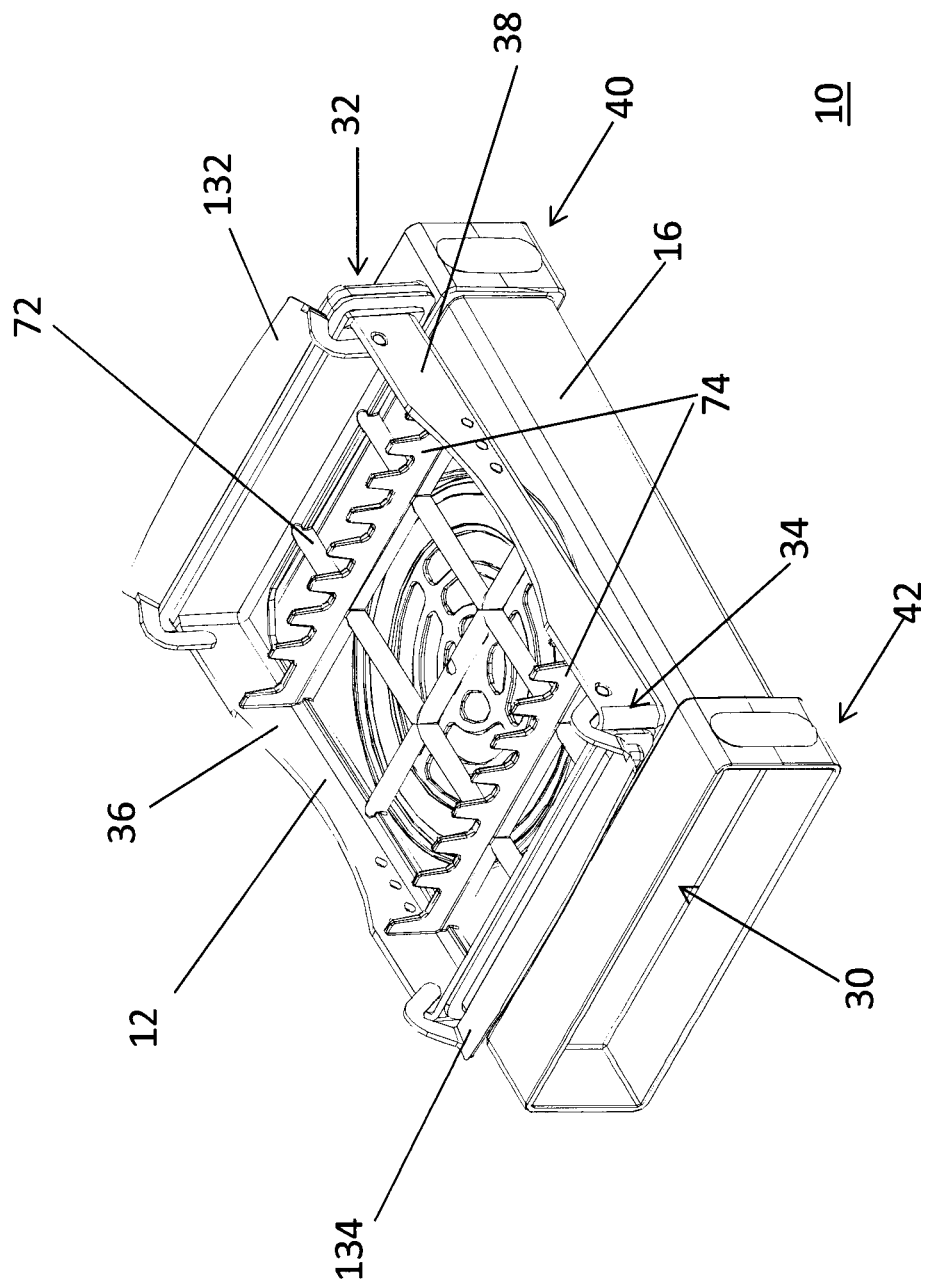
FIG. 4(*a*) is a perspective view of one embodiment of a container in accordance with the present disclosure in a second configuration, FIG. 4(*b*) is a perspective view of one embodiment of a container in accordance with the present disclosure in a second configuration and FIG. 4(*c*) is a side view of the container of FIG. 4(*b*)

As illustrated in FIGS. 3(a), 3(b) and 4(a), the frame 12 and sleeve 16 are sealably engaged to define the sterilization chamber 18. In one embodiment, the frame 12 slides through a front end 40 of the sleeve 16 towards a rear end 42 of the sleeve 16. A rear interface 46 at the rear end 42 of the sleeve 16 engages the rear wall 34 of the frame 12. A front interface 48 at the front end 40 of the sleeve 16 engages the front wall 32 of the frame 12. In one embodiment, the rear wall 34 of the frame 12 first sealably engages the rear interface 46 of the sleeve 16 and the front wall 32 of the frame 12 then engages the front interface 48 of the sleeve 16 as the frame 12 is slid into the sleeve 16. In another embodiment, the front wall 32 of the frame 12 first engages the front interface 48 of the sleeve 16 and then the rear wall 34 of the frame 12 sealably engages the rear interface 46 of the sleeve 16 as the frame 12 is slid into the sleeve 16.

Figure 1B:
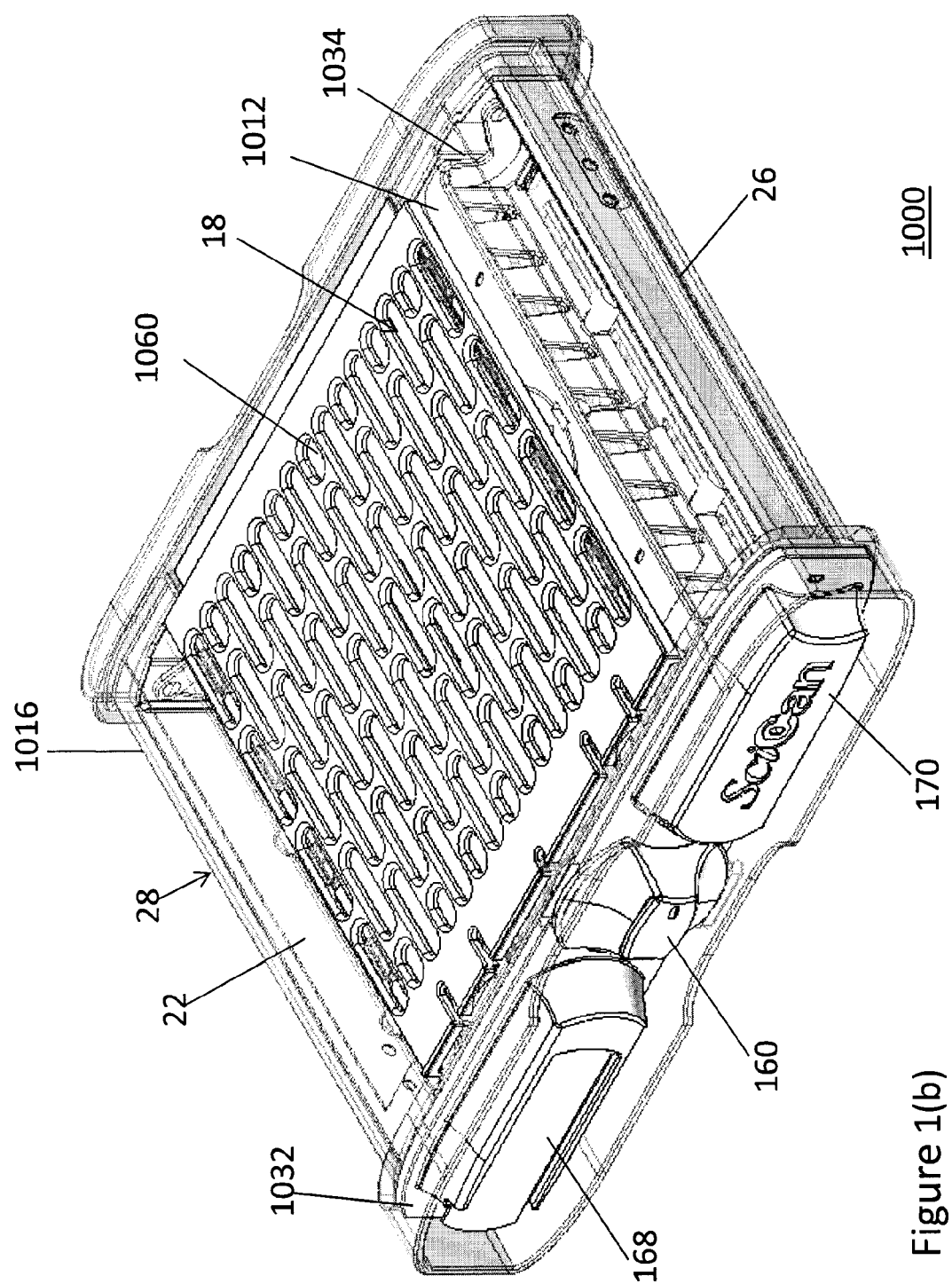
Figure 1C:
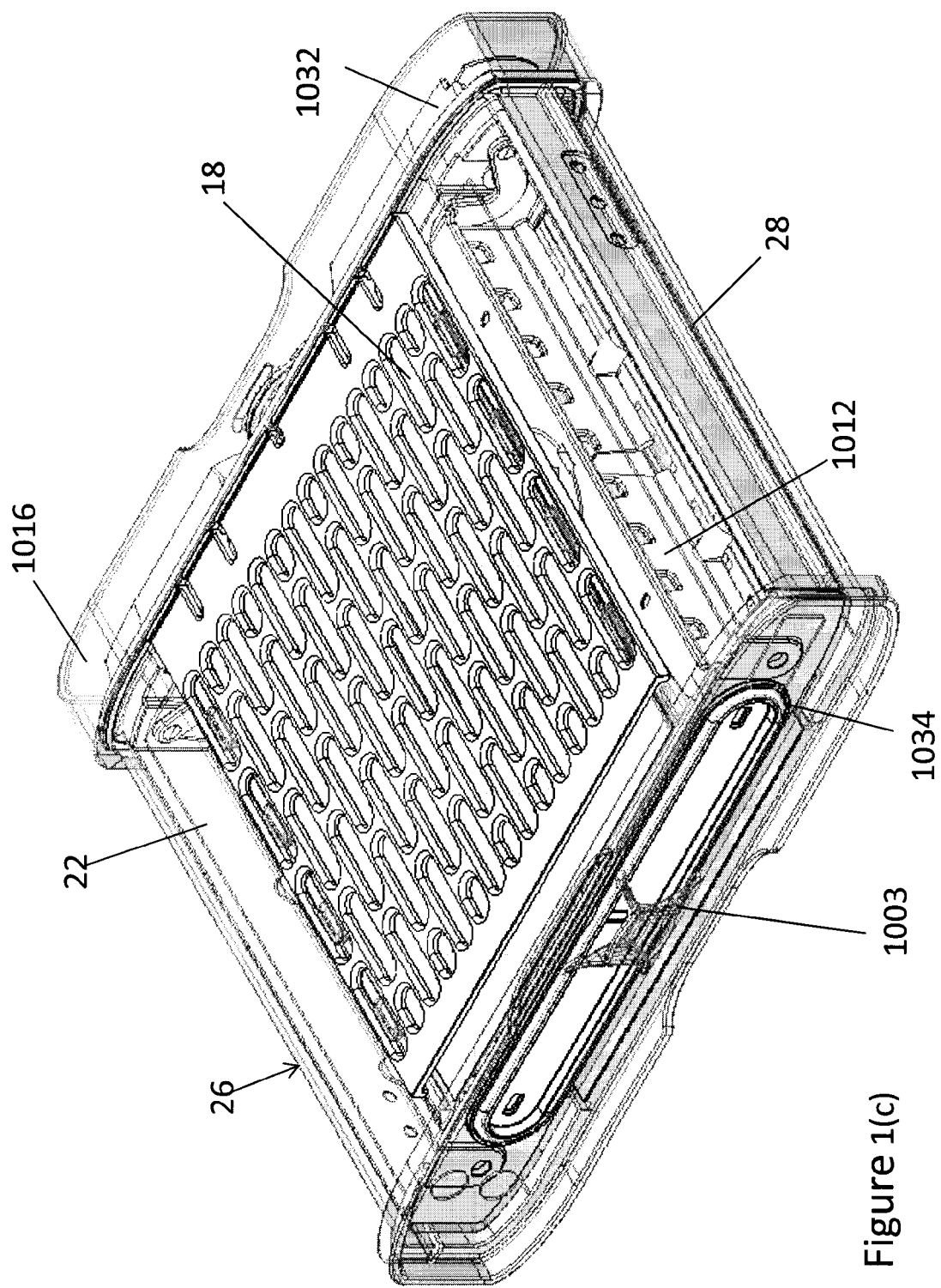

The dimensions of the container 10, 1000 and the sleeve and frame components may vary, as described below. In some embodiments, the sides of the container, and its frame and sleeve components, are longer than the width of the front and rear ends and the frame is inserted and extends lengthwise through the sleeve as illustrated in FIG. 1(a). In other embodiments, the sides of the container, and its frame and sleeve components, are shorter than the width of the front and rear ends and the frame is inserted and extends widthwise through the sleeve as illustrated in FIGS. 1(b) and (c).

The container 10, 1000 may include a front seal 50 and a rear seal 52 at the respective front and rear interfaces 48, 46, or one or more tortuous paths at the front and rear interfaces 48, 46, or a combination of seals and tortuous path configurations. A tortuous path refers to a winding or turning path wherein turns in the path inhibit the entrance and travel of bacteria into the container 10, 1000 and sterilization chamber 18. A tortuous path may be created between the front wall 32 of the frame 12 and the front interface 48 of the sleeve 16 by providing, for example, a number of complementary protrusions and/or recesses in the mating surfaces of the front wall 32 and front interface 48 as illustrated in at least FIG. 3(b). Similarly, a tortuous path may be created between the rear wall 34 of the frame 12 and the rear interface 46 of the sleeve 16 by providing, for example, a number of complementary protrusions and/or recesses in the mating surfaces of the rear wall 34 and rear interface 46. One or a plurality of tortuous paths between the front wall 32 and front interface 48 and between the rear wall 34 and rear interface 46 inhibit the entrance of bacteria into the container 10 and sterilization chamber 18.

In one embodiment, the container 10, 1000 includes at least one opening for communication between a sterilization apparatus and the sterilization chamber 18. In another embodiment, the container 10, 1000 includes a plurality of openings, such as multiple openings in one of the panels of the sleeve 16. In the embodiments shown in FIGS. 1(a)-(c) and 2, the container 10 comprises a plurality of openings 60 in the top panel 22 and a plurality of openings 62 in the bottom panel 24. The pluralities of openings 60, 62 allow for communication between a sterilization apparatus and the sterilization chamber 18 as described in detail below. One or more filter assemblies 70, also described in further detail below, may be provided adjacent to the plurality of openings 60, 62. In some embodiments, the pluralities of openings 60 may be in the side panel 26 and the pluralities of openings 62 may be in the side panel 28.

To assemble one embodiment of the container 10, 1000 in the first configuration for sterilization, articles are placed in the frame 12 and the frame 12 is inserted into the cavity 30 of the sleeve 16. The frame 12 and sleeve 16 engage to create the sterilization chamber 18. The container 10, 1000 may be placed in a sterilization apparatus and cycles of steam for sterilization and air for drying of the articles within the container 10 pass through the filter assemblies 70 and the one or more pluralities of openings 60, 62. After sterilization, the container 10 may be removed from the sterilization apparatus and stored which provides for sterile storage of the articles in the container 10, 1000. In one embodiment, the container 1000 includes a rear handle 1003 which may be used along with a knob 160 provided on the front wall 32 of the frame 12 for carrying the container 1000 when the container is hot.

Figure 2:
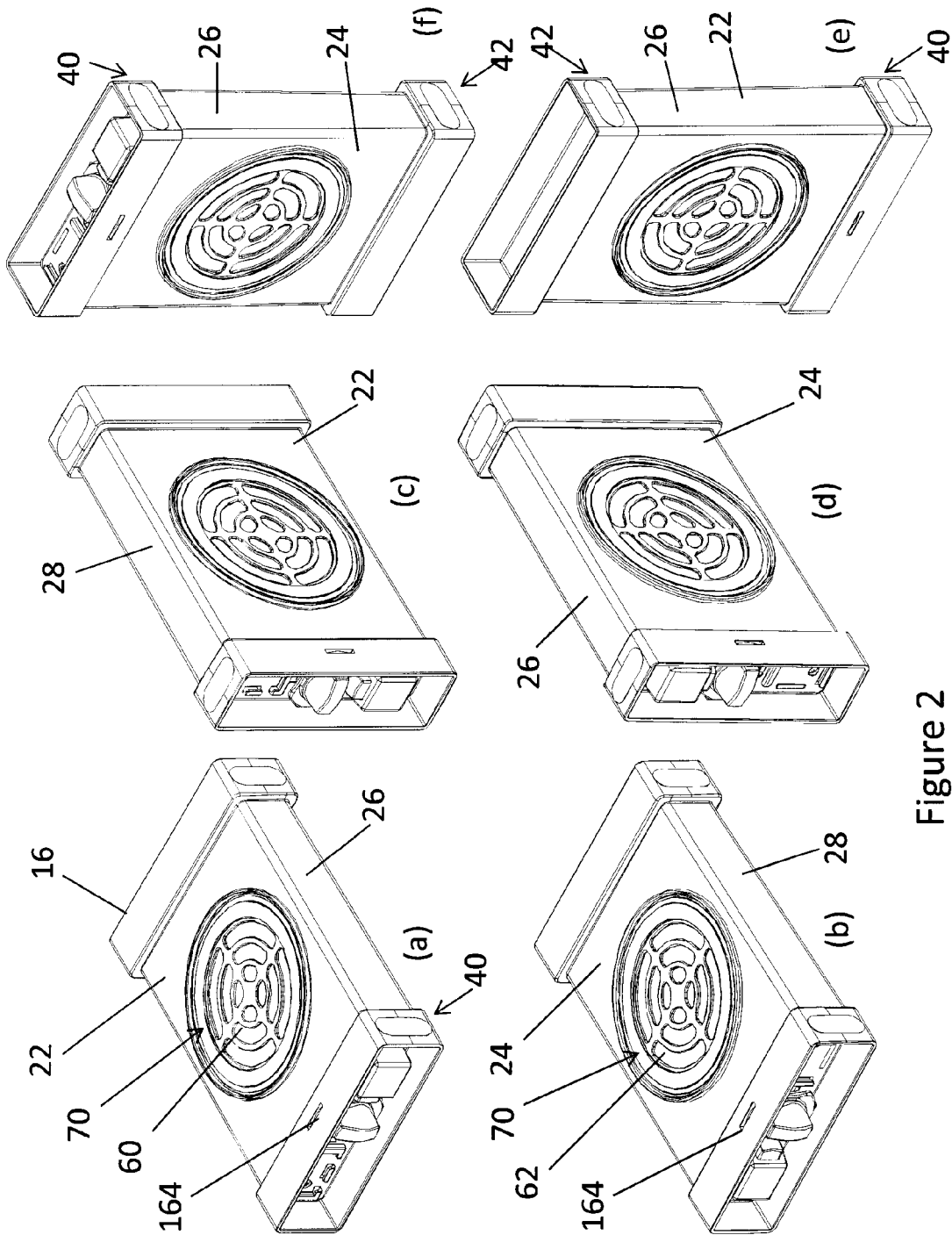
FIGS. 2(*a*) through (*h*) illustrate embodiments of a container in accordance with the present disclosure in multiple orientations.
Figure 2G:
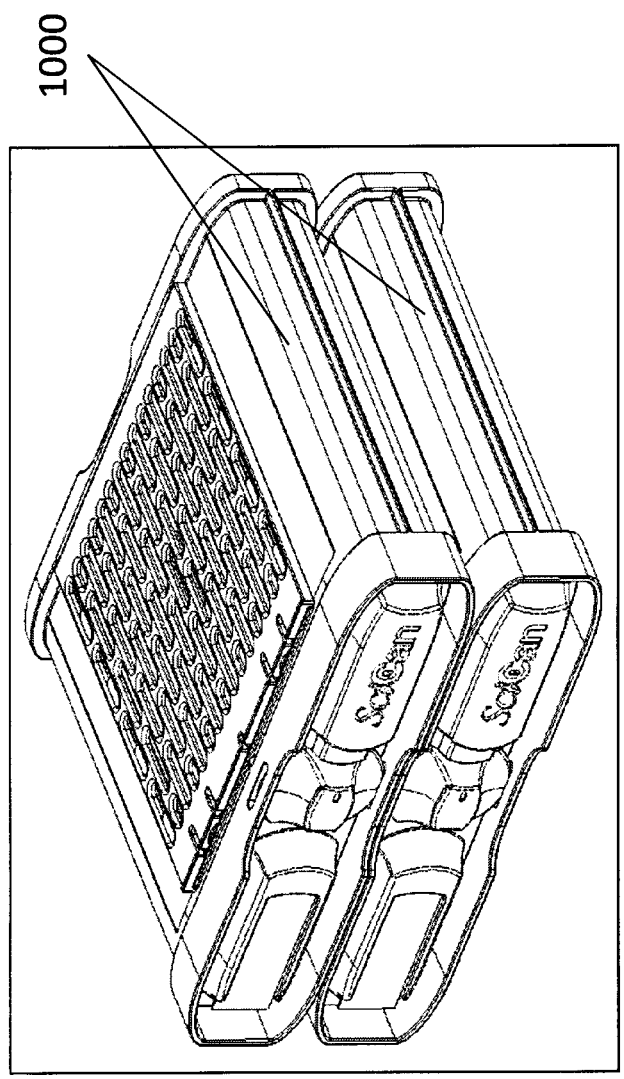
Figure 2H:
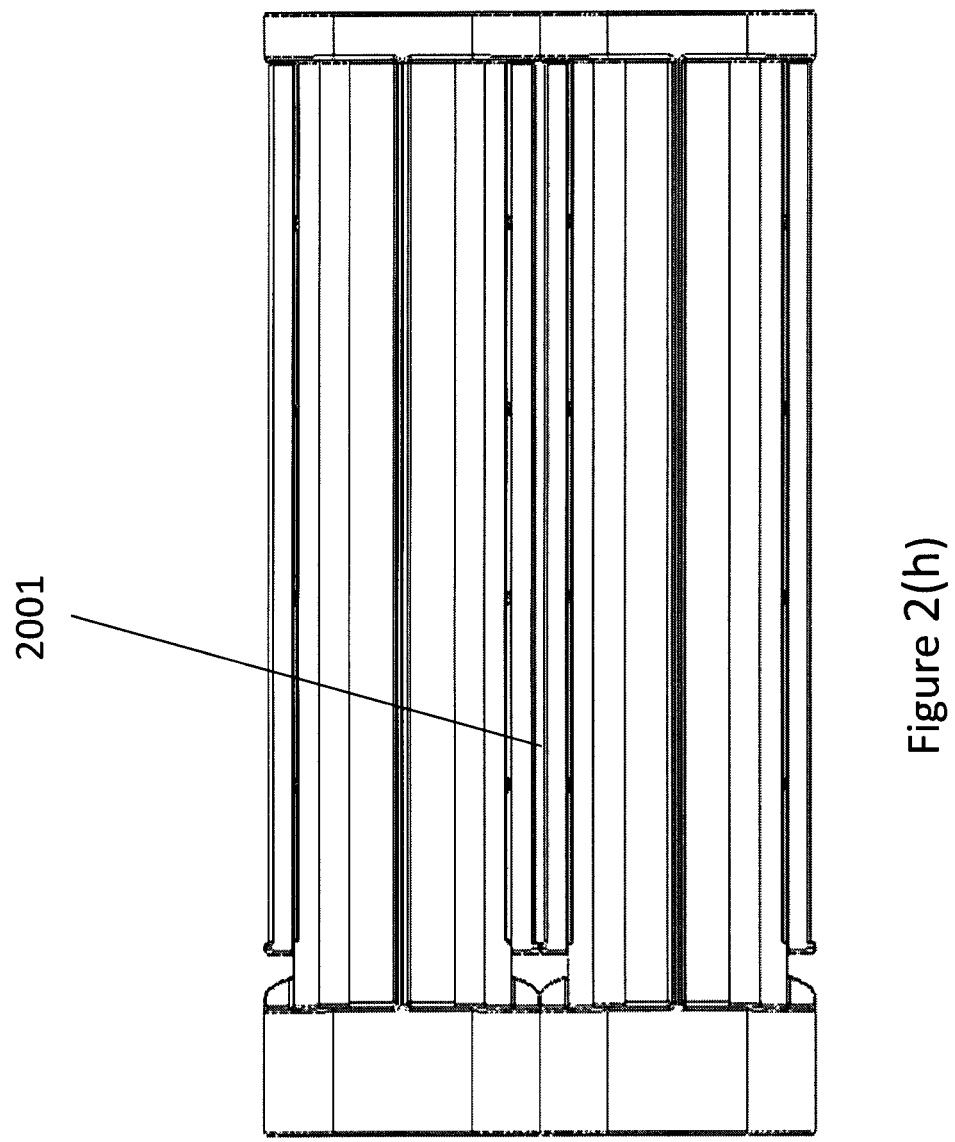

As shown in FIG. 2, the container 10, 1000 may be freestanding in any orientation. Thus, one or more containers 10, 1000 according to the present disclosure may be stacked and stored in various configurations. The container 10, 1000 may stand or be stored on the bottom panel 24 as shown in FIG. 2(a). The container 10, 1000 may stand or be stored on the top panel 22 as shown in FIG. 2(b). The container 10, 1000 may stand or be stored on the first side panel 26 as shown in FIG. 2(c). The container 10, 1000 may stand or be stored on the second side panel 28 as shown in FIG. 2(d). The container 10, 1000 may stand or be stored on the front end 40 of the sleeve 16 as shown in FIG. 2(e). The container 10, 1000 may stand or be stored on the rear end 42 of the sleeve 16 as shown in FIG. 2(f). As illustrated in FIGS. 2(g) and 2(h) and described below, the container 10, 1000 may be stacked while in storage or while in a sterilization chamber with a gap 2001 created between adjacent containers 10, 1000 to facilitate air removal, condensate drainage and steam penetration during sterilization.

Figure 4B:
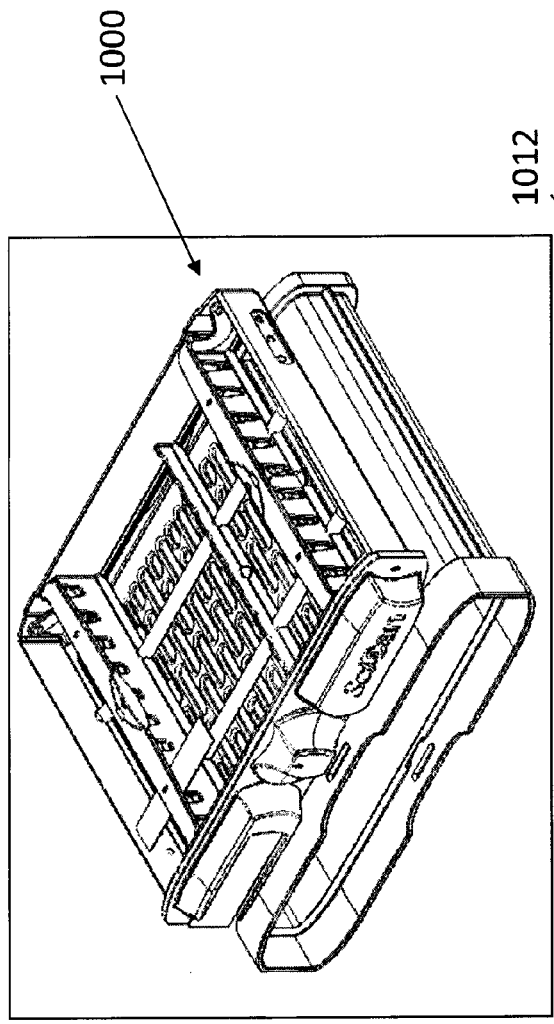
Figure 4C:
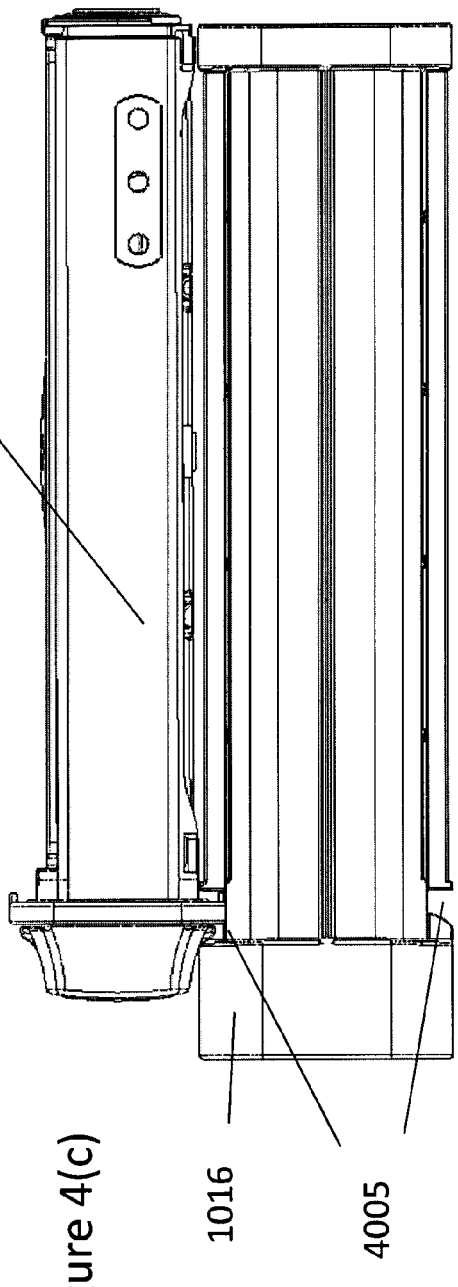

FIG. 4(a) illustrates an embodiment of a container 10 in a second configuration wherein the frame 12 is removed from and rests on top of the sleeve 16. FIG. 4(a) illustrates the frame 12 resting on top of the top panel 22 of the sleeve 16. Alternatively, the frame 12 may rest on the bottom panel 24 when the sleeve 16 is oriented to stand on the top panel 22 as shown in FIG. 2(b). FIGS. 4(b) and (c) illustrate a container 1000 in a second configuration wherein the frame 12 is removed from and rests on top of the sleeve 1016. A groove or channel 4005 may be provided in the top panel 22 of the sleeve 16, as shown in FIGS. 3(b), 4(b) and 4(c) to accommodate the front wall 32 of the frame 12 for the frame 12 to rest level with the sleeve 16. Alternatively, the frame 12 may rest on the bottom panel 24 of the sleeve 16, the bottom panel 24 having a similar groove 4005

In the embodiment shown in FIG. 4(a), the frame 12 comprises a front wall 32, a rear wall 34, a first side wall 36 and a second side wall 38. The frame 12 is adapted to receive articles such as medical or dental instruments for sterilization. As described further below, in some embodiments, the frame 12 includes members 72 to maintain the structure of the frame 12. In some embodiments, the frame 12 includes one or more spacers 74 to receive articles for sterilization.

Figure 5:
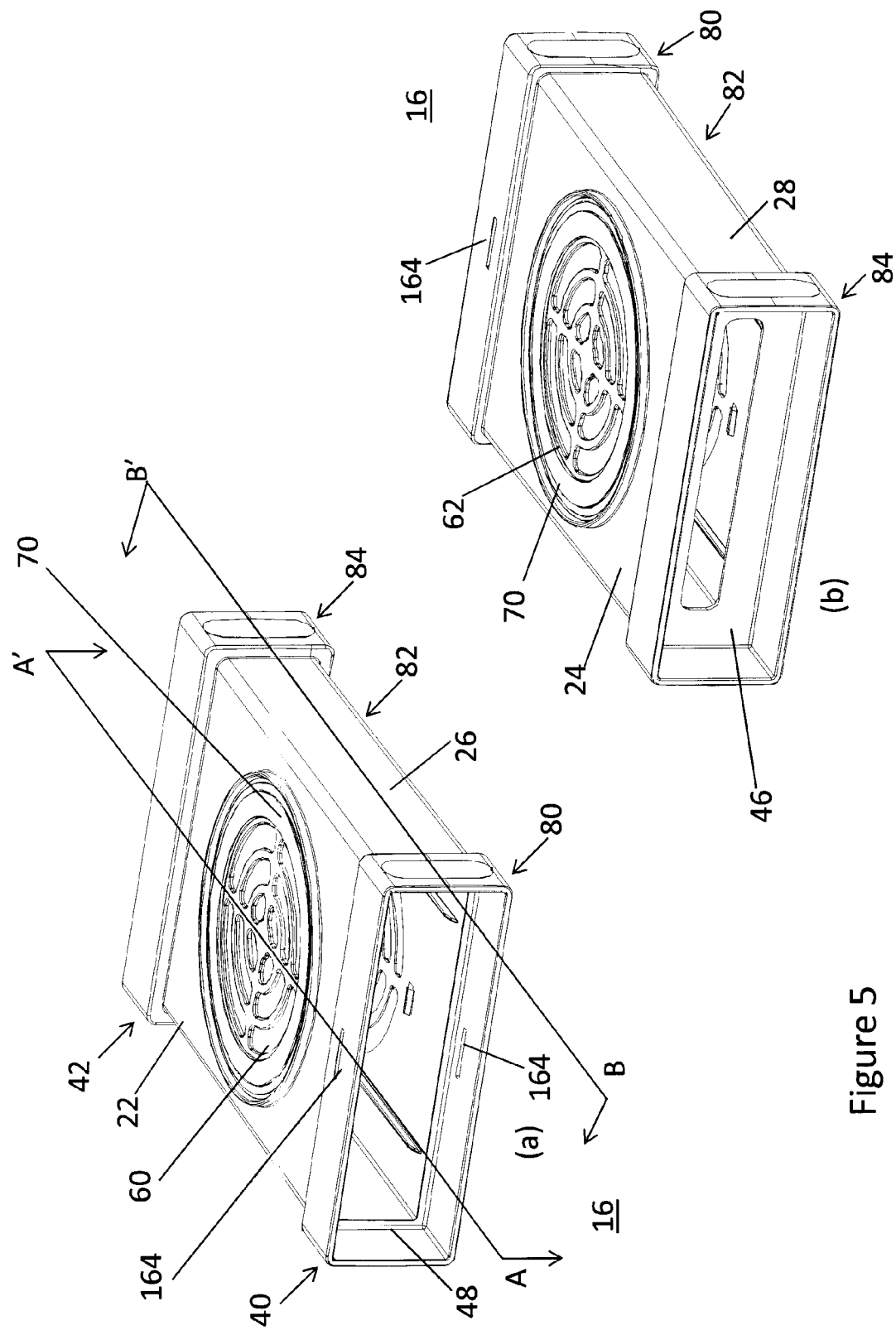
FIGS. 5(a) and (b) are front-top and rear-bottom isometric views of a sleeve in accordance with an embodiment of the present disclosure.

FIGS. 5(a) and (b) illustrate an embodiment of a sleeve 16 according to the present disclosure. The sleeve 16 is shown with the top panel 22 facing upwards in FIG. 5(a) and with the bottom panel 24 facing upwards in FIG. 5(b). In some embodiments, the sleeve 16 comprises a generally symmetrical construction as shown in the figures. While a symmetrical construction aids in the efficient storage and standing of containers, it will be appreciated that other external configurations or external dimensions of the sleeve 16 may be provided.

In one embodiment, the sleeve 16 comprises a transparent or semi-transparent plastic material. The sleeve 16 may be comprised of polyetherimide (PEI) or polyphenylsulfone (PPSU) or any other suitable material which may withstand multiple washing and sterilization cycles and which is transparent or semi-transparent, such as tempered glass or borosilicate glass. The transparent or semi-transparent material of the sleeve 16 allows the contents of the container 10 to be visibly identified without the use of labels. A transparent or semi-transparent sleeve 16 also allows the status or sterility of the contents be assessed without breaking the sterile seal of the container 10. In one embodiment, one or more chemical indicators may be placed or held in the sterilization chamber 18 and may be viewed through the sleeve 16 to provide an indication of the sterilization processes experienced by the contents of the container 10.

In one embodiment, the sleeve 16 comprises a first region 80, a second region 82 which is disposed discretely from the first region 80 and a third region 84 which is disposed discretely from the second region 82. For the purposes of illustration and discussion, the first region 80 is situated at the front end 40 of the sleeve 16 and the third region 84 is situated at the rear end 42 of the sleeve 16. In one embodiment, the front interface 48 is provided in the sleeve 16 between the first and second regions 80, 82 for engaging the front wall 32 of the frame 12, and the rear interface 46 is provided between the second and third regions 82, 84 for engaging the rear wall 34 of the frame 12. In one embodiment, the container 10 includes a plurality of openings 60 in the top panel 22 of the sleeve 16, a plurality of openings 62 in the bottom panel 24 of the sleeve 16, or pluralities of openings 60, 62 in both the top and bottom panels 22, 24.

In one embodiment, the outer dimensions of the sleeve 16 include a width of approximately 154 mm, a length of approximately 239 mm and a height of approximately 51 mm. In another embodiment, the width of the sleeve 16 may be approximately 77 mm such that two smaller-width sleeves may be stacked or rested on top of a larger width sleeve. In one embodiment, the outer dimensions of the second region 82 are smaller than the outer dimensions of the first and third regions 80, 84. However, it is evident that many alternatives, modifications and variations will be apparent to those skilled in the art in light of the present disclosure. In one embodiment, the thickness of the sleeve 16 in the second region 82 is substantially the same as the thickness of the sleeve 16 in the first region 80 and third region 84.

As illustrated in FIGS. 5(a) and (b), in some embodiments the second region 82 of the sleeve 16 may be smaller in height and width than the first and third regions 80, 84 of the sleeve 16. In one embodiment, the second region 82 is centered laterally and vertically relative to the first and third regions 80, 84. Providing a smaller second region 82 of the sleeve 16 provides room for air and steam to reach the one or more pluralities of openings 60, 62 when the containers 10 are stacked in a sterilization apparatus. The smaller outer dimensions of the second region 82 also allow space for one or more filter assemblies 70 adjacent to the pluralities of openings 60, 62. As described below, the third region 84 need not have the same outer dimensions as the first region 80. Providing regions 80, 84 with similar dimensions allows for containers 10 to be stacked and sit evenly on a surface. Further, providing a second region 82 which is smaller in height and width than the first and third regions 80, 84 allows some flow of steam, air and condensate between containers 10 regardless of their placement in a sterilization apparatus.

Figure 6A:
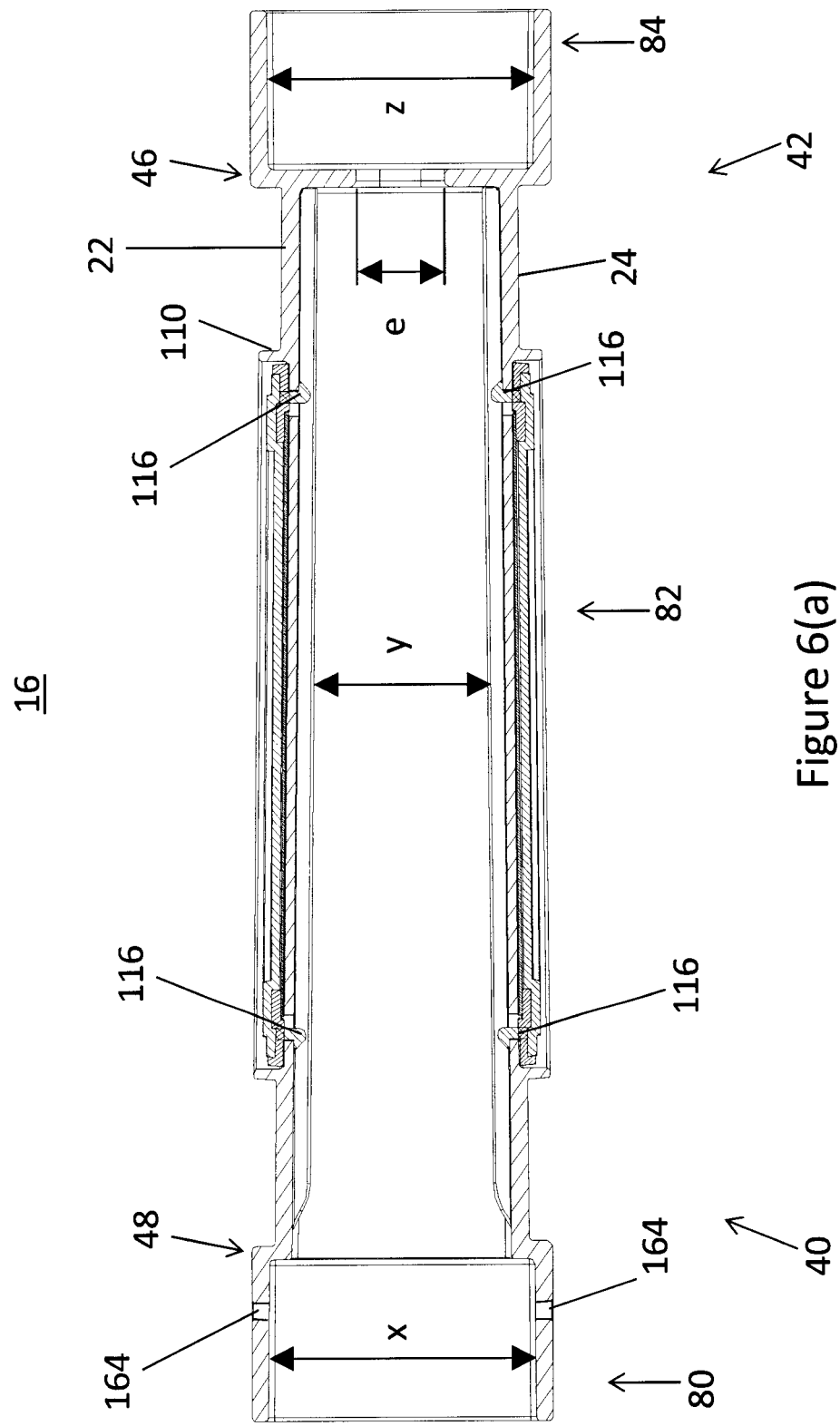
FIG. 6(a) is a longitudinal cross-section view of the sleeve of FIG. 5(a) at line A-A'.

FIGS. 6(a) and (b) illustrate longitudinal and lateral cross-sections of the sleeve 16 of FIG. 5(a). In one embodiment, the top panel 22 and bottom panel 24 in the first region 80 are separated by a first distance "x"; the top panel 22 and bottom panel 24 in the second region 82 are separated by a second distance "y"; and the top panel 22 and bottom panel 24 in the third region 84 are separated by a third distance "z". In one embodiment, the distances "x" and "z" are approximately equal.

Figure 6B:
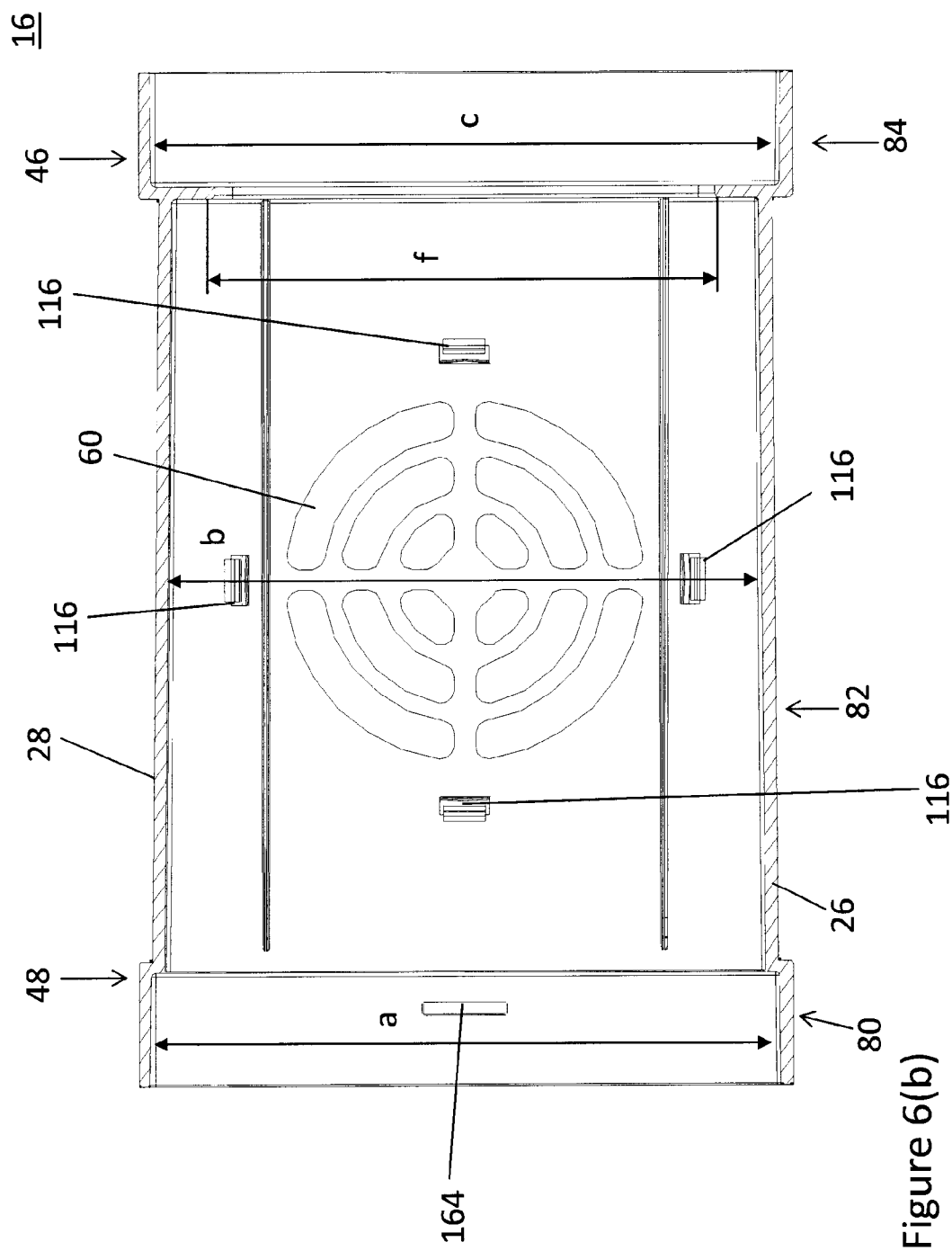
FIG. 6(b) is a lateral cross-section view of the sleeve of FIG. 5(a) at line B-B'.

Similarly, as shown in FIG. 6(b), in one embodiment the first side panel 26 and second side panel 28 in the first region 80 are separated by a first distance "a"; the first side panel 26 and second side panel 28 in the second region 82 are separated by a second distance "b"; and the first side panel 26 and second side panel 28 in the third region 84 are separated by a third distance "c".

In one embodiment, the distance "x" is greater than the distance "y", and the distance "a" is greater than the distance "b", thereby forming the front interface 48 in the transition between the first and second regions 80, 82. In one embodiment, the front interface 48 is formed by a transition between the top panel 22, bottom panel 24 and first and second side panels 26, 28 of the first region 80 and the respective top panel 22, bottom panel 24 and first and second side panels 26, 28 of the second region 82. In some embodiments, the front interface 48 comprises portions of the top panel 22, bottom panel 24 and first and second side panels 26, 28 between the first region 80 and the second region 82 which are disposed generally perpendicularly to and outwardly from the top panel 22, bottom panel 24 and first and second side panels 26, 28 of the second region 82. As shown in FIGS. 6(a) and (b), in this embodiment, the front interface 48 has a stepped cross-section at the transitions between the top panels and bottom panels 22, 24 (as shown) and also at the transitions between the respective first and second side panels 26, 28. In other embodiments, the portions of the top panel 22, bottom panel 24 and first and second side panels 26, 28 between the first region 80 and the second region 82 may be configured at different angles or may comprise a curved or curvilinear cross section. In some embodiments, the front interface 48 comprises equal portions or extensions of the top panel 22, bottom panel 24, first side panel 26 and second side panel 28.

In another embodiment (not shown), the distances between the top and bottom panels 22, 24 in the first, second and third regions 80, 82, 84 may be the same, and the distances between the side panels 26, 28 in the first, second and third regions 80, 82, 84 may be the same. In this embodiment, the front interface 48 comprises portions of the top panel 22, the bottom panel 24, the first side panel 26, the second side panel 28, or combinations thereof, which extend inwardly towards the cavity 30 between the first and second regions 80, 82. In this embodiment, the distance "x" need not be greater than the distance "y" and the distance "a" need not be greater than the distance "b". In one embodiment, the portions of the top panel 22, the bottom panel 24, the first side panel 26, the second side panel 28 or combinations thereof, extend inwardly and generally perpendicularly from the top, bottom, and first and second side panels 22, 24, 26, 28. In another embodiment, the portions of the top panel 22, the bottom panel 24, the first side panel 26, the second side panel 28, or combinations thereof, may extend inwardly at different angles or may comprise a curved or curvilinear longitudinal cross section.

In another embodiment, the front interface 48 comprises a front panel (not shown) disposed transversely across the sleeve 16 between the first and second regions 80, 82. The front panel may be mounted to the interior of the sleeve 16 or to portions of the sleeve 16 which extend inwardly into the cavity 30. The front panel includes an opening to allow a portion of the frame 12 to pass through the front panel to the cavity 30 of the sleeve 16 between the second and third regions 82, 84. A portion of the front wall 32 of the frame 12 remains in the first region 80 and engages the front panel. A front seal 50 may be placed between the front wall 32 and the front interface 48.

FIGS. 7(a) and 7(b) illustrate one embodiment in which a first surface 94 of the front interface 48 faces towards the first region 80 for engagement with the front wall 32 of the frame 12. The front interface 48 extends around the interior perimeter of the sleeve 16 between the first and second regions 80, 82. In one embodiment, the first surface 94 of the front interface 48 is approximately 2.4 mm wide. In other embodiments, multiple surfaces of the front interface 48 may face in one or more directions towards the first region 80 for engagement with the front wall 32 of the frame 12.

In one embodiment, as seen in FIGS. 3, 6 and 7, the rear interface 46 is comprised of one or more portions of the top panel 22, the bottom panel 24, the first side panel 26 or the second side panel 28, or combinations thereof, which extend inwardly towards the cavity 30 between the second and third regions 82, 84. In one embodiment, the portions of the top panel 22, the bottom panel 24, the first side panel 26, the second side panel 28 or combinations thereof, extend inwardly and generally perpendicularly from the top, bottom, and first and second side panels 22, 24, 26, 28. In another embodiment, the portions of the top panel 22, the bottom panel 24, the first side panel 26, the second side panel 28 or combinations thereof, extend inwardly at different angles or may comprise a curved or curvilinear longitudinal cross section.

In one embodiment, the rear interface 46 comprises a rear panel (not shown) disposed transversely across the sleeve 16 between the second and third regions 82, 84. The rear panel may be mounted to the interior of the sleeve 16 or to portions of the sleeve 16 which extend inwardly into the cavity 30. The rear panel includes an opening to allow a portion of the rear wall 34 of the frame 12 to extend between the second and third regions 82, 84 or to extend into the third region 84. A portion of the rear wall 34 of the frame 12 remains in the second region 82 and engages the rear panel. A rear seal 52 may be placed between the rear wall 34 and the rear interface 46.

In one embodiment, the rear interface 46 reduces the height and width of the cavity 30 of the sleeve 16 between the second and third regions 82, 84 of the sleeve 16 indicated as height "e" in FIG. 6(a) and width "f" in FIG. 6(b). In one embodiment, the height "e" is approximately 15 mm and the width "f" is approximately 118 mm. As shown in FIG. 3, the height of the portion which extends from the bottom panel 24 may be greater than the height of the portion which extends from the top panel 22. Alternatively, the height of portions which extend from the top panel 22, the bottom panel 24, the first side panel 26 and the second side panel 28 may be approximately equal as shown in. FIGS. 6(a) and (b) and FIGS. 7(a) and 7(b). When the frame 12 is inserted in the sleeve 16, the rear interface 46 prevents the frame 12 from being inserted entirely through the second region 82 into the third region 84. A portion of the rear wall 34 of the frame 12 may extend between the second and third regions 82, 84 or into the third region 84.

In one embodiment, as illustrated in FIGS. 7(a) and (b), a first surface 98 of the rear interface 46 faces towards the second region 82 for engagement with the rear wall 34 of the frame 12. The rear interface 46 and first surface 98 extend around the interior perimeter of the sleeve 16 between the second and third regions 82, 84. In one embodiment, the first surface 98 of the rear interface 46 is approximately 138 mm wide. In other embodiments, multiple surfaces of the rear interface 46 may face in one or more directions towards the second region 82 for engagement with the front wall of the frame 12.

As shown in FIG. 6, in one embodiment the rear end 42 of the sleeve 16 also includes a transition between the top panel 22, bottom panel 24 and first and second side panels 26, 28 of the third region 84 and the respective top panel 22, bottom panel and first and second side panels 26, 28 of the second region 82, similar to transitions between panels in the first and second regions 80, 82 for one embodiment of the sleeve 16. In one embodiment, the distance "z" is equal to the distance "x" and the distance "c" is equal to the distance "a" in order to provide the third region 84 of the sleeve 16 with a size similar or symmetrical to the first region 80. In other embodiments, the distance "z" between the top and bottom panel of the third region 84 is the same as the distance "y" between the top and bottom panel of the second region 82; and the distance "c" between the side panels 26, 28 of the third region 84 is the same as the distance "b" between the side panels 26, 28 of the second region 82.

As illustrated in FIGS. 7(a) and (b), the sleeve 16 may include one or more rails 100 disposed on an interior surface of the top panel 22, the bottom panel 24, the first and second side panels 26, 28, or combinations thereof, to guide the insertion and alignment of the frame 12 in the sleeve 16. The one or more rails 100 also provide for some displacement between the frame 12 and the sleeve 16. The one or more rails 100 may allow for the passage of air and steam during the sterilization process. The one or more rails 100 may separate the frame 12 from the one or more filter assemblies 70.

FIG. 3(a) illustrates a longitudinal cross-section of a container 10 in accordance with the present disclosure and the engagement between the frame 12 and the sleeve 16 in one embodiment. The frame 12 is generally sized to pass through the first region 80 of the sleeve 16 and fit within the cavity 30 in the second region 82 of the sleeve 16 with the height and width of the frame 12 being less than the height and width of the cavity 30 in the second region 82. When the frame 12 is slid or inserted into the sleeve 16, a portion of the rear wall 34 of the frame 12 rests adjacent to or engages the rear interface 46. The rear seal 52 may be disposed between the rear wall 34 of the frame 12 and the rear interface 46. In one embodiment, the rear seal 52 is part of or is affixed to the rear wall 34. In another embodiment, the rear seal 52 is affixed to or is part of the rear interface 46 of the sleeve 16. The rear seal 52 may be comprised of seals on both the rear wall 34 and rear interface 46. As shown in FIG. 7, a portion of the rear wall 34 of the frame 12 may extend between the second and third regions 82, 84 or into the third region 84 of the sleeve 16.

A portion of the front wall 32 of the frame 12 rests adjacent to or engages the front interface 48. A portion of the front wall 32 of the frame 12 is sized larger than the front interface 48 such that the portion of the front wall 32 of the frame 12 does not pass through the front interface 48 into the cavity 30 in the second region 82. The front seal 50 may be placed between the front wall 32 and the front interface 48. In one embodiment, the front seal 50 is part of or affixed to the front wall 32. In another embodiment, the front seal 50 is affixed to or, is part of the front interface 48, or the front seal 50 may be comprised of seals on both the front wall 32 and front interface 48.

Figure 8:
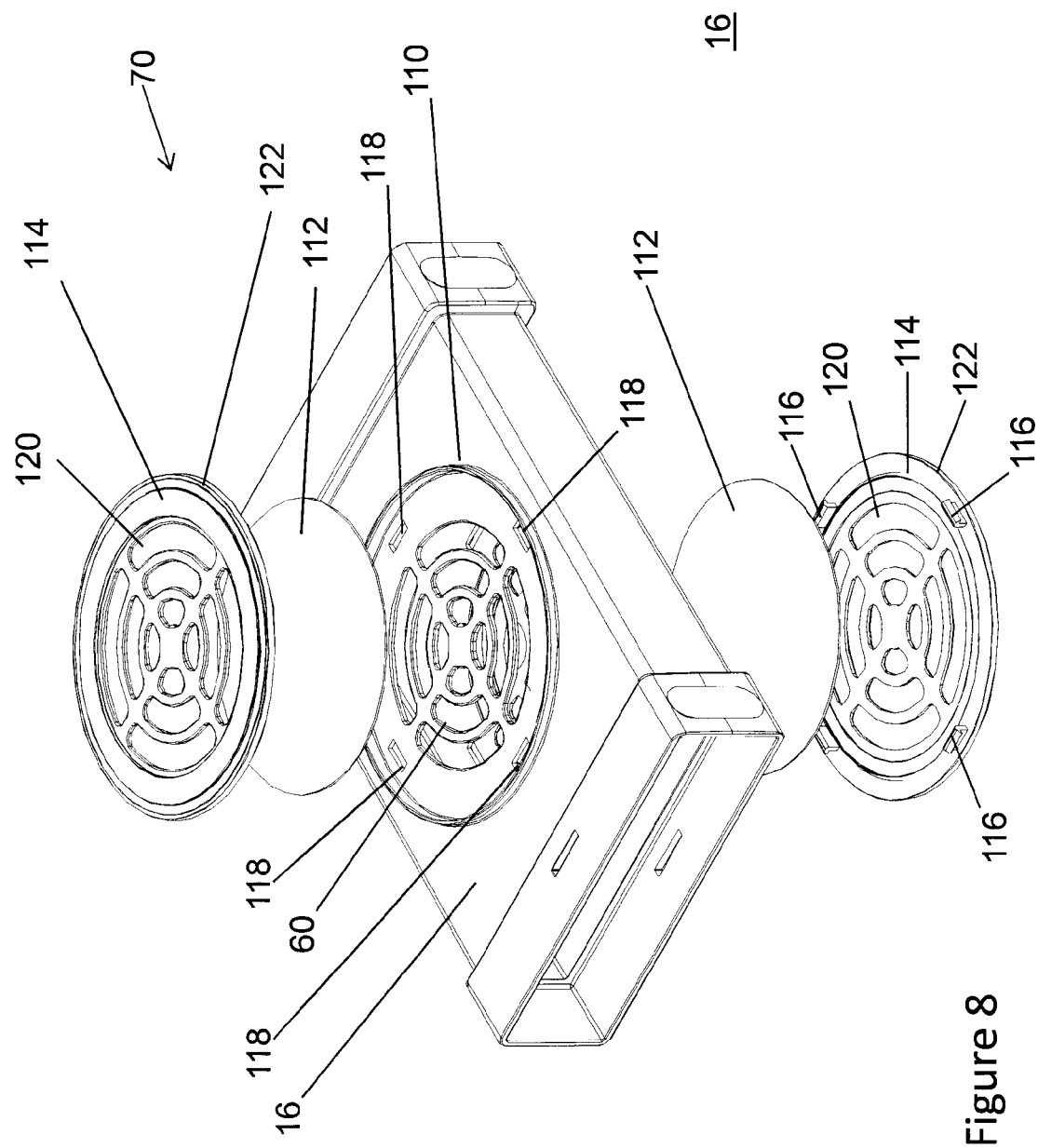
FIG. 8 is an exploded view of a sleeve in accordance with an embodiment of the present disclosure.

FIG. 8 illustrates a sleeve 16 with a filter assembly 70 in accordance with one embodiment of the present disclosure. The sleeve 16 is configured with a plurality of openings 60 in the top panel 22. The sleeve 16 includes a base 110 for receiving the filter assembly 70. In one embodiment, the base 110 is formed as part of the top panel 22 of the sleeve 16 and comprises a wall extending outwardly from the top panel 22 and around the plurality of openings 60. The filter assembly 70 includes a filter layer 112 and a retainer 114 to hold the filter layer 112 within the assembly 70 and to the sleeve 16.

One or more attachment mechanisms may be used to hold the retainer 114 and filter layer 112 in place in the base 110. In one embodiment illustrated in FIGS. 5, 6 and 8, the retainer 114 includes one or more snap tabs 116 which mate with one or more corresponding slots 118 in the top panel 22 of the sleeve 16 as shown in FIG. 8. The snap tabs 116 may comprise a hooked end which flexes to allow the retainer 114 to be placed over and locked with the top panel 22. The hooked end engages an interior surface of the top panel 22 to prevent the retainer 114 and filter layer 112 from becoming dislodged. In one embodiment, the retainer 114 is removed from the sleeve 16 by moving the hooked end of the snap tab 116 from within the cavity 30 of the sleeve 16 in order to free the snap tab 116 from the slot. A similar filter assembly 70 may be provided adjacent to the plurality of openings in the bottom panel 24.

The retainer 114 includes a plurality of openings 120 corresponding in surface area to the plurality of openings 60 in the sleeve 16 in order to allow for communication of steam between the sterilization chamber 18 and the sterilization apparatus. In one embodiment, the retainer 114, snap tabs 116 and slots 118 may be configured to ensure alignment of the openings 120 in the retainer 114 with the openings 60 in the top panel 22 when the filter assembly 70 is fit in place.

The retainer 114 is comprised of plastic material which provides some flex for the snap tabs 116 to engage slots 118, such as the slots 118 in the top panel 22 or bottom panel 24 as described above. In one embodiment, the retainer 114 comprises a plastic material such as polyether ether ketone (PEEK). Since the retainer 114 may be readily replaced, it need not comprise a material which can withstand the same number and duration of sterilization cycles as the sleeve 16. In one embodiment, the filter assembly 70 and retainer 114 include a filter seal 122. The filter seal 122 may comprise a ring of sealing material adjacent to the retainer 114 and the sleeve 16. In one embodiment, the filter seal 122 is comprised of silicone and may be formed with the retainer 114 as an overmoulding from an injection moulding process.

The filter layer 112 comprises a layer of material which is permeable to gas and steam which enter through the pluralities of openings 120, 60 in the retainer 114 and top panel 22, but blocks the entry of germs, bacteria and other contaminants. The filter layer 112 may comprise a semi-permanent filter made from material such as Polytetrafluoroethylene (PTFE) which may be used for numerous sterilization cycles. The filter layer 112 also may comprise disposable or single use filter material such as paper-based filters. In one embodiment (not shown) a filter assembly 70 is not provided and the pluralities of openings 120 may be configured to define one or more tortuous paths between the environment of the container and the sterilization chamber 18 to limit the entry of bacteria. In other embodiments, a combination of a filter assembly 70 and tortuous path configurations for the pluralities of openings 120 may be used.

The pluralities of openings 60 in the sleeve 16 and filter assembly 70 also may be configured in shapes and locations other than the circular and centered configuration shown in the figures. In one embodiment, one or more pluralities of openings 60 and filter assemblies 70 are provided in one or both of the first and second side panels 26, 28.

FIGS. 9(a) to (g) illustrate further embodiments of a sleeve 1016 in accordance with the present disclosure. In some embodiments, the sleeve 1016 includes one or more notches 9003 in one or both the top panel 22 and bottom panel 24, in one or both of the first and third regions 80, 84. The notches 9003 may be of various shapes such as, but not limited to, a curved or concave shape as illustrated. The notches 9003 may be located adjacent the knob 160 and rear handle 1003 when the sleeve 1016 and frame 12 are assembled in the first configuration of the container 1000 to improve access to the knob 160 and rear handle 1003. In some embodiments, the notches 9003 allow provide for additional draining of condensate during the sterilization process.

The sleeve 1016 includes a filter assembly 1070 similar to the filter assembly 70 described above, including a base 1110 formed as part of the top panel 22 of the sleeve 1016 and comprises a wall extending outwardly from the top panel 22 and around a plurality of openings 1060 in the sleeve 1016. In one embodiment, the filter assembly 1070 includes a retainer 1114 and filter layer 1112 to hold the filter layer 1112 within the assembly 1070 and to the sleeve 1016. In one embodiment, the retainer 1114 includes two pairs of snap tabs 1116 which mate with one or more corresponding vertical ribs 9011 in the sleeve 1016. The pairs of snap tabs may be spaced apart such that a user typically must use two hands to unlatch the filter retainer 1114, thus reducing the likelihood of a user accidentally removing the filter retainer 1114 and accidentally comprising load sterility.

Figure 9A:
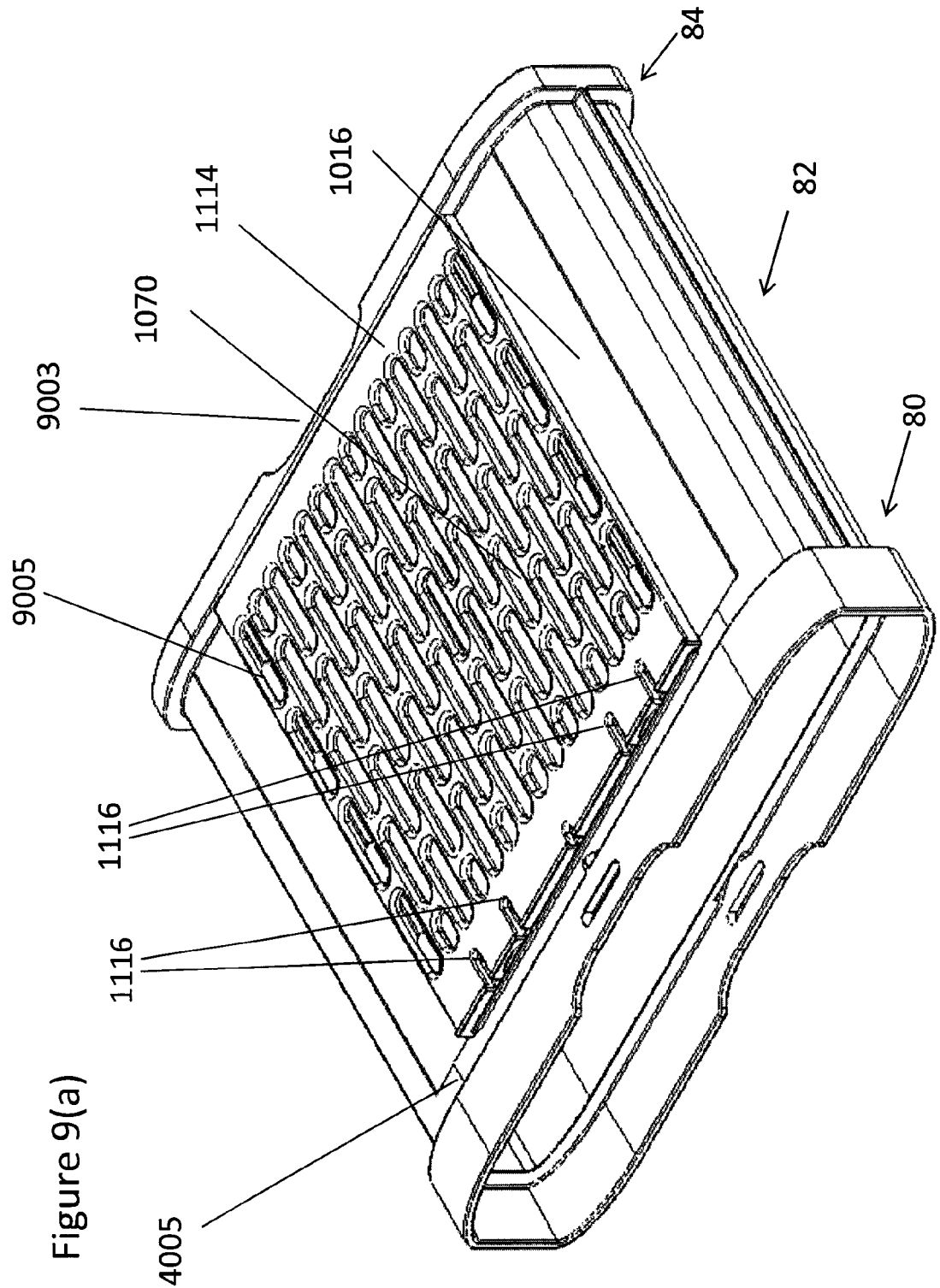
FIGS. 9(a) and (b) are front-top isometric views of a sleeve in accordance with an embodiment of the present disclosure.
Figures 9B, 9C:
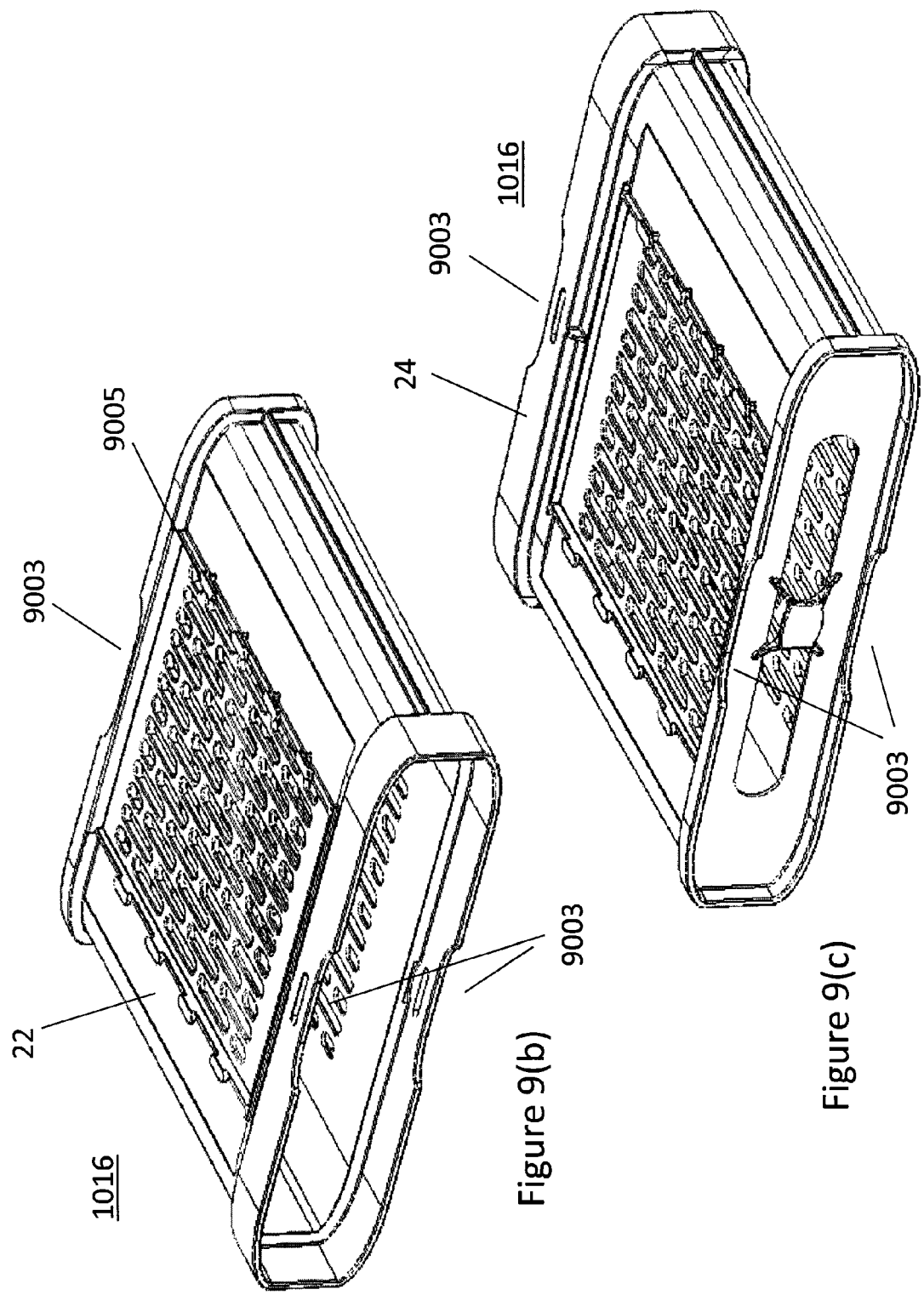
FIG. 9(c) is a rear-bottom isometric view of a sleeve in accordance with an embodiment of the present disclosure.
Figure 9:
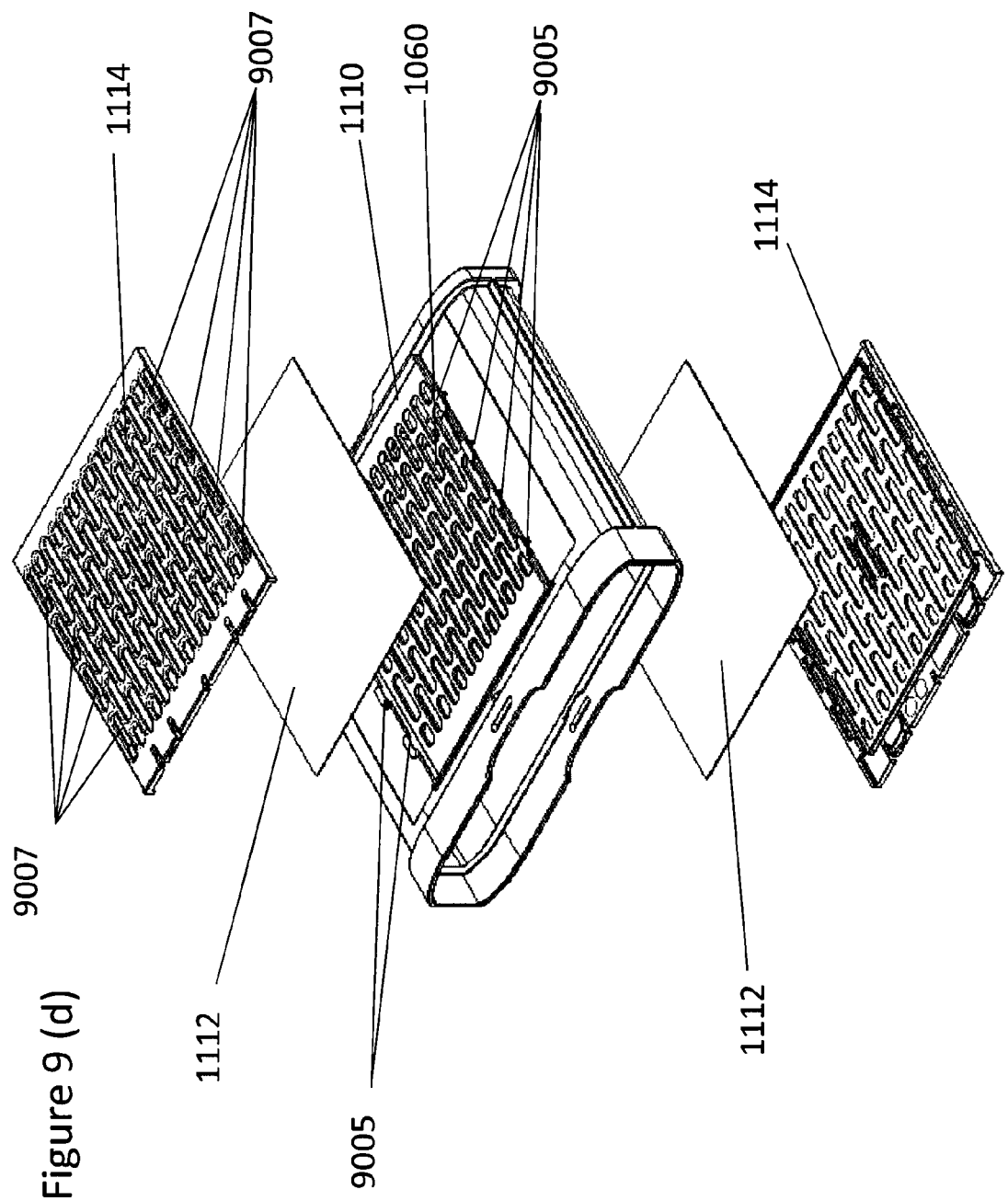
FIG. 9(d) is an exploded view of a sleeve in accordance with an embodiment of the present disclosure.
FIG. 9(e) is a top view of a sleeve in accordance with an embodiment of the present disclosure.
FIG. 9(f) is a longitudinal cross-section view of the sleeve at line C-C' of FIG. 9(e)
FIG. 9(g) is a longitudinal cross-section view of the sleeve at line D-D' of FIG. 9(e), FIG. 9(h) provides longitudinal cross-section views of a sleeve in accordance with an embodiment of the present disclosure.
FIG. 9(i) is a view of a front portion of a frame.
FIG. 9(j) is a sectional view of the sleeve of FIG. 9(a)
FIG. 9(k) is a sectional view of another embodiment of the sleeve according to the present disclosure, FIGS. 9(l) and (m) are close-up, side sectional views of a portion of a container in accordance with the embodiment shown in FIG. 9(k)
FIG. 9(n) is an exploded view of a sleeve in accordance with an embodiment of the present disclosure.
Figure 9E:
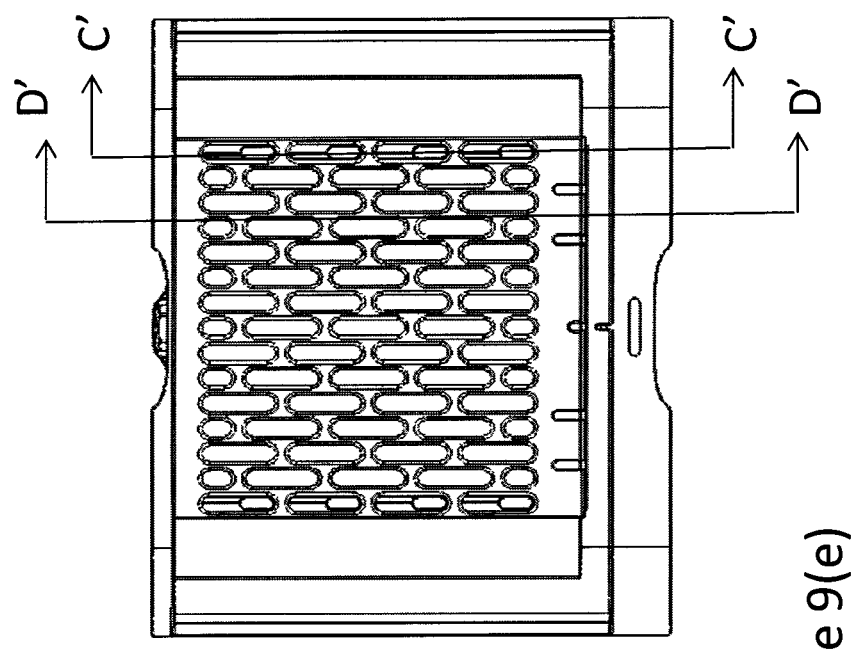

In some embodiments, the filter assembly 1070 includes a plurality of tabs 9005 in the base 1110 of the filter assembly 1070 and corresponding tabs 9007 in the retainer 1114 as identified in FIGS. 9(a) and (d) to (g). In one embodiment, four tabs 9005 and four tabs 9007 are provided and spaced over side edges of the respective base 1110 and retainer 1114. In one embodiment, once the filter layer 1112 is placed on the base 1110, the retainer 1114 may be placed over the filter layer 1112 adjacent the first region 80 of the sleeve 1016. As shown in FIG. 9(g), the tabs 9007 are of the retainer 1114 are accepted through corresponding slots in the base 1110. As the retainer 1114 is moved towards the third region 84, the tabs 9007 of the retainer 1114 slide under the corresponding tabs 9005 in the base 1110 to lock the filter layer 1112 and filter retainer 1114 in place. In some embodiments, one or more snaps 9009 on the filter retainer 1114 are stopped by one or more vertical ribs 9011 on the base 1110. In order for the retainer 1114 to be removed, the retainer 1114 and snap 9009 are lifted to clear the rib 9011 and allow the retainer 1114 to be pulled forward for removal.

Figure 9H:
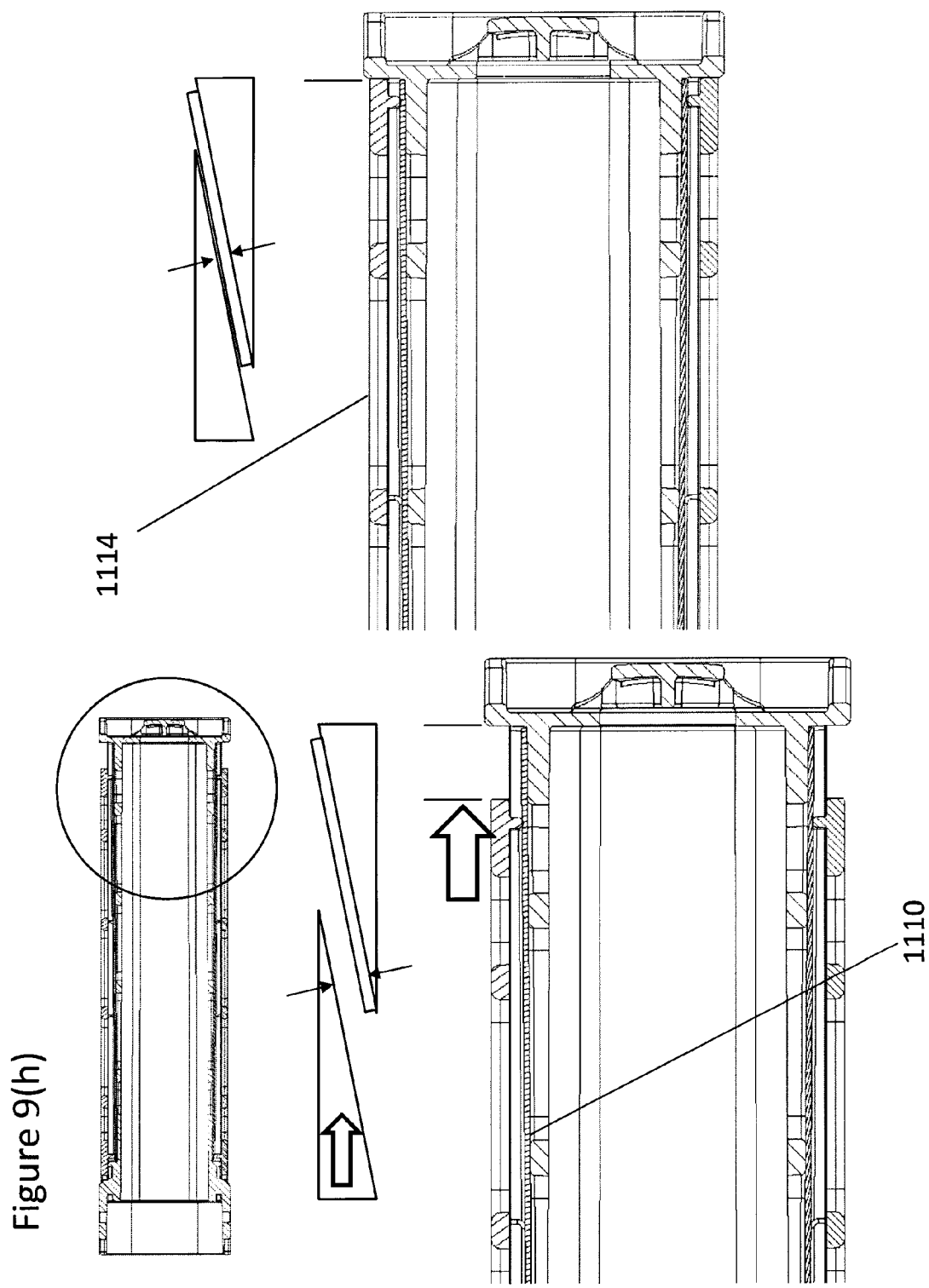

In one embodiment, as illustrated in FIG. 9(h), a surface of the base 1110 of the filter assembly 1070 has a slight gradient and a surface of the retainer 1114 has a corresponding complementary gradient, which is shown enlarged and exaggerated in FIG. 9(h). As the retainer 1114 is placed over the base 1110 and slid towards the third region 84 to lock the filter assembly 1070, the filter layer 1112 is gradually pressed against the surface of the base 1110 in order to eliminate any gap for air and steam to pass through between the filter layer 1112 and the base 1110.

In one embodiment, the sleeve 1016 includes one or more recesses 9009 in the front interface 48 of the sleeve 1016 for receiving projections 9011 provided in a front wall 32 of a frame 1012. As shown in FIGS. 9(i) and 9(j), the projections 9011 may comprise one or more tongues extending laterally from the front wall 1032 of the frame 1012 towards the second region 1082 of the sleeve 1016. The corresponding recesses 9009 engage with the projections 9011 to ensure proper alignment and engagement of the front wall 32, front interface 48 and front seal 50.

Figure 9K:
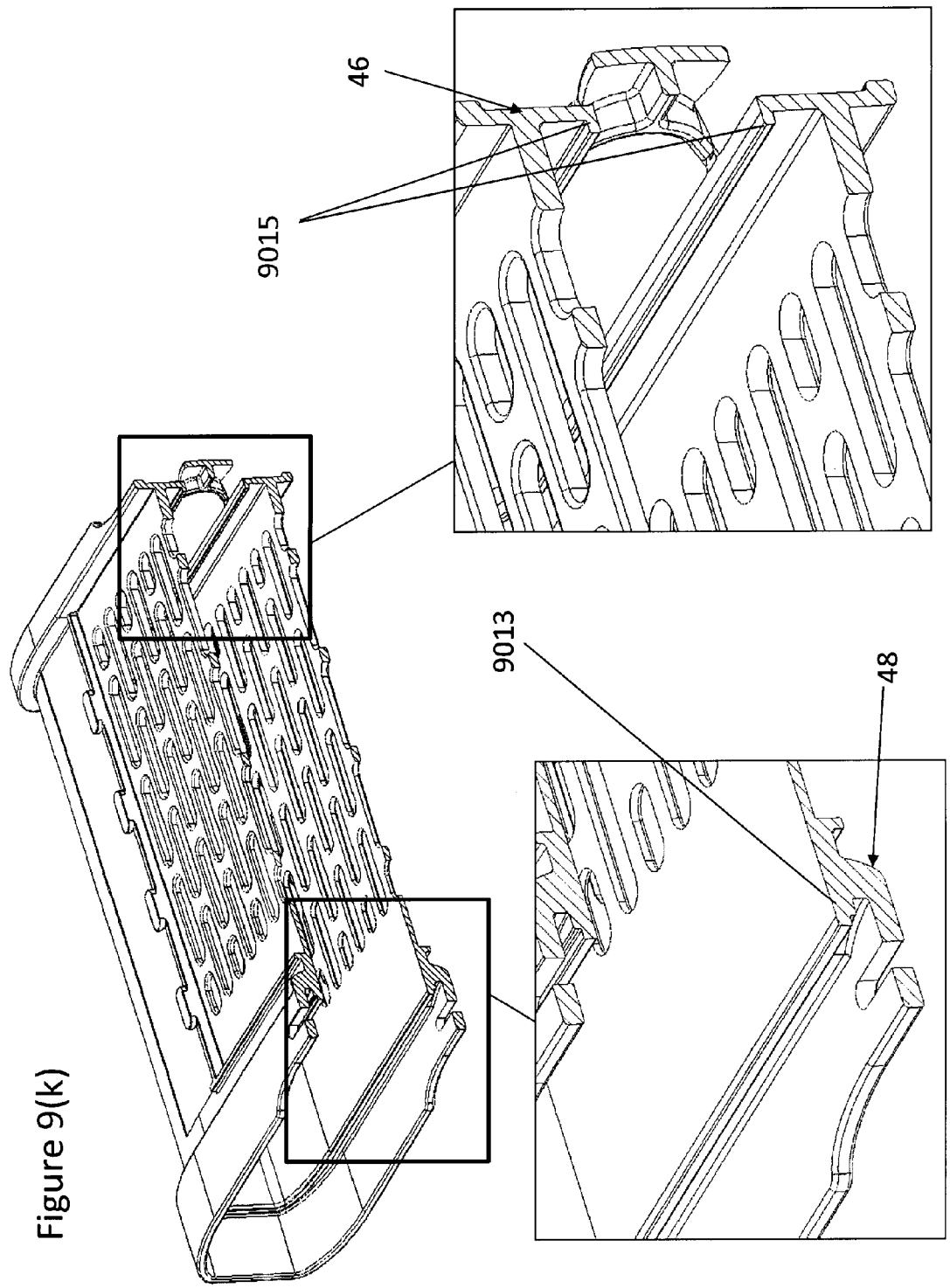
Figure 9L:
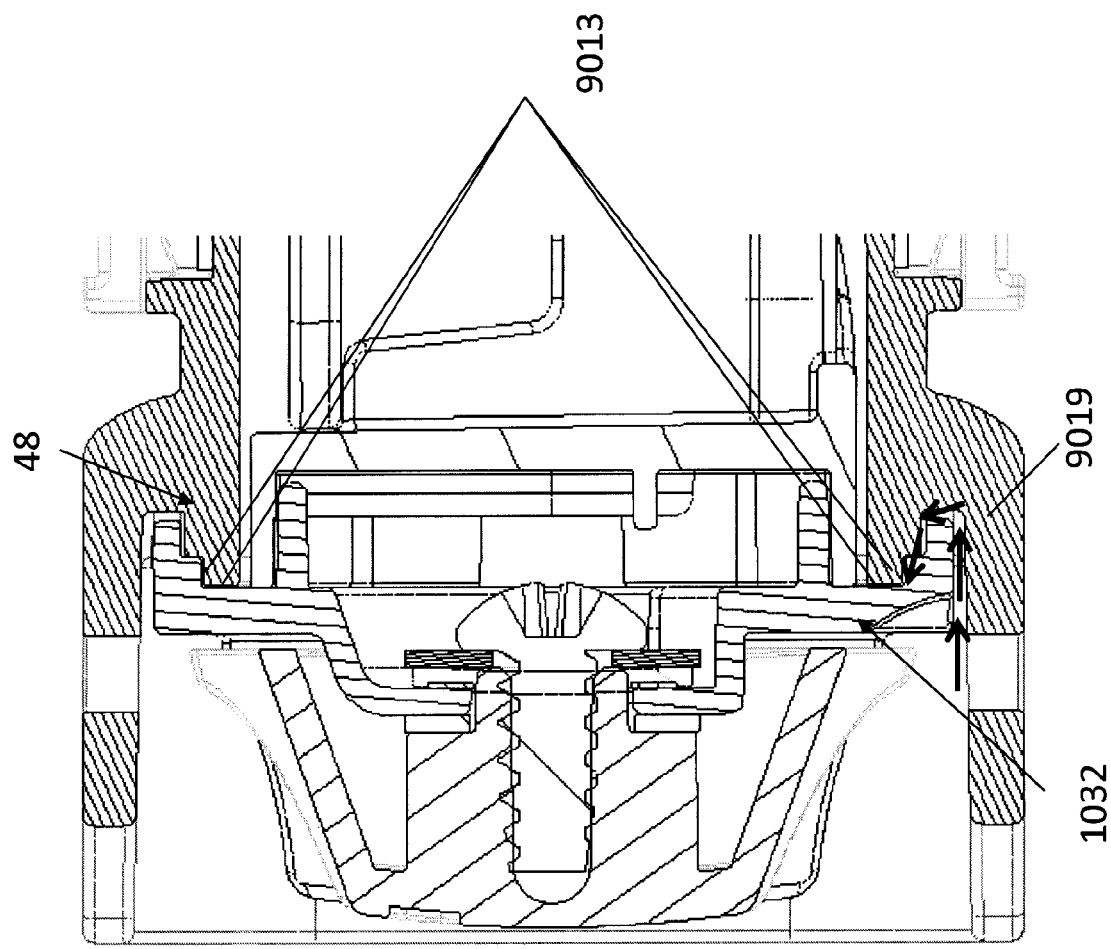

As described above with respect to FIGS. 3(a) and 3(b), the container 10, 1000 may include a front seal 50, 1050 and a rear seal 52, 1052 at the respective front and rear interfaces 48, 46, or one or more tortuous paths at the front and rear interfaces 48, 46, or a combination of seals and tortuous path configurations to inhibit the entrance and travel of bacteria into the container 10, 1000 and sterilization chamber 18. In some embodiments, the sleeve 1016 includes a rib 9013 in the front interface 48 which projects slightly from the front interface 48 towards the first region 80 of the sleeve 1016 and defines a channel for receiving the front wall 1032 of the frame 1012. Similarly, the sleeve 1016 may include a rib 9015 in the rear interface 46 which projects slightly from the rear interface 46 towards the second region 82 of the sleeve 1016 and defines a channel for receiving the rear wall 1034 of the frame 1012. As illustrated in FIGS. 9(k), 9(l) and 9(m), the ribs 9013, 9015 may configured in a stepped fashion or with other variations in the geometry and contour of the ribs 9013, 9015 in order to create tortuous paths 9019, 9021 at the interfaces between the frame 12, 1012 and the sleeve 16, 1016.

Figure 9N:
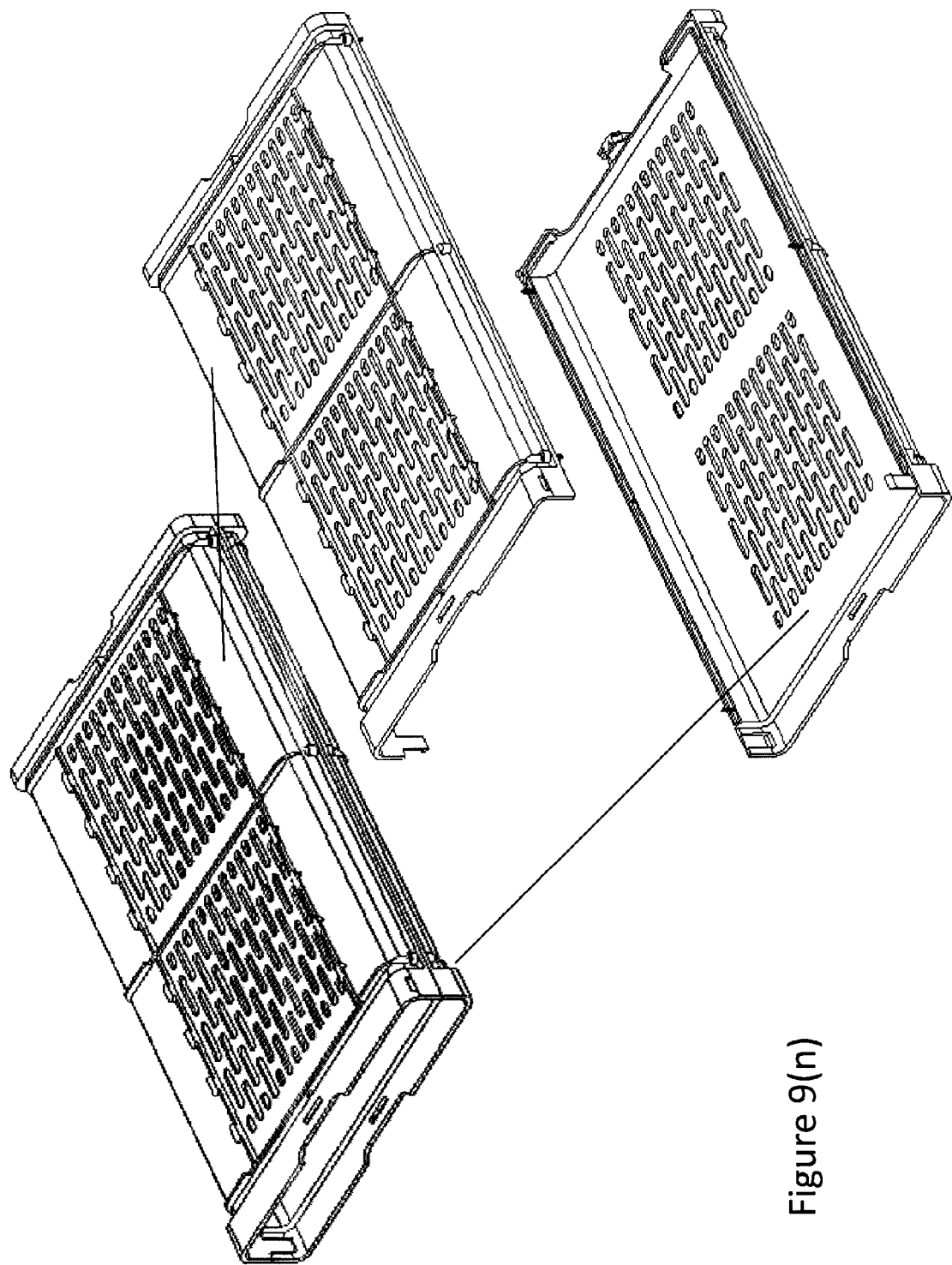

The sleeve 1016 may be constructed from one or more individual panels or constructed as one piece. The sleeve 1016 may be provided in different sizes and may be moulded from one or more parts. In one embodiment, as illustrated in FIG. 9(n), a larger-sized sleeve is constructed from top and bottom portions of the same injection-moulded part. In another embodiment, a larger-sized sleeve is assembled from the components for two smaller sized sleeves, such as with two filter assemblies 1070 as illustrated in FIGS. 9(a) to (f).

FIGS. 10(a), (b) and 11 illustrate a first embodiment of a frame 12 in accordance with the present disclosure. As described above, in one embodiment, the frame 12 includes a front wall 32 and a rear wall 34 which are joined by first and second side walls 36, 38. The frame 12 is adapted to hold one or more articles for sterilization, such as medical or dental instruments. In one embodiment, the frame 12 includes one or more members 72 which extend laterally, longitudinally, or both laterally and longitudinally across the frame 12. The members 72 may provide structural support for the frame 12. The members 72 may be situated at the bottom of the walls of the frame 12 to provide support for the articles received in the frame 12. In one embodiment, as seen for example in FIG. 10, the frame 12 may include one or more members 72 adjacent to a bottom portion of each of the front, rear and first and second side walls. The members 72 may comprise bottom portions 72a to 72d of the front, rear and first and second side walls extending horizontally within the interior of the frame 12 to add support or stability for the frame 12. In some embodiments, the frame 12 is comprised of a plastic material such as polyphenylene sulfide (PPS) or polyether ether ketone (PEEK) or a metal material such as stainless steel.

In one embodiment, the frame 12 includes one or more spacers 74 which are adapted to receive instruments for washing and sterilization and to maintain space between the instruments to allow for the passage of water, steam and air around the instruments during the washing and sterilization processes. In one embodiment, the spacers 74 are molded as part of the frame 12.

The frame 12 may include one or more handles, such as a handle 132, mounted to the first side wall 36 and the second side wall 38 adjacent to the front wall 32 and a handle 134 mounted to the first side wall 36 and the second side wall 38 adjacent to the rear wall 34. The handles 132, 134 are pivotally attached to the side walls 36, 38. In one embodiment of the frame 12, the handles 132, 134 are snapped into place by flexing the handles 132, 134 slightly so that pivot pins in the handles 132, 134 enter corresponding pivot holes in the frame 12. The handles 132, 134 also may be comprised of a plastic material such as PPS. In one embodiment, the handles 132, 134 are configured in a first position and are contained within an interior 136 of the frame 12. The handles 132, 134 may rest on or adjacent to one or more spacers 74 to retain or secure the instruments held or resting within the spacer 74. When the frame 12 is not contained within the sleeve 16, the handles 132, 134 may be moved to a second position wherein the handles 132, 134 extend outwardly from the frame 12 as illustrated in FIG. 4. The handles 132, 134 may be used in the second position to move the frame 12 and instruments contained therein. Adjusting the handles 132, 134 to the second position also allows for access to the instruments contained in the frame 12.

The frame 12 also may include one or more openings 135 in one or both of the first and second side walls 36, 38. The openings 135 may be made within the frame 12 to allow colour coded buttons (not shown) to be inserted into the openings 135 to facilitate identification of instruments in the frame 12. In some embodiments, the colour coded buttons are visible through the transparent or semi-transparent sleeve 16 of the container 10.

Figure 11:
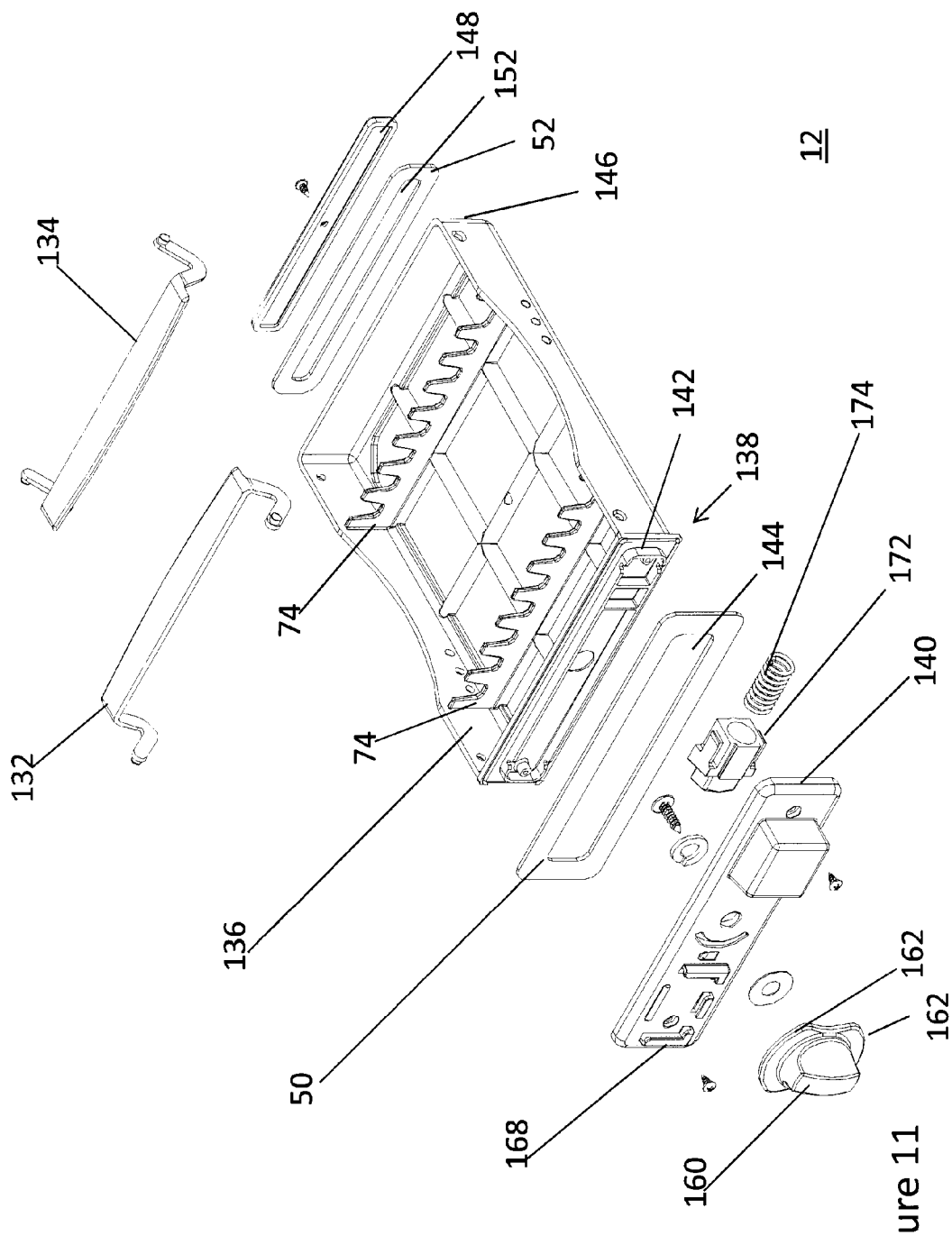
FIG. 11 is an exploded view of the frame of FIGS. 10(a) and (b)

As illustrated in FIG. 11, each of the front wall 32 and rear wall 34 comprises a number of components. In one embodiment, the front wall 32 includes a front base 138 and a front plate 140. The front base 138 is adapted to receive the front seal 50 which is held between the front plate 140 and the front base 138. In one embodiment, the front base 138 is formed as an integral part of the frame 12. The front seal 50 may be comprised of a silicone material such as a 1/16" thick layer of silicone. In one embodiment, the front seal 50 has a height and width slightly larger than the front base 138 so that a portion of the front seal 50 extends beyond the front base 138 and is exposed for engagement with the sleeve 16. The front seal 50 may comprise a bulb seal which engages the front interface 48 and is further compressed as the rear wall 34 of the frame 12 engages the rear interface 46 of the sleeve 16. In one embodiment, the front base 138 includes a front bracket 142 which is adapted to receive the front seal 50 and retain the front seal 50 for engagement with the front interface 48. In one embodiment, the front bracket 142 comprises a wall extending transversely from the front base 138 and extending around a perimeter of the front base 138. The front seal 50 is configured to be stretched around or retained by the front bracket 142. In one embodiment, the front seal 50 has a rectangular or rounded rectangular hole 144 so that the front seal 50 may be placed over and rest on or around a corresponding rectangular or rounded rectangular front bracket 142. The front plate 140 may be affixed to the front base 138 by one or more screws which mate with one or more threaded cavities in the front bracket 142 or the front base 138.

Figure 12:
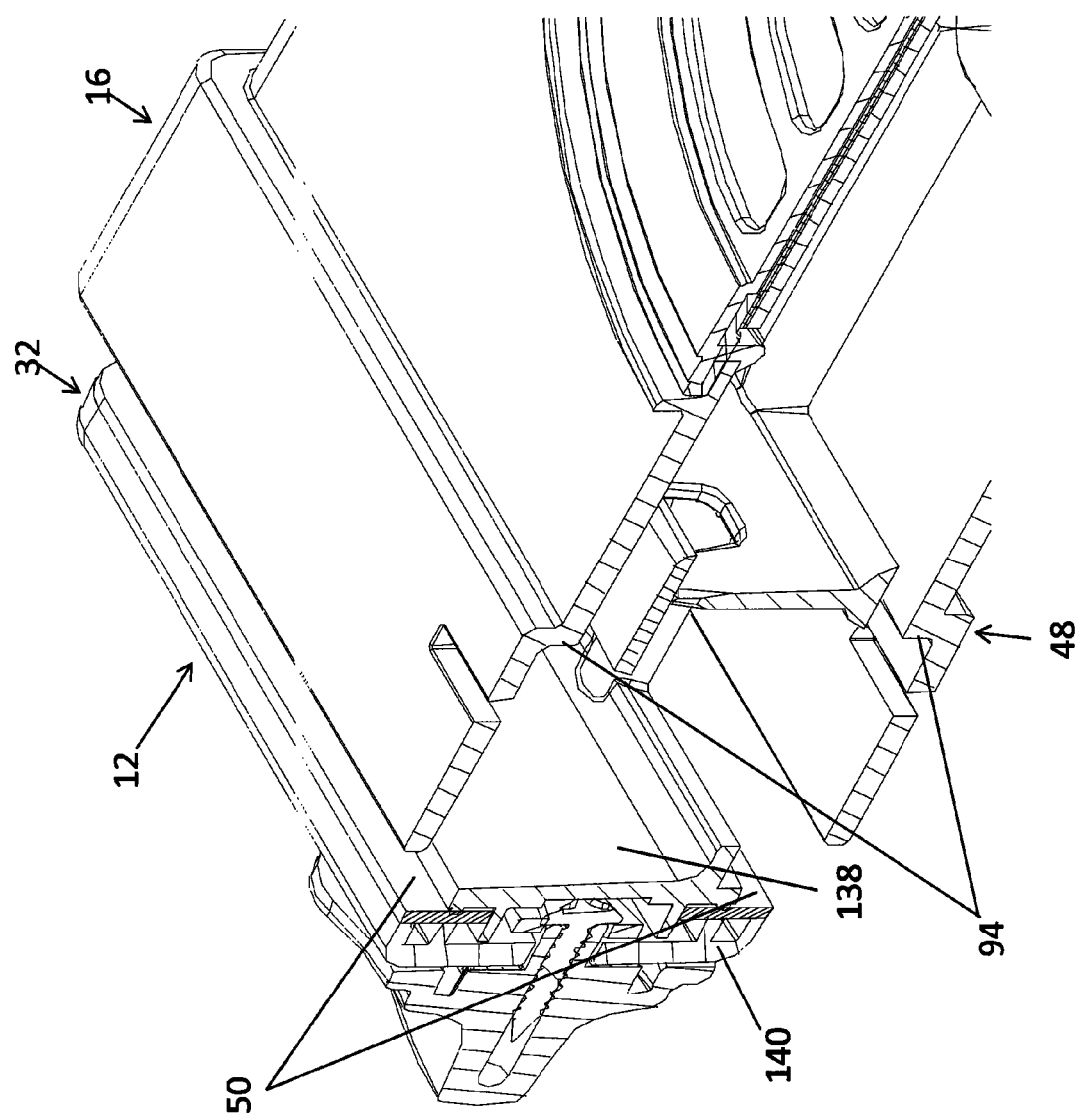
FIG. 12 is a sectional view of a front portion of a frame partially inserted in a sleeve in accordance with an embodiment of the present disclosure.

FIG. 12 illustrates a sectional view of a container 10 showing the frame 12 partially inserted in the sleeve 16 and showing a rear view of the front wall 32. A portion of the front seal 50 is exposed for engagement with the first surface 94 of the front interface 48 when the frame 12 is fully inserted in the sleeve 16. In one embodiment, the front plate 140 has a length and height approximately the same as the front seal 50. When the frame 12 is fully inserted in the sleeve 16, the front plate 140 provides support for, and biases the front seal 50 against, the front interface 48. As shown in FIG. 12, the front seal 50 extends above and below the front base 138 of the front wall 32. The front seal 50 also may extend beyond the first and second side walls 36, 38 of the frame 12.

Figure 14:
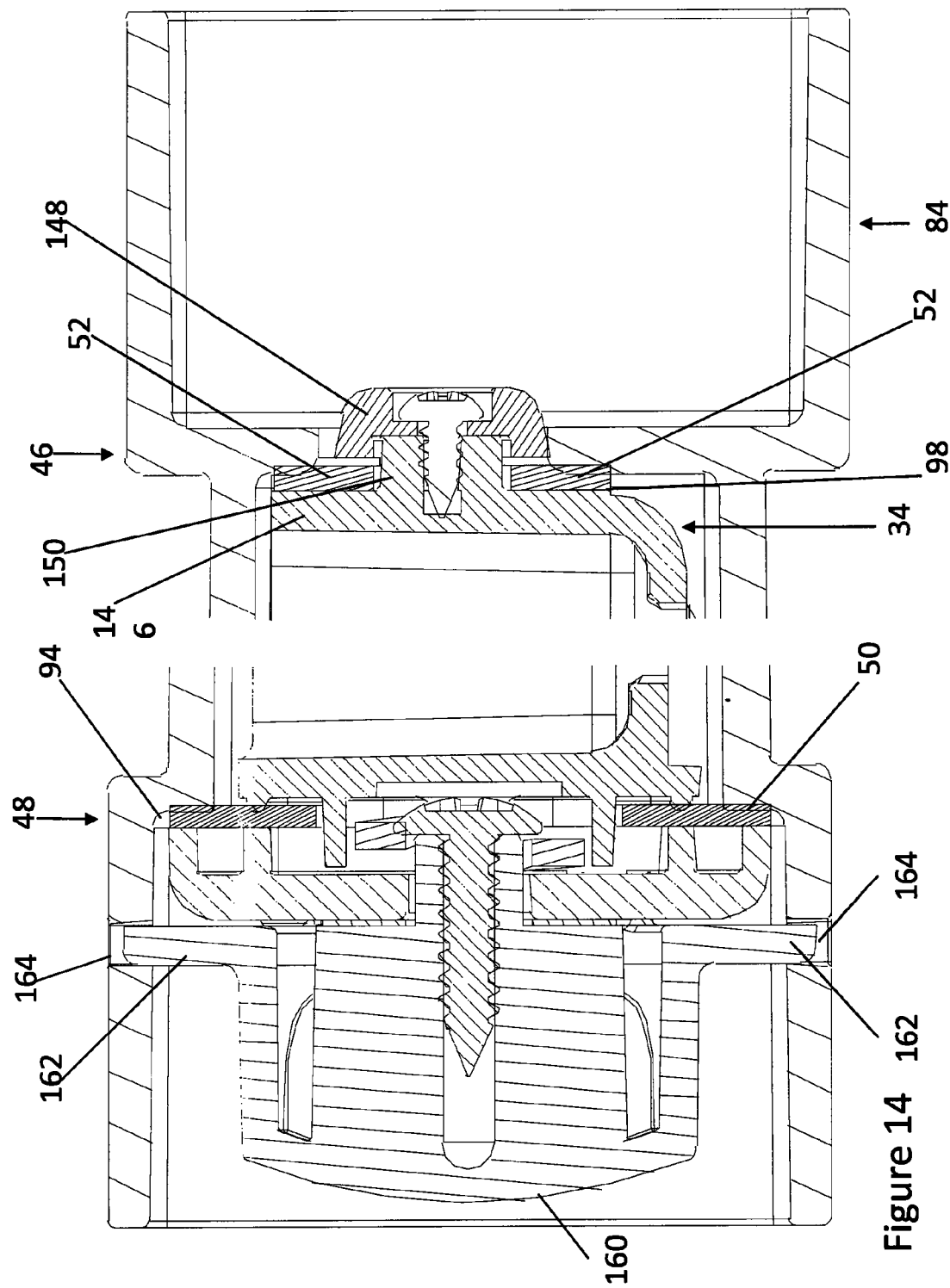
FIGS. 14(a) and (b) are close-up, side sectional views of a portion of a container.

As illustrated in FIGS. 10, 11, and 14, in one embodiment, the rear wall 34 includes a rear base 146 and a rear plate 148. The rear base 146 includes a rear bracket 150 extending transversely from the rear base 146 and laterally across a portion of the rear base 146. The rear bracket 150 is adapted to receive the rear seal 52. In one embodiment, the rear bracket 150 comprises a wall extending transversely from the rear base 146 and extending around a perimeter of the rear base 146. The rear seal 52 may be placed over or stretched around the rear bracket 150. The rear bracket 150 also may include means for receiving and engaging the rear plate 148. The rear plate 148 may be affixed to the rear base 146 and rear bracket 150 to hold the rear seal 52. The rear plate 148 may be affixed to the rear base 146 through mechanical means, such as by a fastener, threaded fastener, machine screw or self-tapping screw. In another embodiment, the rear bracket 150 is formed from a section of the rear base 146 which extends outwardly transversely from the rear base 146.

The rear seal 52 may be comprised of a silicone material such as a 1/16" thick layer of silicone. In one embodiment, the rear seal 52 has a height and width the same size as or slightly smaller than the height and width of the rear base 146. The rear seal 52 may comprise a bulb seal which engages the rear interface 46 and is further compressed as the rear wall 34 of the frame 12 engages the rear interface 46 of the sleeve 16 and as the front wall 32 of the frame 12 engages the front interface 48 of the sleeve 16. The rear plate 148 has a height and width smaller than the height and width of the rear seal 52 so that a portion of the rear seal 52 is exposed for engagement with the sleeve 16. In one embodiment, the rear seal 52 has a rectangular or rounded rectangular hole 152 so that the rear seal 52 may be stretched and placed over and rest on or around the rear bracket 150.

Figure 13:
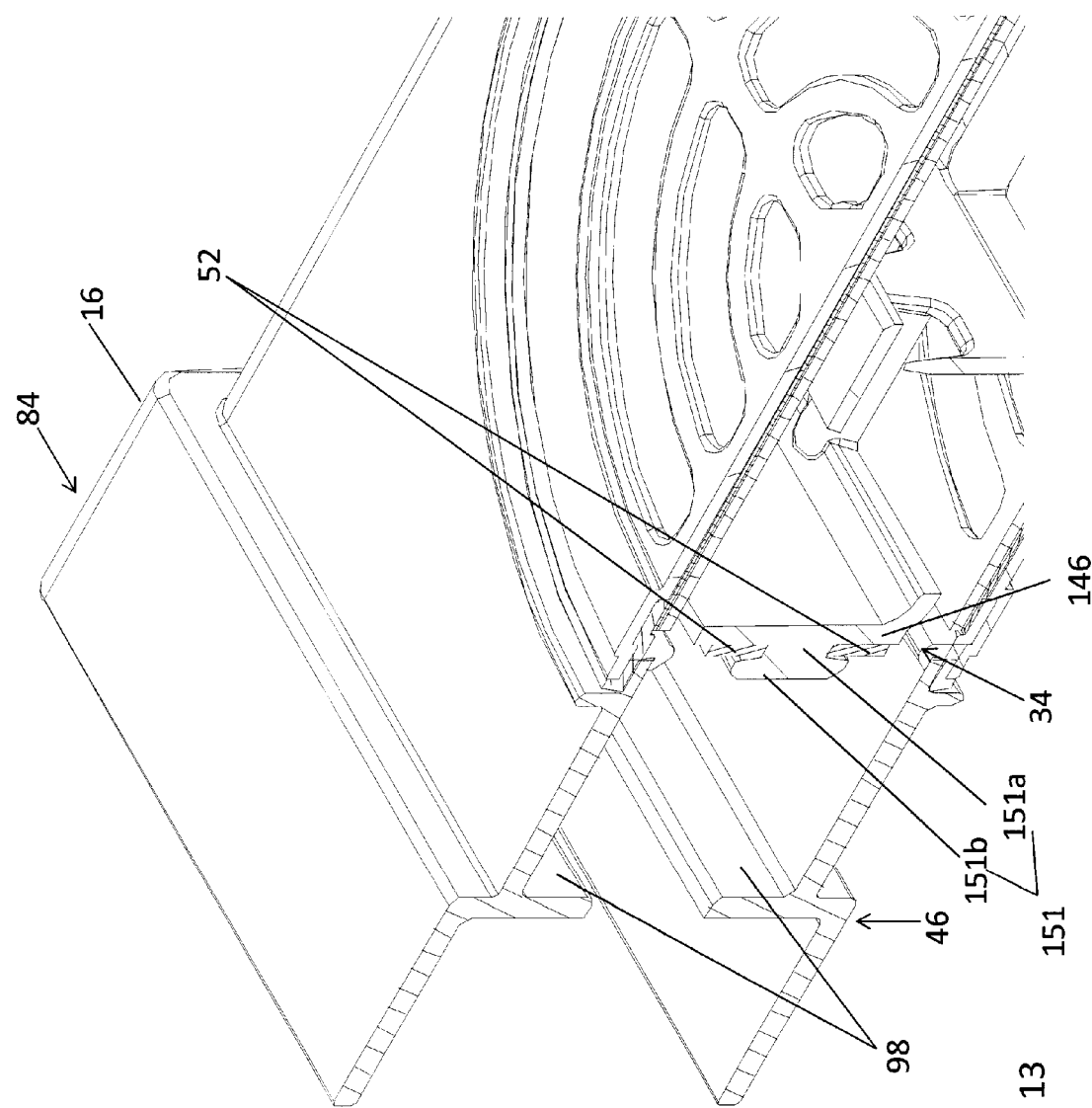
FIG. 13 is a sectional view of a rear portion of a frame partially inserted in a sleeve in accordance with an embodiment of the present disclosure.

FIG. 13 illustrates another embodiment in which the rear wall 34 comprises a rear base 146 and a rear bracket 151 which is formed from and which extends transversely from the rear base 146. The rear bracket 151 includes a first section 151a adjacent to the rear base 146 and a second section 150b adjacent to the first section 151a, with the second section 151b having a height and width greater than the first section 151a. As illustrated in FIG. 13, the rear seal 52 may be placed or stretched over the second section 151b and rest on or around the first section 151a adjacent to the rear base 146. The second section 151b of the bracket 151 has a height and width smaller than the height and width of the rear seal 52 so that a portion of the rear seal 52 is exposed for engagement with the sleeve 16.

In one embodiment of the container 10 as shown in FIGS. 13 and 14(b), a portion of the rear wall 34 of the frame 12 extends into the third region 84 of the sleeve 16. This provides a lead-in to center the frame 12 and the rear seal 52 with the rear interface 46. As shown in FIG. 14(b) a fillet radius of the rear plate 148 creates a cam action as the frame 12 is inserted in the sleeve 16 and guides the frame 12 upwards slightly to center the rear seal 52 against the rear interface 46. In embodiments where the dimensions of the sleeve 16, front interface 48 and rear interface 46 are symmetrical, the frame 12 may be inserted in the sleeve 16 with either the top panel 22 or the bottom panel 24 of the sleeve 16 facing upwards.

FIG. 13 illustrates a sectional view of the frame 12 and rear wall 34 with the frame 12 partially inserted in the sleeve 16. A portion of the rear seal 52 is exposed for engagement with a first surface 98 of the rear interface 46 when the frame 12 is fully inserted in the sleeve 16.

FIGS. 14(a) and (b) provide close-up side sectional views of the container 10 and engagement between the front wall 32 and rear wall 34 and the sleeve 16. As shown in FIG. 13(a), a portion of the front seal 50 engages a portion of the first surface 94 of the front interface 48. As shown in FIG. 14(b), a portion of the rear seal 52 engages a portion of the first surface 98 of the rear interface 46.

As shown in FIG. 11, in one embodiment the front wall 32 includes a knob 160 which may serve multiple functions. The knob 160 may include one or more tabs 162 which extend from the knob 160 in a plane parallel to the front wall 32. When the frame 12 is inserted in the sleeve 16, the knob 160 and tabs 162 may be turned or oriented to align with and extend into or through one or more slots 164 in the top panel 22, the bottom panel 24, or both the top and bottom panels 22, 24 of the sleeve 16. See, for example, the illustrations in FIGS. 1, 3 and 14. The engagement of the one or more tabs 162 with the one or more slots 164 in the sleeve 16 serves to lock the frame 12 in place in the sleeve 16 and maintains compression of front seal 50 and rear seal 52 to the respective front and rear interfaces 48, 46 on sleeve 16. The knob 160 may be turned to move the tabs 162 out of the slots 164 to allow for the removal of the frame 12 from the sleeve 16.

Figure 15:
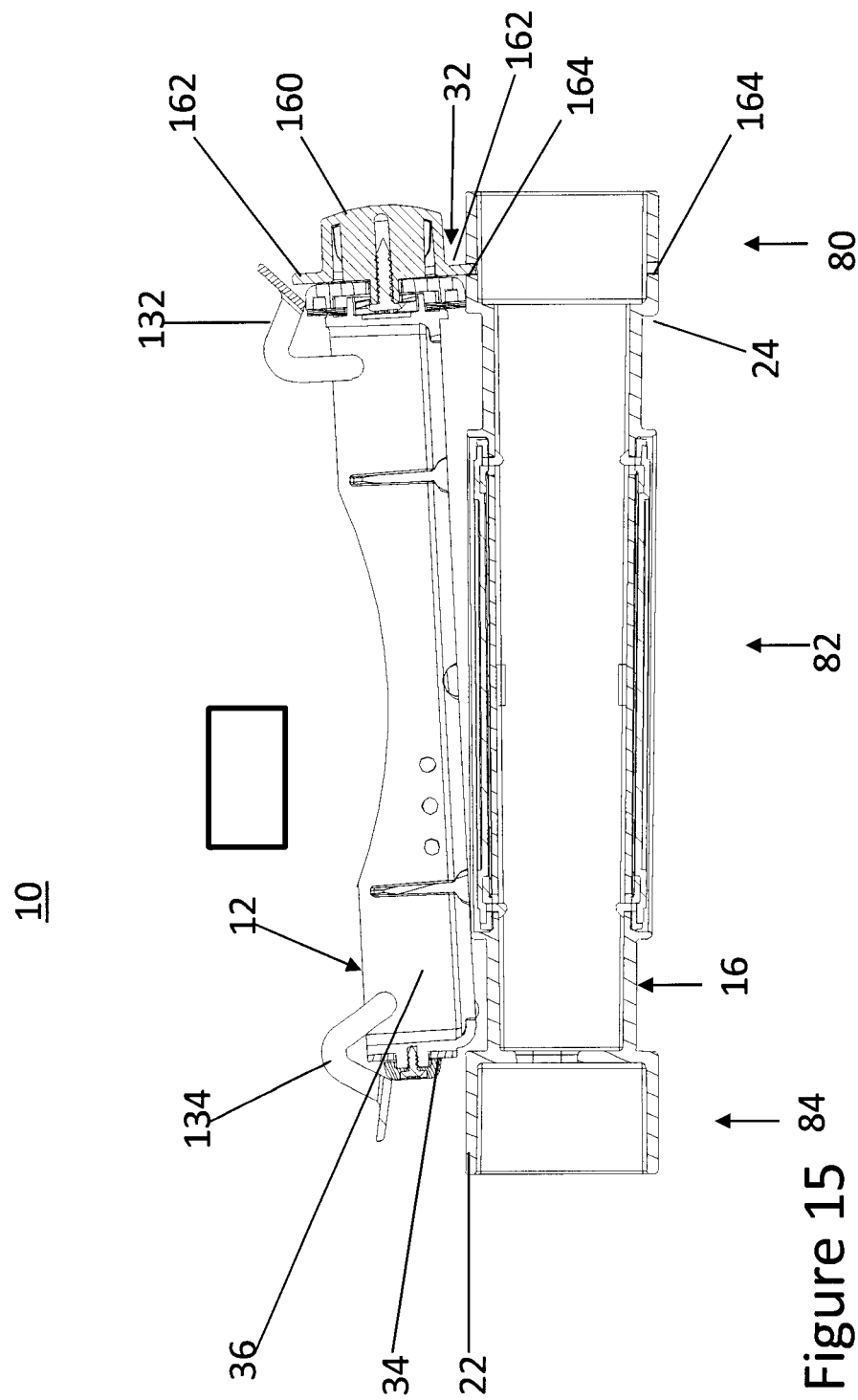
FIG. 15 is a side cross-section view of a container in a second configuration in accordance with an embodiment of the present disclosure.
Figure 17:
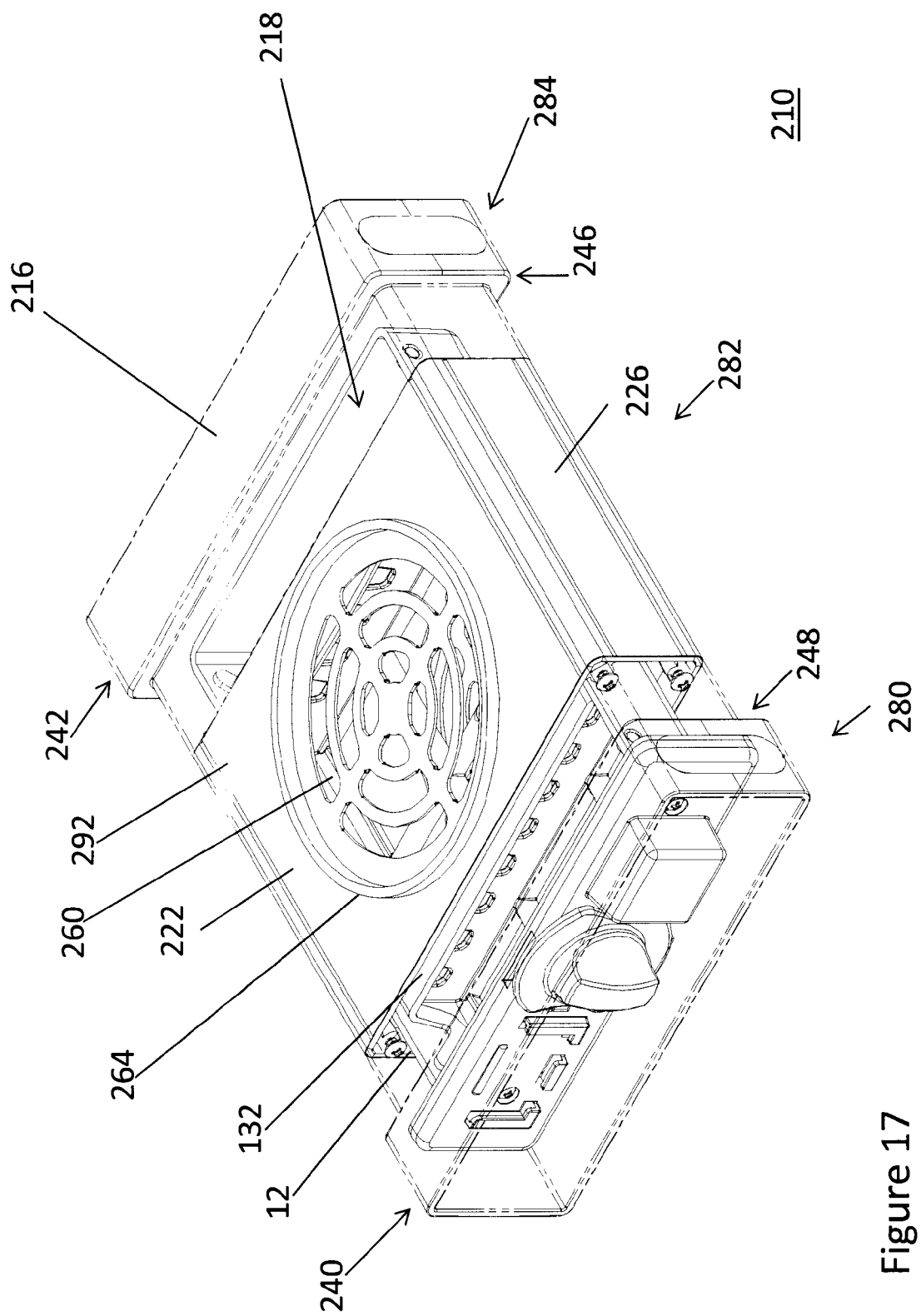
FIG. 17 is an isometric view of a container in accordance with another embodiment of the present disclosure.

As shown in FIG. 15, when the container 10 is arranged in the second configuration, the front wall 32 of the frame 12 may rest on the top panel 22 or on the bottom panel 24 of the first region 80 of the sleeve 16. The knob 160 and the one or more tabs 162 may be turned or oriented to align with and extend into or through the slot 164 in the top panel 22 or the bottom panel 24. The engagement between the tab 162 and slot 164 in the second configuration helps to prevent the frame 12 from moving when resting on top of the sleeve 16.

In some embodiments, the container 10 includes a holder for a label or chemical indicator (not shown), such as the holder 168 shown on the front plate 140 of the frame 12 in FIG. 11. A chemical indicator may change color after undergoing a sterilization process and provides an indication of the treatment of container 10. The holder 168 allows the chemical indicator to be removed and replaced after each sterilization cycle and use of the container 10 and instruments contained therein. In other embodiments, the holder 168 is adapted to retain a radio frequency identification (RFID) module that contains an autoclavable RFID tag for tracking of container contents.

In some embodiments, as shown in FIG. 25(a) and FIGS. 26(a) to (d), the container 10, 210 includes a holder 169 for retaining an indicator 269. The holder 169 may be located on a portion of the frame 12 which is visible when the frame 12 is inserted in the sleeve 16, 216. When the frame 12 and sleeve 16, 216 are in the first configuration, the indicator 269 is located in the holder 169 in the sterilization chamber 18, 218. The indicator 269 is thus exposed to the same conditions as, and provides an indication of, the state of the articles in the container 10, 210. The indicator 269 may comprise a chemical or biological based indicator and may provide a visual or other indication of the state and history of conditions to which the indicator 269 has been exposed. With the sleeve 16, 216 or a portion of the sleeve 16, 216 comprised of a transparent or semi-transparent material, the indicator 269 in the holder 169 of the frame 12 may be viewed to determine the sterilization status of the contents of the container 10, 210 without breaking the sterile seal of the container 10, 210. In other embodiments, one or more holders 169 and indicators 269 may be configured in different areas of the frame 12.

Figure 26:
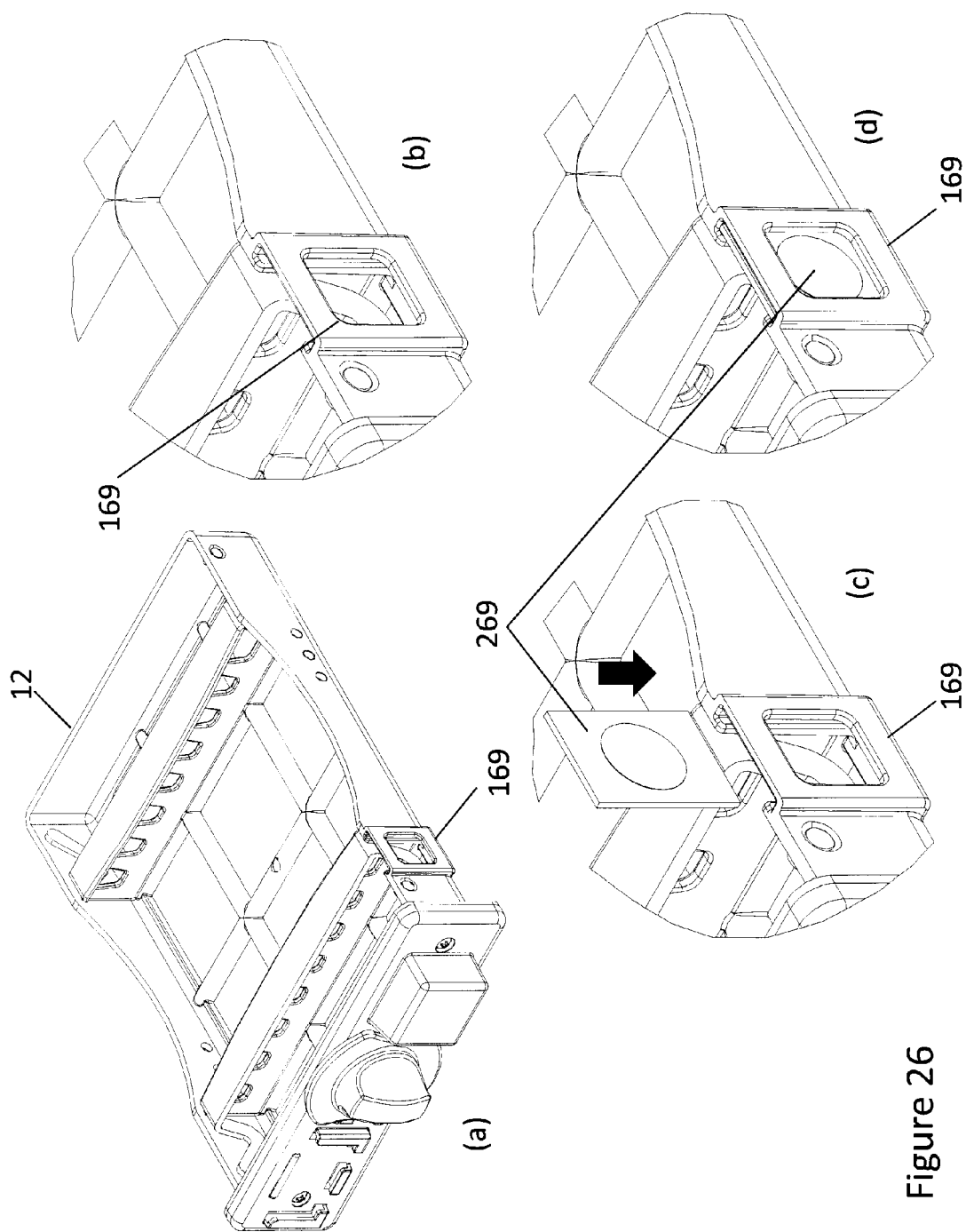
FIGS. 26(a) to (d) are isometric views of a frame in accordance with an embodiment of the present disclosure.
FIG. 26(e) is a front isometric view of a frame in accordance with an embodiment of the present disclosure.
FIG. 26(f) is a close-up, enlarged view of the frame of FIG. 26(e)
Figure 26E:
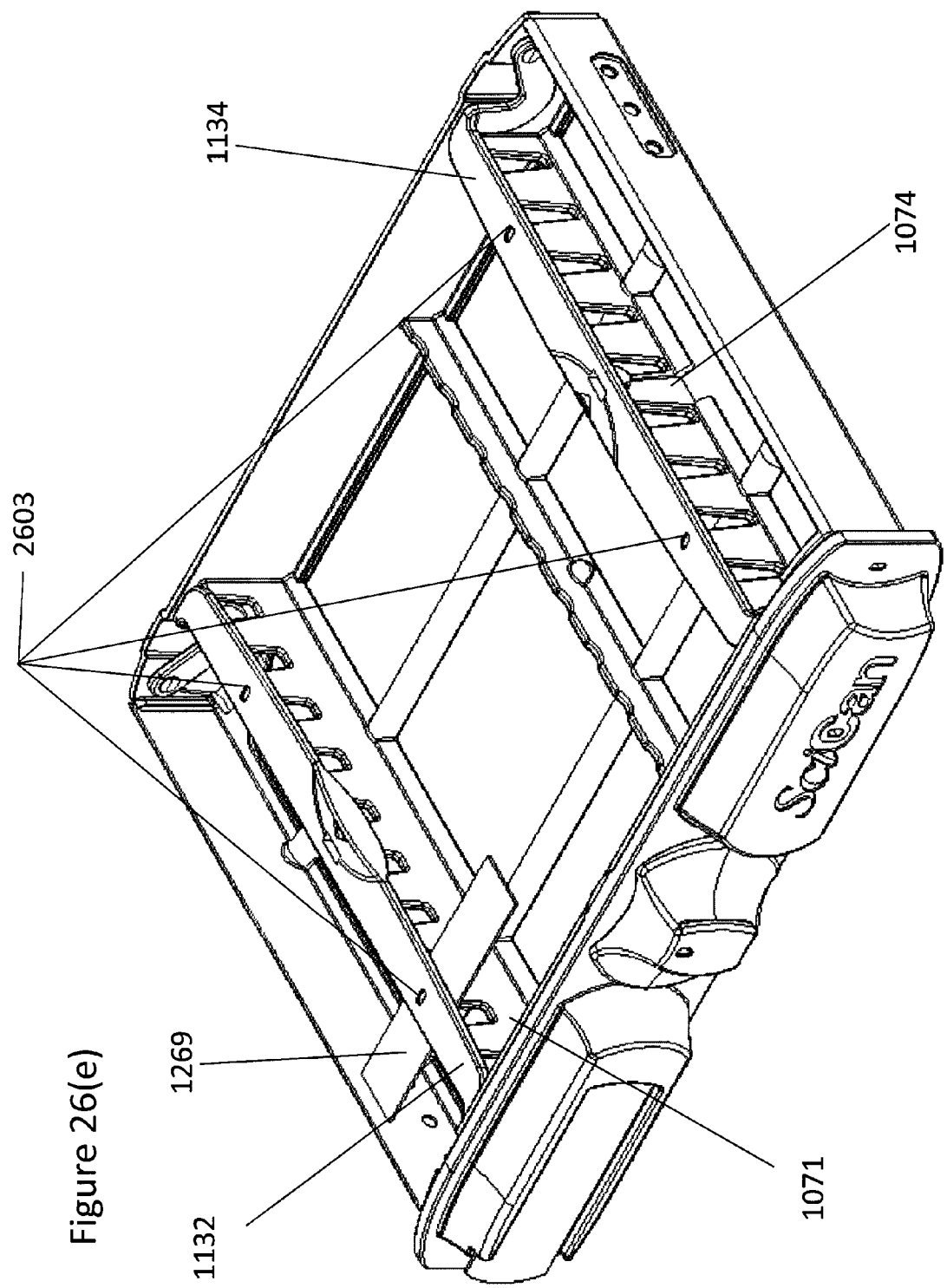
Figure 26F:
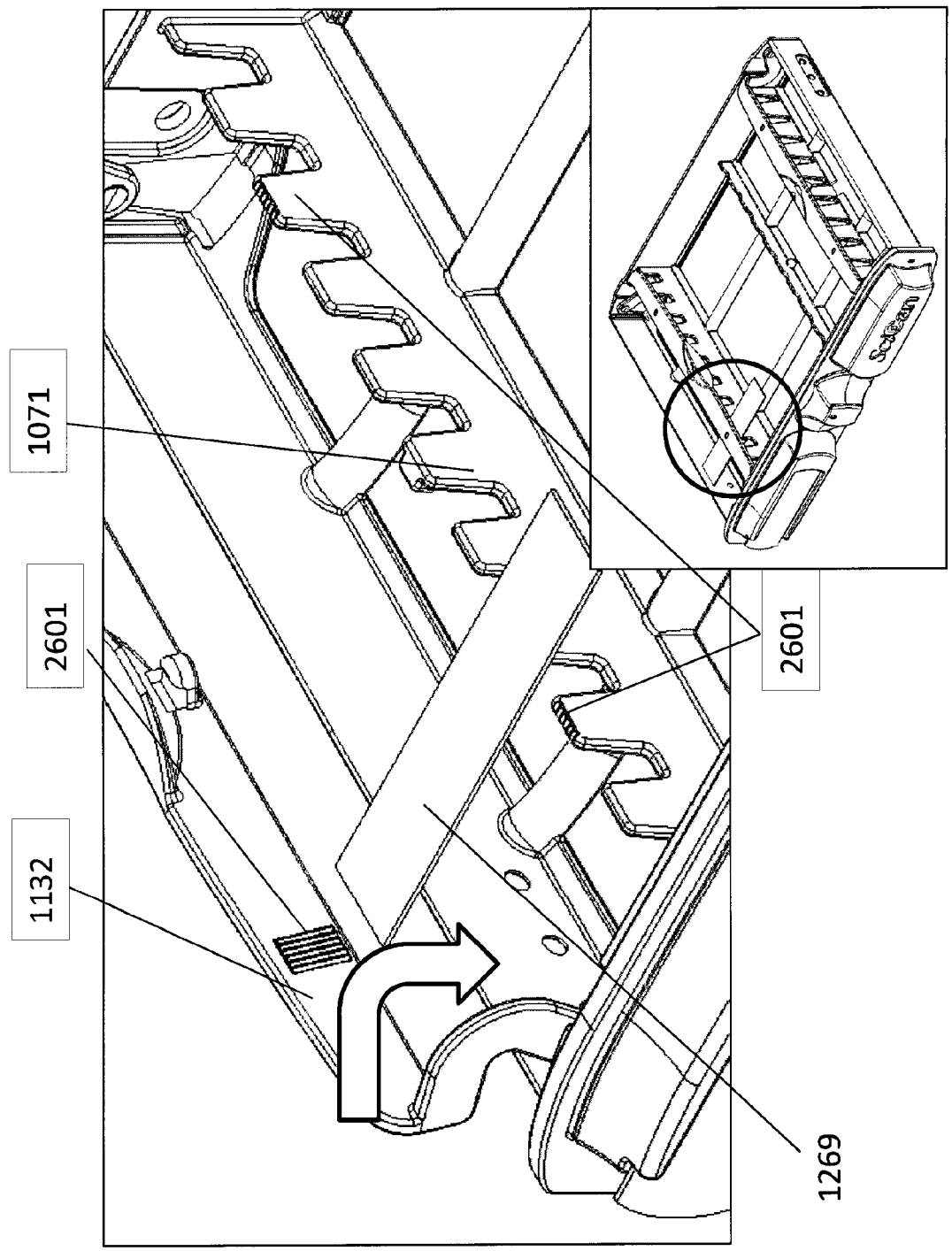

In other embodiments, the handles 1132, 1134 and supports or spacers of the frame 1012 are configured to retain one or more chemical indicators 1269. For example, as illustrated in FIGS. 26(e) and (f), a chemical indicator 1269 may be retained between the handle 1132 and the first support 1071 of the frame 1012, which is described in further detail below. As the handle 1132 is lowered down over the instruments and support 1071, the chemical indicator 1269 is also held in place. In some embodiments, serrated surfaces 2601 may be provided on one or both of the inner surface of handle 1132 and the top surface of the first support 1071 to secure the indicator 1269. One or more chemical indicators 1269 may be secured between the first support 1071 and the handle 1132 and one or more chemical indicators 1269 may be secured between the spacer 1074 and the handle 1134. Indicators 2603 may be provided on the handles 1132, 1134 to signal the locations for placement of the chemical indicators 1269. In these embodiments, different sized chemical indicators may be accommodated without requiring additional space or custom compartments within the container 10, 1000.

In some embodiments, the container 10 includes a tamper evident mechanism 170. The tamper evident mechanism 170 may comprise a tamper evident latch 172 and shape memory compression spring 174. The latch 172 may be comprised of PEEK and the compression spring 174 may be comprised of a nickel titanium alloy such as nitinol. The tamper evident mechanism 170 responds to elevated temperatures in a sterilization apparatus. The compression spring 174 expands as a result of the elevated temperatures and forces the latch 172 to move laterally or outwardly from the tamper evident mechanism 170. In another embodiment, the shape memory compression spring can be replaced by a linear-motion thermal actuator.

FIGS. 16(a) to (e) illustrate a front view of the container 10 and show an example embodiment of the tamper evident mechanism 170 working in cooperation with the knob 160. In FIG. 16(a), the frame 12 is inserted in the sleeve 16 but the knob 160 and tabs 162 are at a position wherein the tabs 162 do not extend beyond the frame 12. As shown in FIG. 16(b), the knob 160 may be turned, for example rotated clockwise by 90 degrees, to align the tabs 162 of the knob 160 with the slots 164 in the sleeve 16. In one embodiment, a symbol 176 such as an image of a deadbolt lock or the word "LOCK" is placed on the front of the front plate 140. The symbol 176 is revealed when the knob 160 is turned to the locked position to provide feedback and a quick visual indication that the container 10 is in a locked position. FIG. 16(c) illustrates the container 10 after a sterilization process. The compression spring 174 is expanded due to the high temperatures experienced during the sterilization process and the latch 172 is pushed by the compression spring 174 and moved outwardly from the tamper evident mechanism 170. In one embodiment, the knob 160 includes one or more recesses 178 which correspond in shape to the profile of the latch 172. As the latch 172 extends out from the mechanism 170, it engages the recess 178 of the knob 160 and prevents the knob 160 from being rotated. The mechanism 170 is configured such that the latch 172 may not be pulled out of the tamper evident mechanism 170 manually, the latch 172 is configured to extend from the mechanism 170 only in response to the temperatures of a sterilization process. Thus, as shown in FIG. 16(*c*), the status of the container 10 and articles contained therein is clearly indicated by the lock symbol 176 and the appearance of the latch 172 engaging the knob 160. FIG. 16(*d*) illustrates the first step to open the container 10. In one embodiment, the latch 172 retracts in response to the cam action of the profile of the knob 160 as the knob 160 is rotated to an "unlock" position. In another embodiment, the latch 172 first must be manipulated back into its original position in the mechanism 170 prior to rotation or movement of the knob 160. The latter two-step process to unlock the container 10 provides protection against users accidentally turning the knob 160. After the latch 172 is returned to the mechanism 170, it is disengaged from the recess 178 of the knob 160 and the knob 160 may be turned as illustrated in FIG. 16(*e*). As the knob 160 is turned, for example turned 90 degrees in a counter-clockwise direction, the tabs 162 are removed from the slots 164 in the sleeve 16. With the tabs 162 in positions which do not extend beyond the frame 12, the frame 12 may be removed from the sleeve 16.

FIGS. 17 to 20 illustrate alternative embodiments of a container 210 which includes a frame 12 and a sleeve 216. In the illustrated embodiments, the sleeve 216 and frame 12 sealably engage to create a sterilization chamber 218. The sleeve 216 comprises a top panel 222, a bottom panel 224, a first side panel 226 and a second side panel 228. The top panel 222, bottom panel 224, first side panel 226 and second side panel 228 define a cavity 230 for receiving and housing the frame 12. In one embodiment, the cavity 230 is generally rectangular in shape.

In one embodiment, a rear interface 246 at a rear end 242 of the sleeve 216 engages the rear wall 34 of the frame 12. A front interface 248 at a front end 240 of the sleeve 216 engages the front wall 32 of the frame 12. The container 210 may include a front seal 50 and a rear seal 52 at the respective front and rear interfaces 248, 246, one or more tortuous paths (not shown) at the front and rear interfaces 248, 246, or a combination of seals and tortuous path configurations. The front and rear interfaces 248, 246 may be formed as described above.

Figure 18:
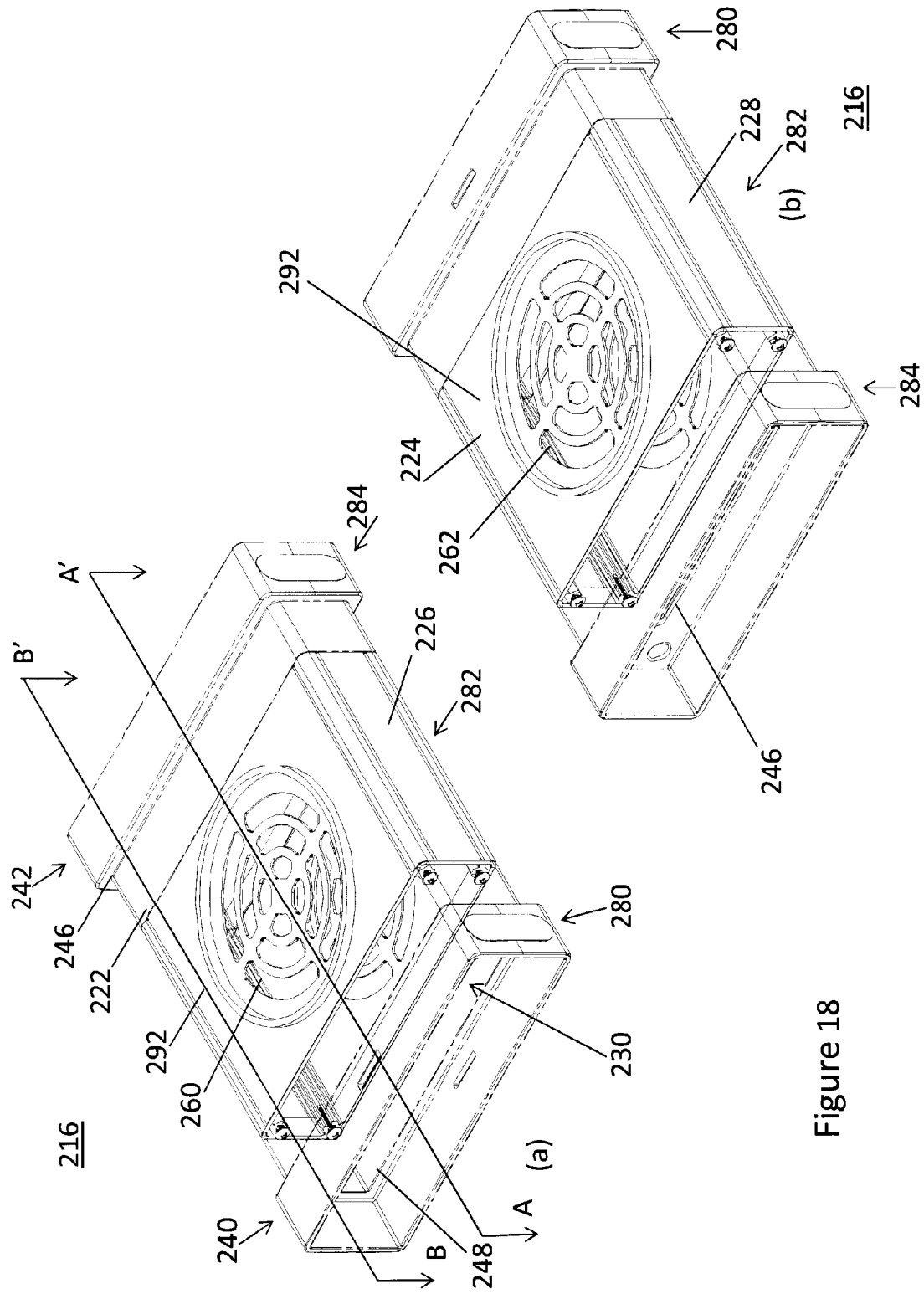
FIGS. 18(a) and (b) are front top and rear bottom isometric views of the sleeve of FIG. 17.
Figure 19:
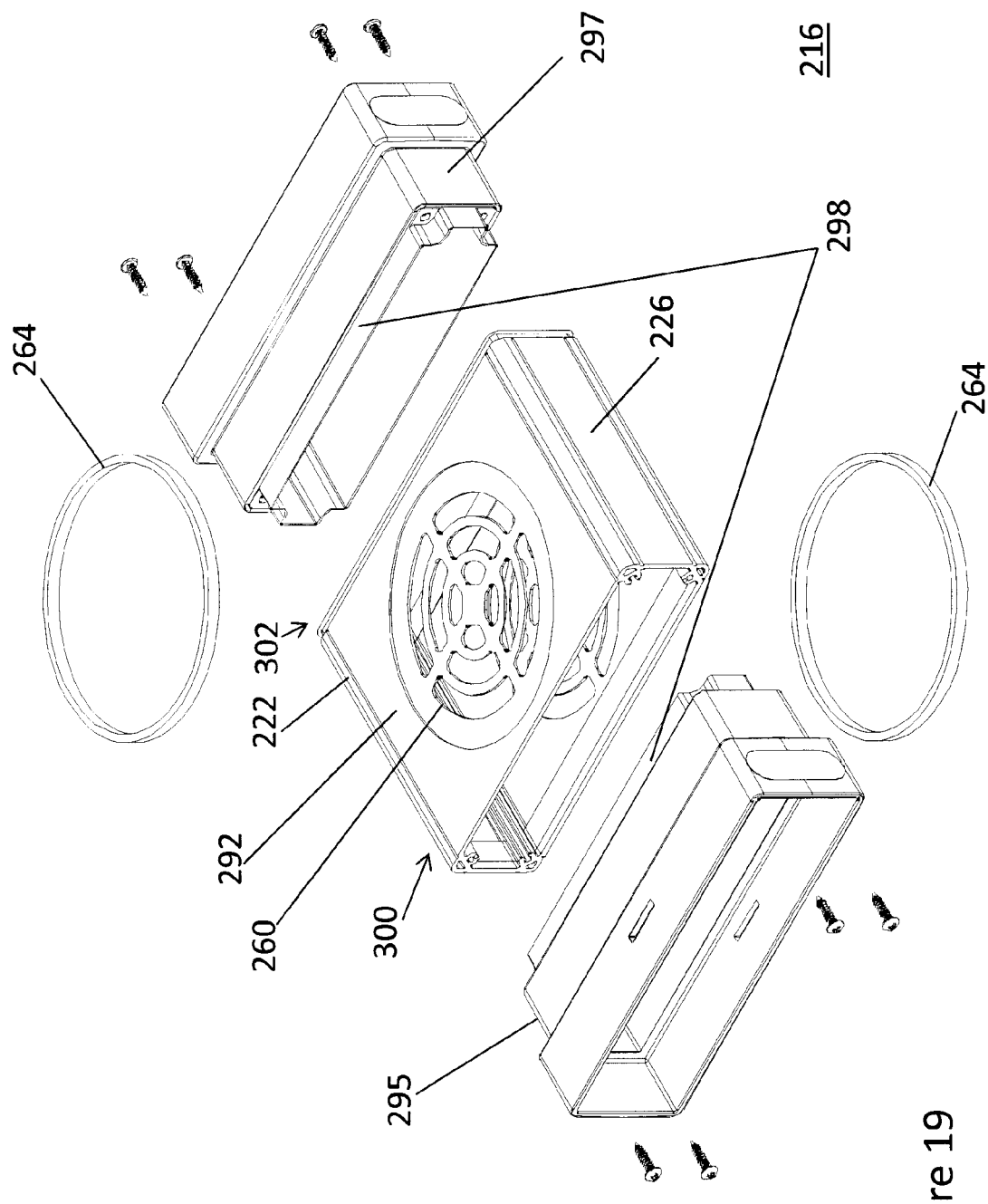
FIG. 19 is an exploded view of the sleeve of FIG. 18(a)

The container 210 includes at least one opening for communication of steam and air between a sterilization apparatus and the sterilization chamber 218. In one embodiment, as illustrated in FIGS. 18 and 19, the sleeve 216 includes a plurality of openings 260 in the top panel 222 of the sleeve 216, and a plurality of openings 262 in the bottom panel 224 of the sleeve 216. An opening or a plurality of openings may be provided in one or both side panels 226, 228.

One or more filter assemblies 70, comprising a retainer 114 and a filter layer 112, as described above, may be provided adjacent to the pluralities of openings 260, 262 in the container 210. The filter assembly 70 (not shown in FIGS. 18 and 19) may be sized to correspond to the plurality of openings 260 in the sleeve 216. The sleeve 216 includes a base 264 for receiving the filter assembly 70. The base 264 comprises a wall extending outwardly from the top panel 222 and around the plurality of openings 260. In one embodiment, the base 264 comprises a segment of aluminum tube which is formed and press-fit into a recessed portion of the top panel 222 of the sleeve 216. A base 264 for receiving a filter assembly 70 also may be provided around the plurality of openings 262 in the bottom panel 224, or around other openings provided in the sleeve 216 for the communication of steam and air.

One or more attachment mechanisms may be used to hold the retainer 114 and filter layer 112 of the filter assembly 70 in place in the base 264. As described above, the retainer 114 includes one or more snap tabs 116 which mate with one or more corresponding slots in the top panel 222 of the sleeve 216. The snap tabs 116 may comprise a hooked end which flexes to allow the retainer 114 to be placed over and locked with the top panel 222. The hooked end engages an interior surface of the top panel 222 to prevent the retainer 114 and filter layer 112 from becoming dislodged. In one embodiment, the retainer 114 is removed from the sleeve 216 by moving the hooked end of the snap tab 116 from within the cavity 230 of the sleeve 216 in order to free the snap tab 116 from the slot.

The plurality of openings 260 in the sleeve 216 and the plurality of openings 120 in filter assembly 70 also may be configured in shapes and locations other than the circular and centered configuration shown in the figures. In one embodiment, one or more pluralities of openings 260 and filter assemblies 70 are provided in one or both of the first and second side panels 226, 228.

In one embodiment, the sleeve 216 comprises a first region 280, a second region 282 which is disposed discretely from the first region 280, and a third region 284 which is disposed discretely from the second region 282. For the purposes of illustration and discussion, the first region 280 is situated at the front end 240 of the sleeve 216 and the third region 284 is situated at the rear end 242 of the sleeve 216. In one embodiment, the front interface 248 is provided in the sleeve 216 between the first and second regions 280, 282 for engaging the front wall 32 of the frame 12 and the rear interface 246 is provided between the second and third regions 282, 284 for engaging the rear wall 34 of the frame 12.

The second region 282 comprises a section 292 which is comprised of a metal material such as aluminum. In one embodiment, the section 292 comprises a portion of each of the top panel 222, the bottom panel 224, the first side panel 226 and the second side panel 228 being comprised of, metal. In one embodiment, the section 292 is relatively centered within the second region 282. The metal section 292 stores heat during the sterilization phase of a sterilization process and then releases the stored thermal energy during the drying phase of the sterilization process to facilitate the drying of the contents in the sterilization chamber 218.

Figure 20:
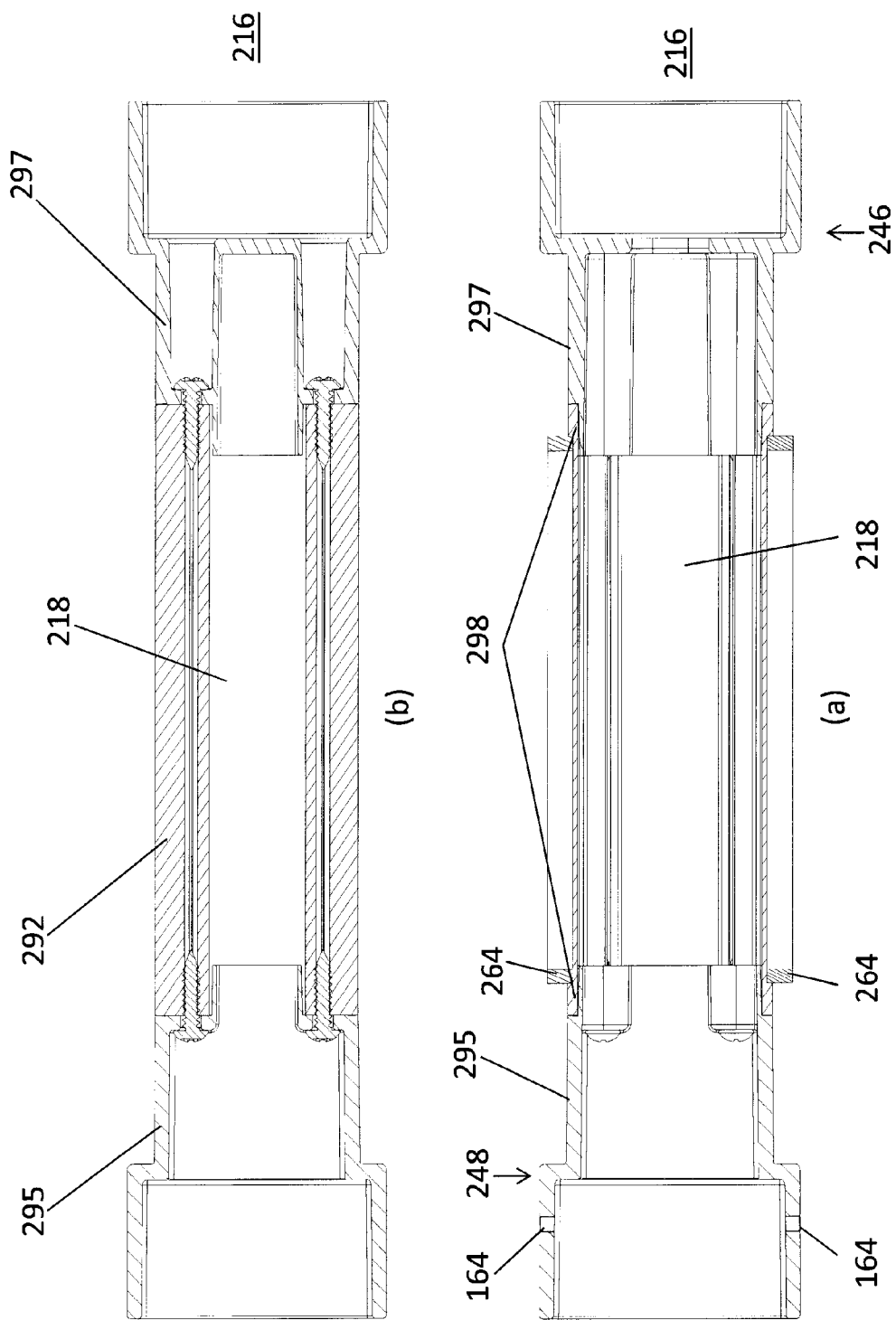
FIG. 20(a) is a longitudinal cross-section view of the sleeve of FIG. 18(a) at line A-A' and FIG. 20(b) is a longitudinal cross-section view of the sleeve of FIG. 18(a) at line B-B'.

As illustrated in further detail in FIGS. 19, 20(*a*) and 20(*b*), the section 292 may be constructed separately and affixed to respective front and rear sections 295, 297 of the second region 282. In some embodiments, as illustrated, the section 292 is mechanically affixed to respective front and rear sections 295, 297 of the second region 282 such as by fasteners, threaded fasteners, machine screws or self-tapping screws. In some embodiments, as illustrated, front and rear seals comprising medical adhesive sealant material, such as an epoxy material, are provided on the mating surfaces 298 of the front and rear sections 295, 297 of the second region 282. In some embodiments, additional front and rear seals (not shown) comprising gaskets or o-rings are provided between the front section 295 and a front portion 300 of the section 292 and between the rear section 297 and a rear portion 302 of the section 292.

The first region 280, third region 284 and the front and rear sections 295, 297 of the second region 282 of the sleeve 216 may be comprised of polyetherimide (PEI) or polyphenylsulfone (PPSU) or any other suitable material which may withstand multiple washing and sterilization cycles and which is transparent or semi-transparent such as tempered glass or borosilicate glass. The section 292 of the second region 282 of the sleeve 216 may be comprised of metal such as aluminum or specifically, aluminum 6063. The first region 280 and the front section 295 may be formed as one piece and the third region 284 and rear section 297 also may be formed as one piece. In one embodiment, the holder 169 of the indicator 269 is situated on the frame 12 so as to be visible through the front section 295 or rear section 297 of the second region 282 of the sleeve 216 to provide an indication of the sterilization process received by the contents of the container 210.

Figure 21:
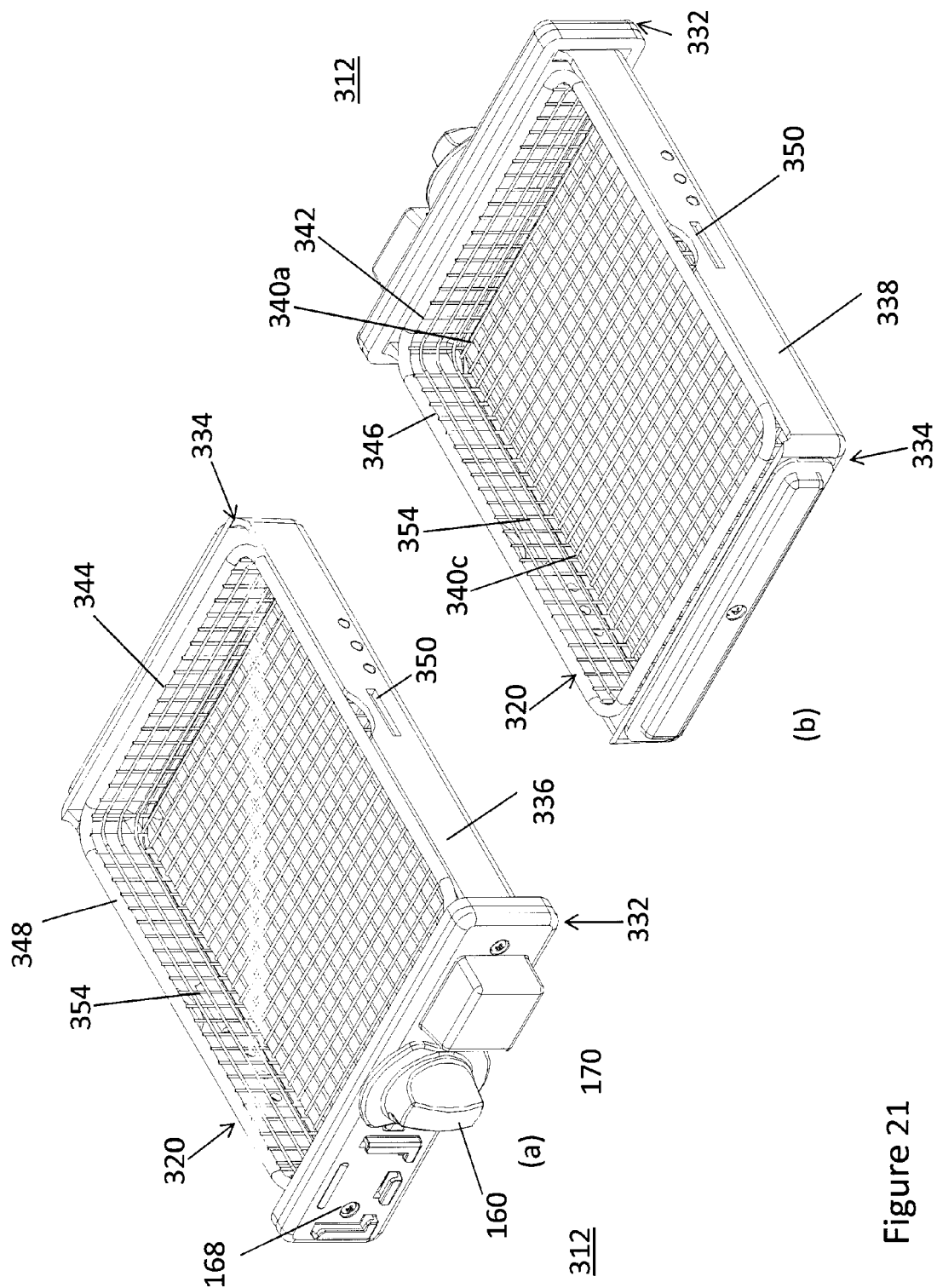
FIGS. 21(a) and (b) are isometric views of a frame in accordance with another embodiment of the present disclosure.
Figure 22:
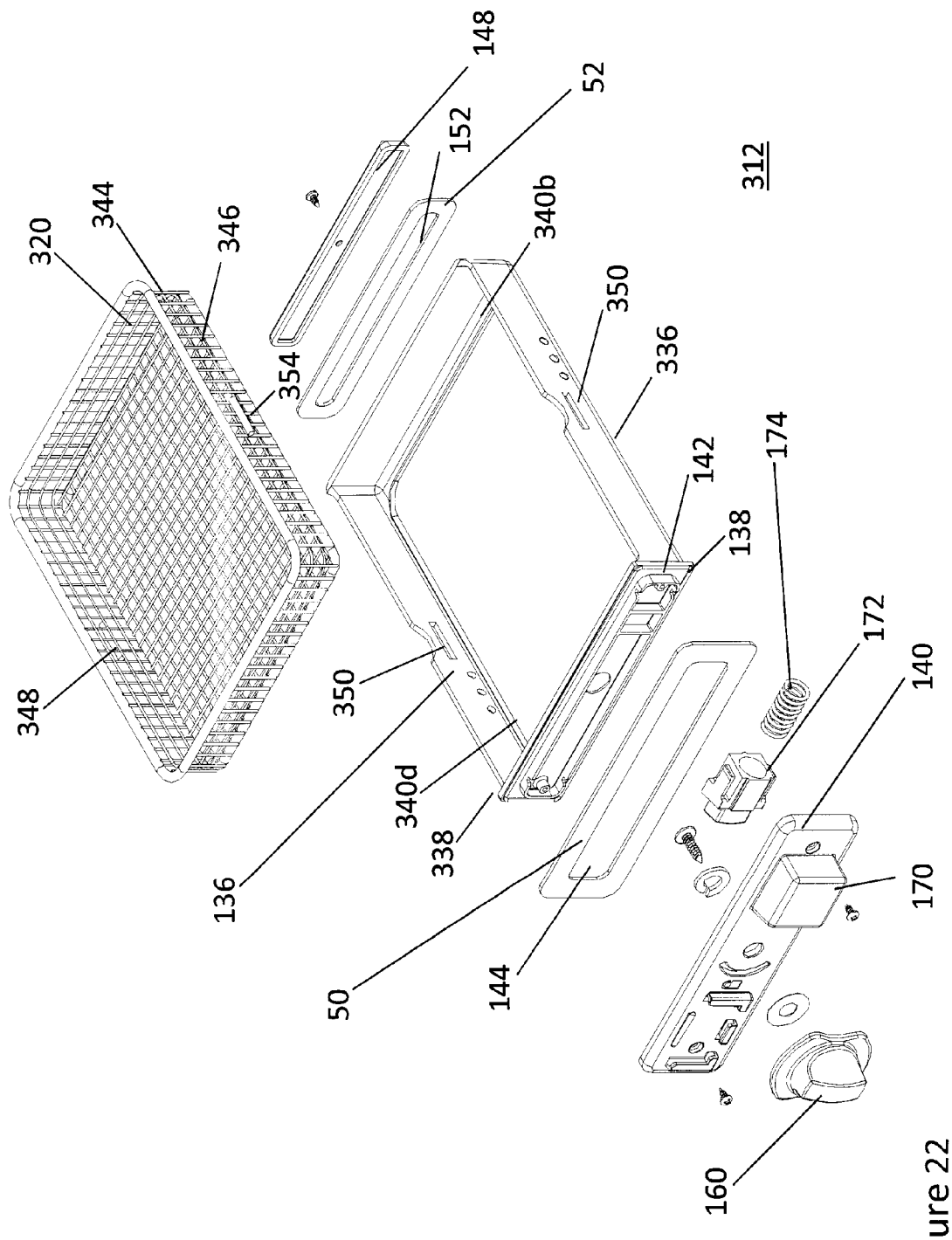
FIG. 22 is an exploded view of the frame of FIG. 21.

FIGS. 21 to 24 illustrate alternative embodiments of frames in accordance with the present disclosure. FIGS. 21 and 22 illustrate a frame 312 which is adapted to receive a basket 320. The frame 312 may also receive other cassettes containing instruments and articles for sterilization. In some embodiments, the frame 312 (not shown) comprises a front wall and a rear wall which are adapted to be affixed to the basket. In other embodiments, the frame 312 includes a front wall 332, a rear wall 334, a first side wall 336 and a second side wall 338 which are adapted to receive the basket 320. In one embodiment, the frame 312 may include one or more members 340a, 340b, 340c, 340d adjacent to a bottom portion of each of the front, rear and first and second side walls 332, 334, 336, 338 as illustrated in FIGS. 21(b) and 22. The members 340a, 340b, 340c, 340d may comprise bottom portions of the front, rear and first and second side walls extending horizontally within the interior of the frame 312 to add support or stability for the frame 312. In other embodiments (not shown), the frame 312 is adapted to receive other instrument assemblies including but not limited to instrument cassettes and spacers or holders designed to receive particular medical or dental instruments, such as hinged instruments, lumens and dental implants. The front wall 332 and rear wall 334 may comprise a number of components and are configured as described above for engaging the front and rear interfaces 48, 248, 46, 246 of the sleeve 16, 216.

The basket 320 comprises a front wall 342, a rear wall 344, a first side wall 346 and a second side wall 348. The basket 320 may receive instruments or articles for sterilization. The basket 320 may include a plurality of openings in the front, rear and side walls 342, 344, 346, 348 or the basket 320 may comprise a mesh structure as illustrated. In one embodiment, one of the first or second side walls 336, 338 of the frame 312 includes at least one slot 350 which is adapted to receive a tab 354 extending from a corresponding side wall of the basket. In one embodiment, the basket 320 includes tabs 354 on the first and second side walls 336, 338 which are adapted to be received by respective slots 350 in the side walls 336, 338 of the frame 312. The engagement of the tabs 354 and, slots 350 secures the basket 320 within the frame 312. The basket 320 may be comprised of a material which may be flexed and mounted to fit within the frame 312 with the tabs 354 aligned within the slots 350. In other embodiments (not shown), the basket 320 may include tabs which may be flexed and inserted into the slots 350. In other embodiments, the basket 320 may be affixed to the frame 312 with clips (not shown), such as clips comprised of spring steel. In one embodiment, the basket 320 is comprised of a metal material such as stainless steel 304 or a plastic material such as polyphenylene sulfide (PPS) or polyether ether ketone (PEEK). A basket 320 comprised of a metal material also serves to store thermal energy during the sterilization phase of the sterilization process and facilitates drying of the articles in the container 10 during the drying phase of the sterilization process. In some embodiments, the frame 312 is comprised of a plastic material such as polyphenylene sulfide (PPS) or polyether ether ketone (PEEK).

Figure 23:
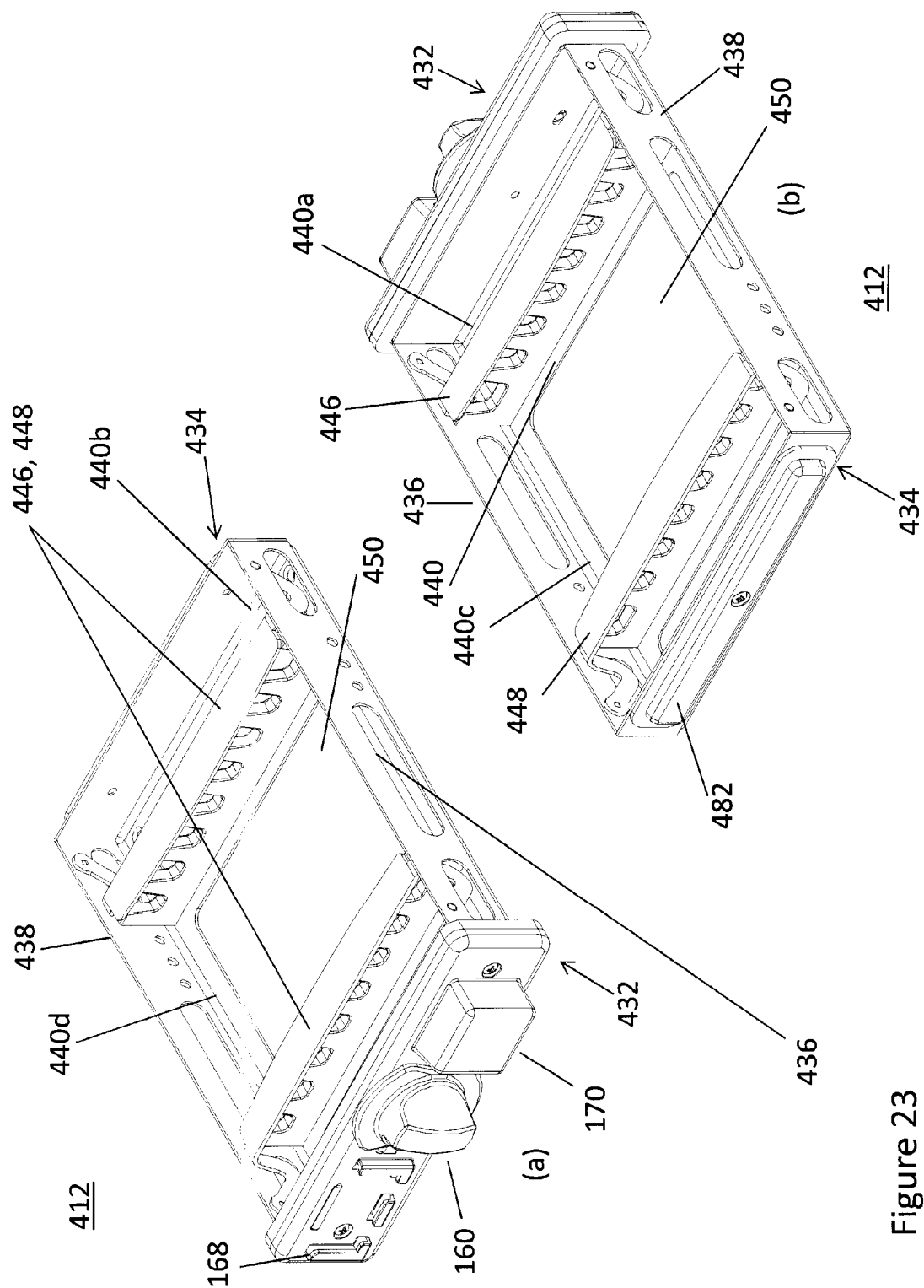
FIGS. 23(a) and (b) are isometric views of a frame in accordance with another embodiment of the present disclosure.
FIG. 23(c) is a partial exploded view of the frame of FIGS. 23(a) and (b)
Figure 23C:
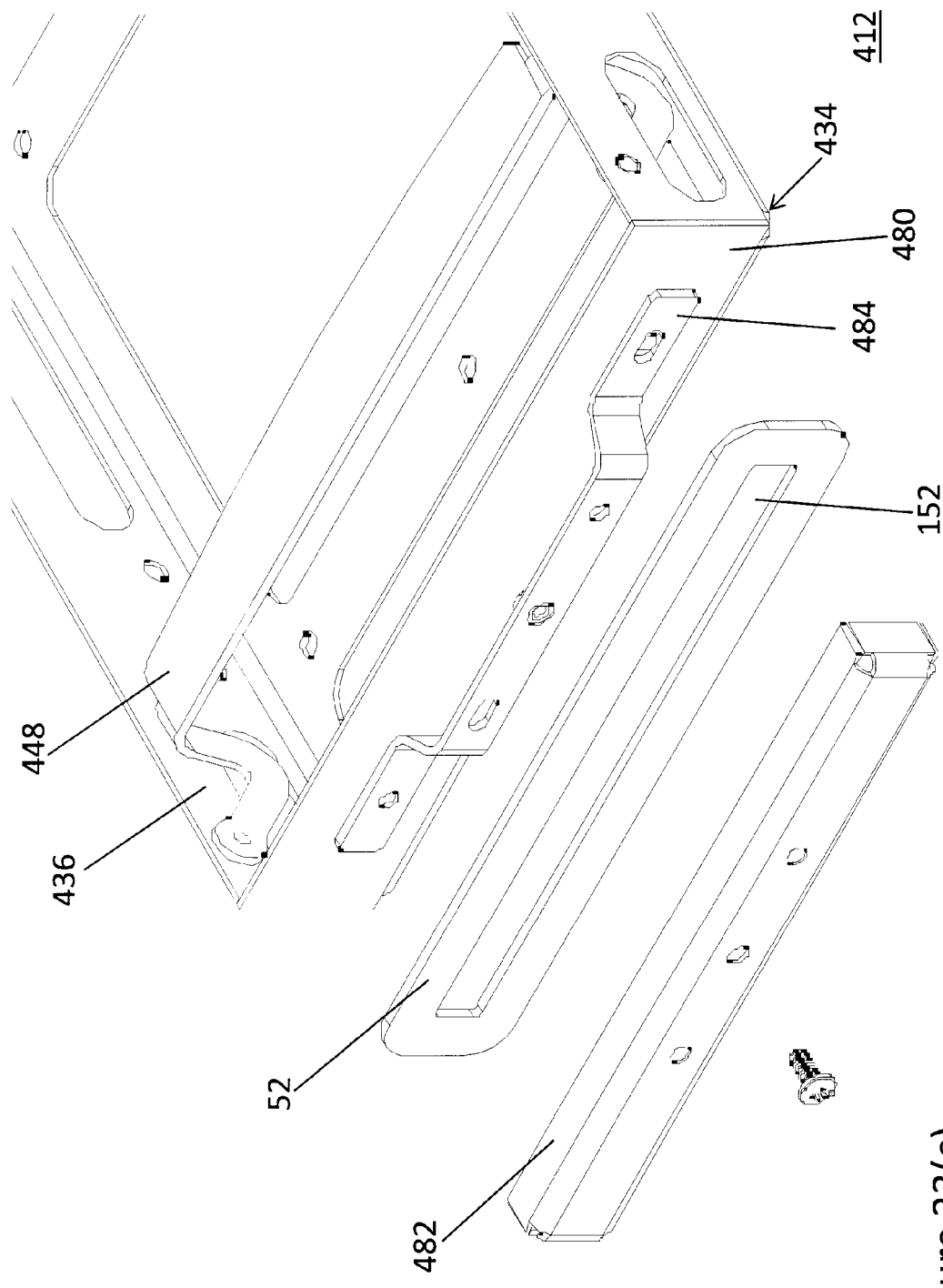
Figure 24:
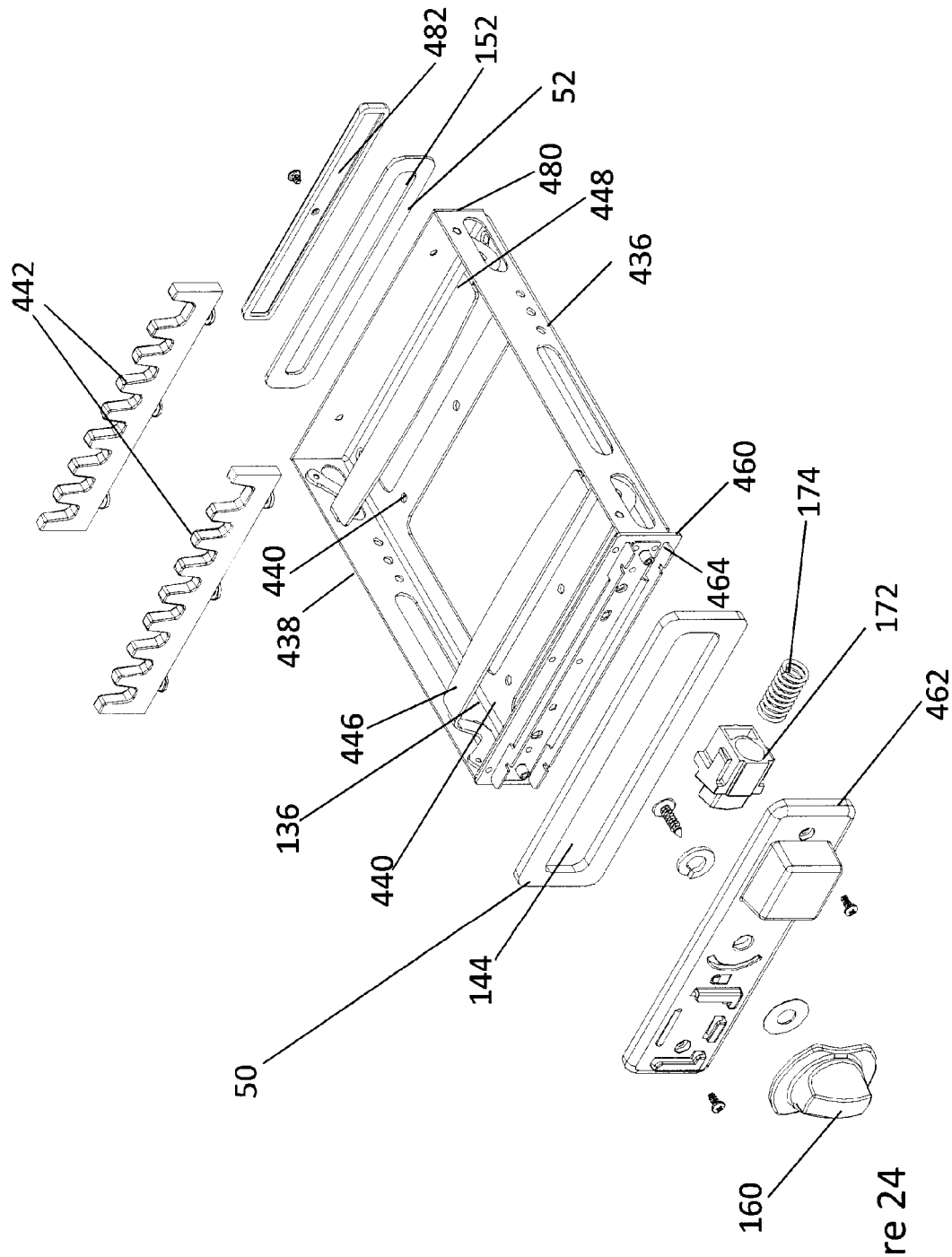
FIG. 24 is an exploded view of the frame of FIG. 23.
Figure 25:
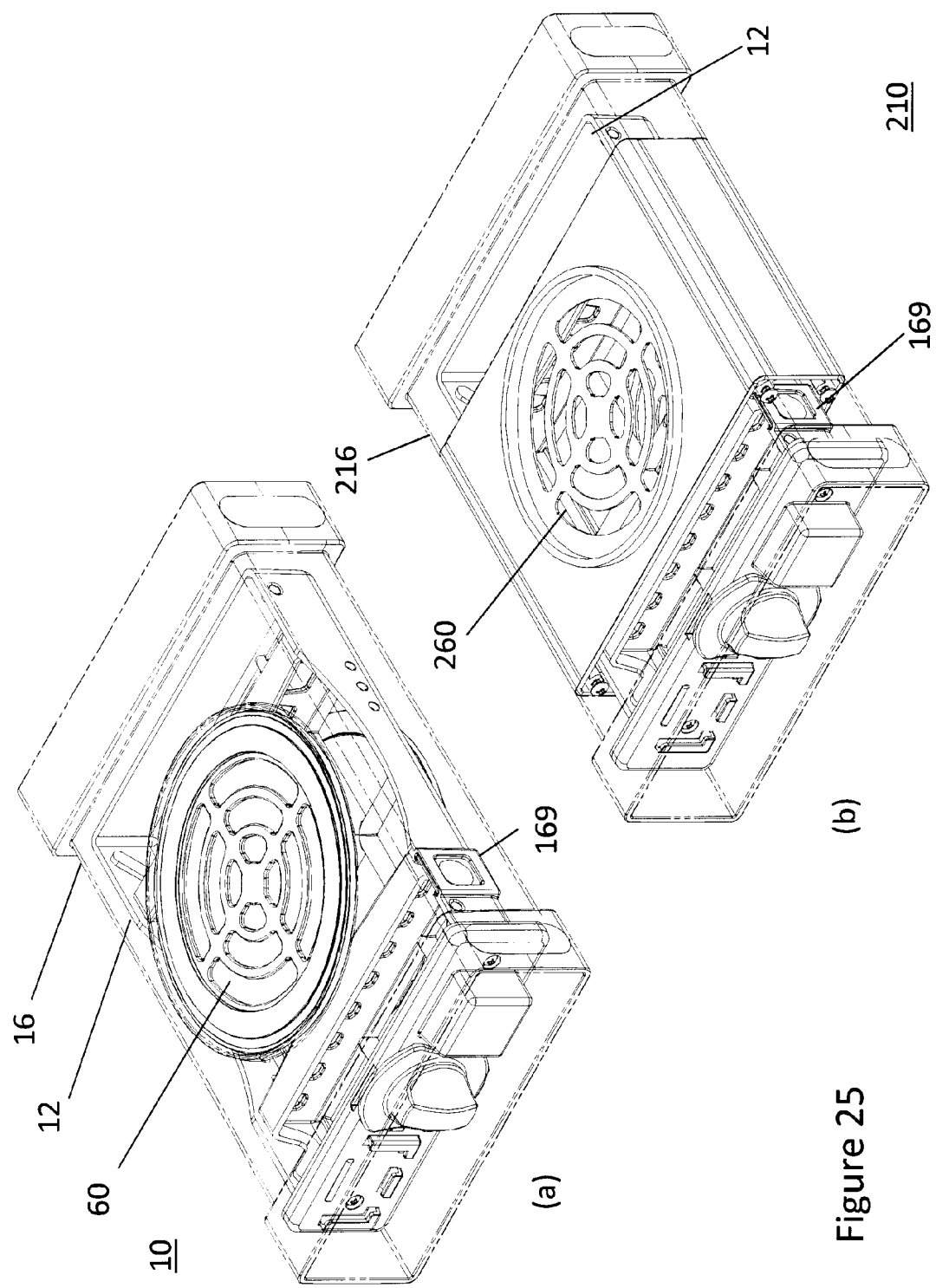
FIGS. 25(a) and (b) are isometric views of containers in accordance with embodiments of the present disclosure.

FIGS. 23 and 24 illustrate a frame 412 in accordance with another embodiment of the present disclosure. In some embodiments (not shown), the frame 412 comprises a front wall and a rear wall which are adapted to receive articles for sterilization. In other embodiments, the frame 412 includes a front wall 432, a rear wall 434, a first side wall 436 and a second side wall 438 which are adapted to receive one or more instruments (not shown) for sterilization. The frame 412 is comprised of a metal material such as stainless steel 304, which stores heat during a sterilization phase and releases stored thermal energy during a drying phase to facilitate the drying of the load at the end of the sterilization process.

As illustrated in FIGS. 23 and 24, the frame 412 comprises a front wall 432, a rear wall 434, a first side wall 436 and a second side wall 438. The frame 412 is adapted to hold one or more articles for sterilization, such as medical or dental instruments. In one embodiment, the frame 412 includes one or more members 440 which extend laterally, longitudinally, or both laterally and longitudinally across the frame 412. The members 440 may provide structural support for the frame 412. The members 440 may be situated at the bottom of the walls of the frame 412 to provide support for the articles received in the frame 412. In one embodiment, the frame 412 includes one or more members 440 adjacent to a bottom portion of each of the front, rear and first and second side walls. The members 440 may comprise bottom portions 440a, 440b, 440c, 440d of the front, rear and first and second side walls 432, 434, 436, 438 extending horizontally within the interior of the frame 412 to add support or stability for the frame 412.

As illustrated, the one or more members 440 may support one or more spacers 442 which are adapted to receive instruments for washing and sterilization and to maintain space between the instruments to allow for the passage of water, steam and air around the instruments during the washing and sterilization processes. The spacers 442 may comprise a silicone material. The spacers 442 may be mechanically affixed to the members 440 of the frame 412.

The frame 412 may include one or more handles, such as a handle 446 mounted to the first side wall 436 and the second side wall 438, adjacent to the front wall 432 and a handle 448 446 mounted to the first side wall 436 and the second side wall 438 adjacent to the rear wall 434. The handles 446, 448 are mechanically and pivotally attached to the side walls 436, 438. In one embodiment, the handles 446, 448 are pivotally attached permanently to the frame 412 using self-clinching fasteners or rivets. The handles 446, 448 also may be comprised of stainless steel or plastic material such as polyphenylene sulfide (PPS) or polyether ether ketone (PEEK). In one embodiment, the handles 446, 448 are configured in a first position and are contained within an interior 450 of the frame 412. The handles 446, 448 may rest on or adjacent to one or more spacers 442 to retain or secure the instruments held or resting within the spacer 442. When the frame 412 is not contained within the sleeve 16, 216, the handles 460, 462 may be moved to a second position wherein the handles 446, 448 extend outwardly from the frame 412. The handles 446, 448 may be used in the second position to move the frame 412 and instruments contained therein. Adjusting the handles 446, 448 to the second position also allows for access to the instruments contained in the frame 412.

In some embodiments, the front wall 432 and rear wall 434 comprise a number of components and are configured as described above for engaging the front and rear interfaces 48, 248, 46, 246 of the sleeve 16, 216. In some embodiments, the front wall 432 includes a front base 460 and a front plate 462. The front base 460 is adapted to receive the front seal 50 which is held between the front plate 462 and the front base 460. In one embodiment, the front seal 50 has a height and width slightly larger than the front base 460 so that a portion of the front seal 50 extends beyond the front base 460 and is exposed for engagement with the sleeve 16, 216. In one embodiment, the front base 460 includes a front bracket 464 which is adapted to receive the front seal 50 and retain the front seal 50 for engagement with the front interface 48. The front base 460 and front bracket 464 may be comprised of stainless steel and may be spot-welded together and spot-welded to the frame 412. The front seal 50 is configured to be stretched around or retained by the front bracket 464. In one embodiment, the front seal 50 has a rectangular or rounded rectangular hole 144 so that the front seal 50 may be placed over and rest on or around a corresponding front bracket 464. The front plate 462 may be comprised of PPS and may be affixed to the front base 460 by one or more screws which mate with one or more threaded cavities in the front bracket 464 or the front base 460.

In one embodiment, the rear wall 434 includes a rear base 480 and a rear plate 482. The rear base 480 includes a rear bracket 484 extending transversely from the rear base 480 and laterally across a portion of the rear base 480. The rear bracket 484 is adapted to receive the rear seal 52. The rear seal 52 may be placed over or stretched around the rear bracket 484. The rear bracket 484 also may include means for receiving and engaging the rear plate 482. The rear plate 482 may be affixed to the rear base 480 and rear bracket 484 to hold the rear seal 52. The rear plate 482 may be comprised of sheet metal and may be affixed to the rear base 480 through mechanical means, such as by a fastener, threaded fastener, machine screw or self-tapping screw. In another embodiment, the rear bracket 484 is formed from a section of the rear base 480 which extends outwardly transversely from the rear base 480. The rear seal 52 has a height and width the same size as or slightly smaller than the height and width of the rear base 480. The rear plate 482 has a height and width smaller than the height and width of the rear seal 52 so that a portion of the rear seal 52 is exposed for engagement with the sleeve 16, 216. In one embodiment, the rear seal 52 has a rectangular or rounded rectangular hole 152 so that the rear seal 52 may be stretched and placed over and rest on or around the rear bracket 484.

FIGS. 27 to 32 illustrate alternative embodiments of frames according to the present disclosure which may be engaged with the sleeves described herein to create a container for sterilization and storage. In one embodiment, the frame 1012 includes a front wall 1032 and rear wall 1034 which are joined by first and second side walls 1036, 1038.

Figure 27:
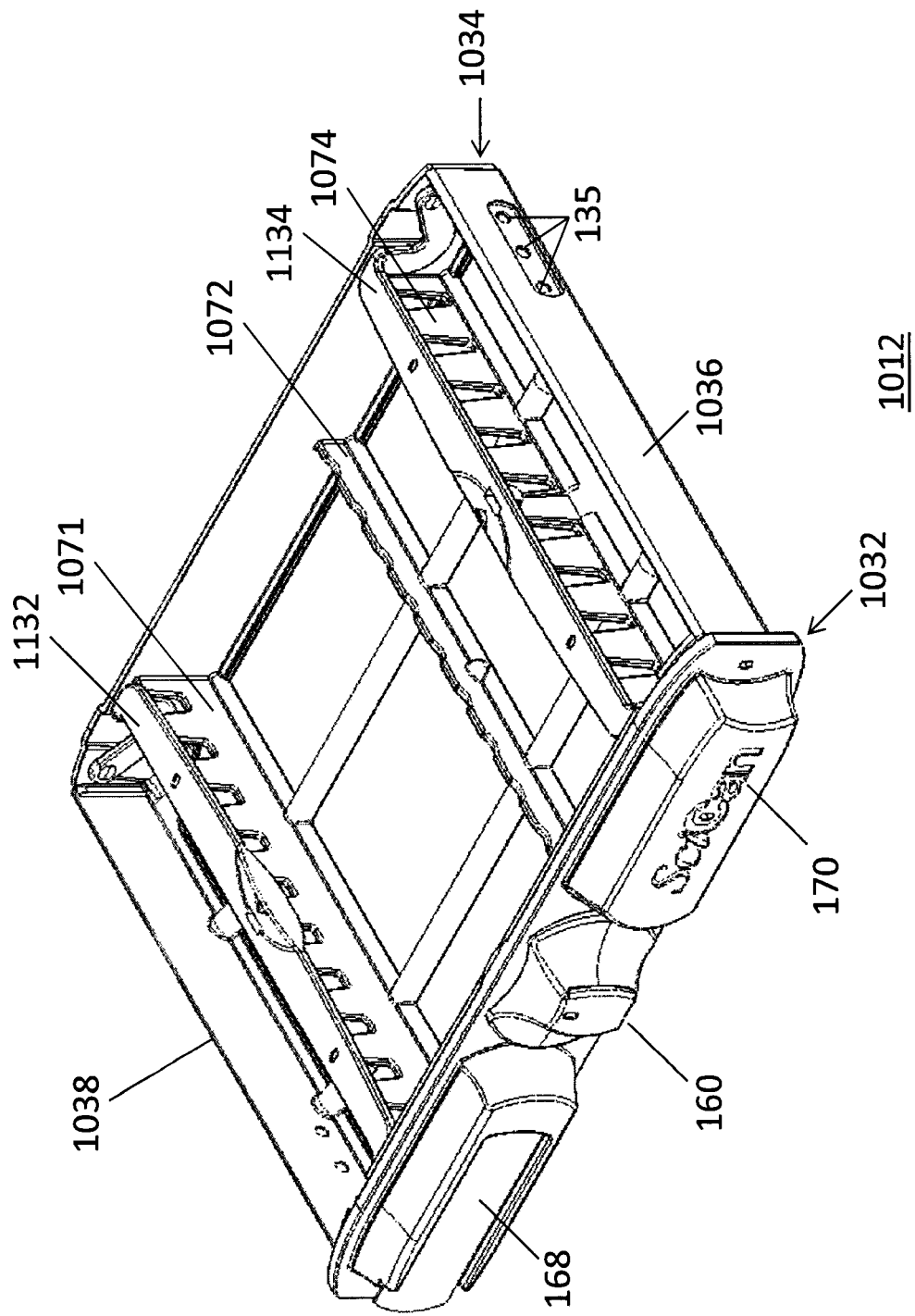
FIGS. 27(a) and (b) are front and rear isometric views of a frame in accordance with an embodiment of the present disclosure.
Figure 27B:
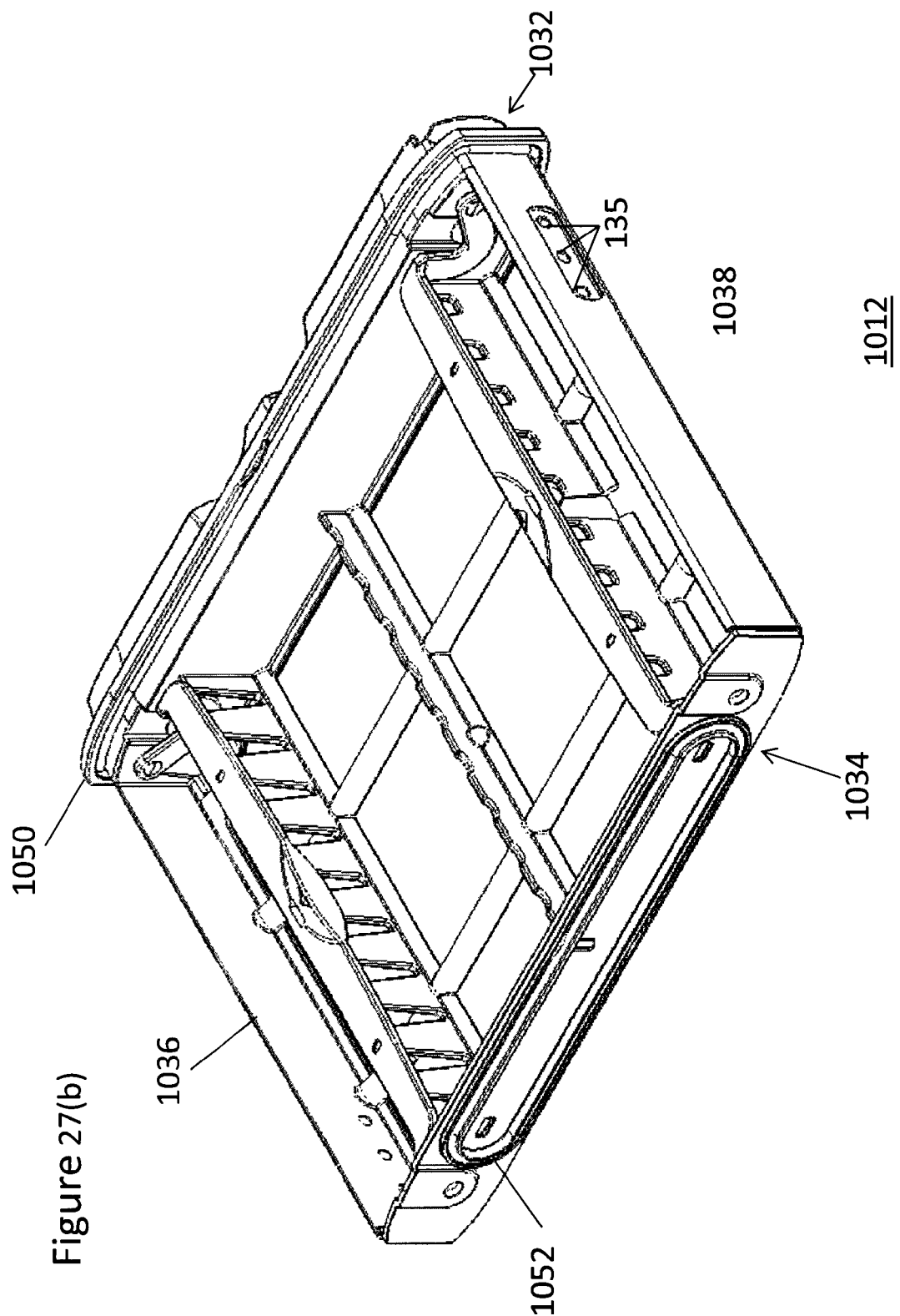
Figure 28:
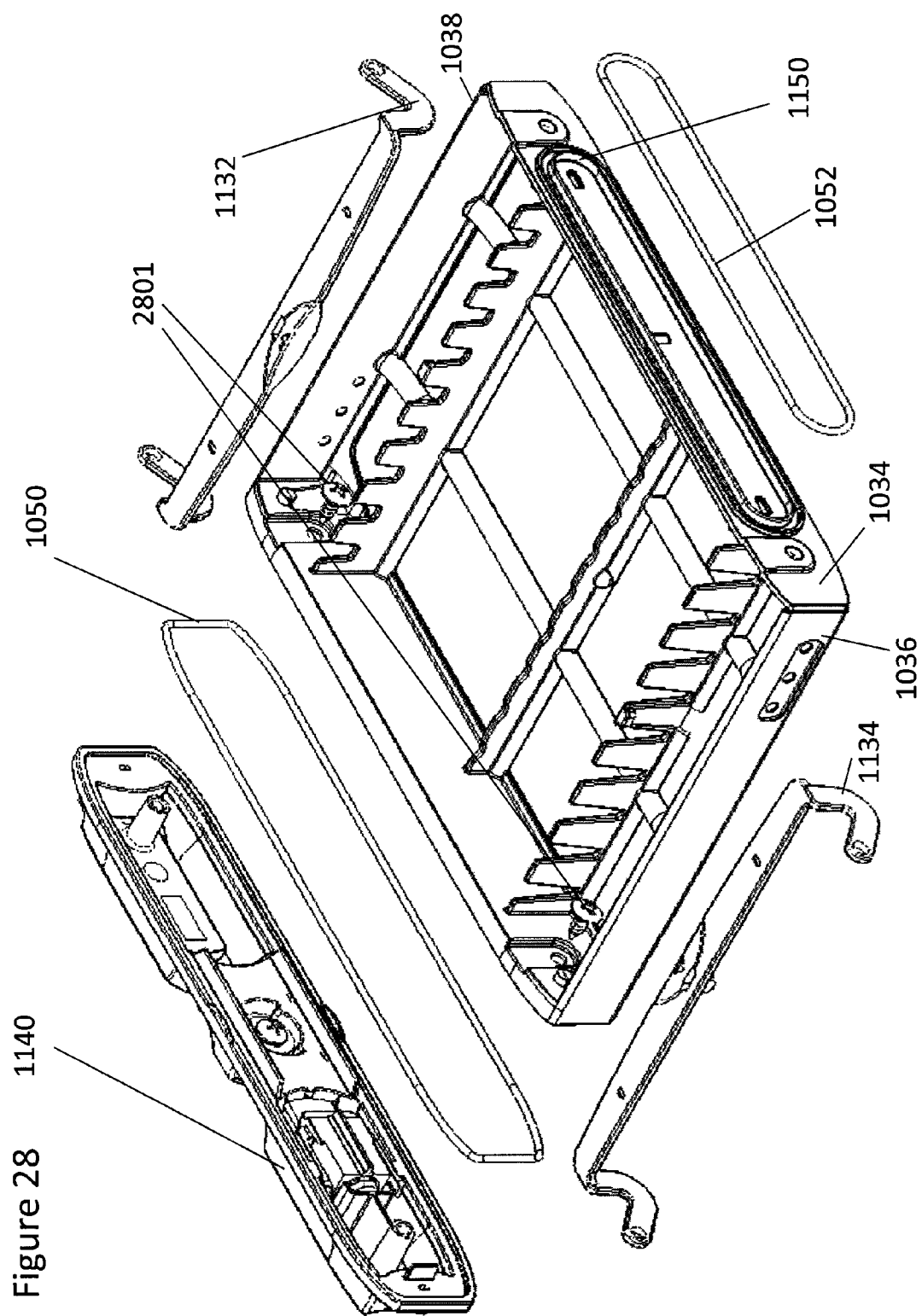
FIG. 28 is an exploded view of the frame of FIG. 27(b)
Figure 29:
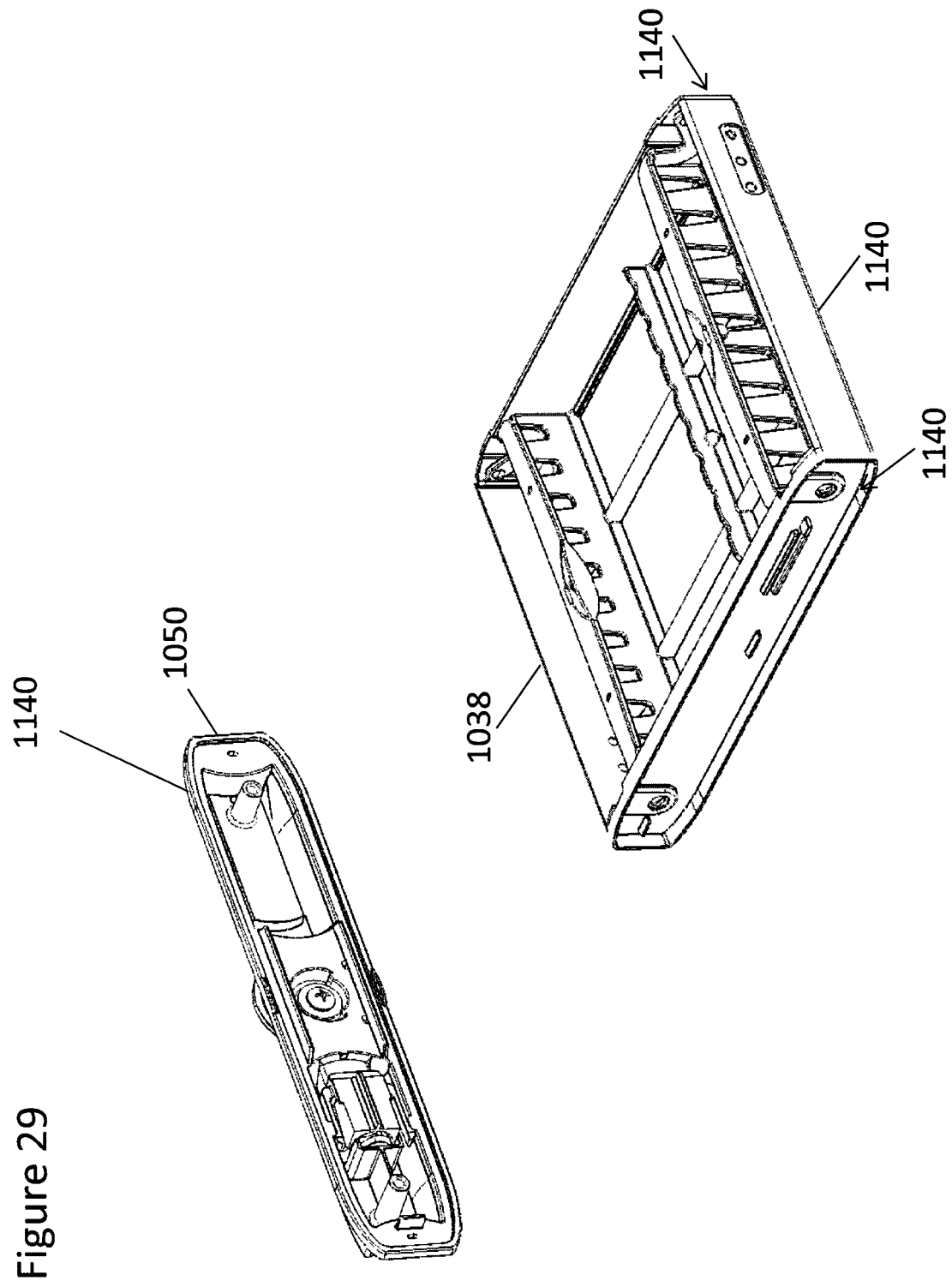
FIG. 29 is a view of the frame of FIG. 27(a) with the front wall disassembled.

The front wall 1032 includes a front base 1138 and a front plate 1140 as illustrated in FIGS. 28 and 29. In some embodiments, the front seal 1050 is comprised of an o-ring in silicone material. The front seal 1050 is held within a channel in the front plate 1140. When the front plate 1140 is mounted to the front base 1138, at least a portion of the front seal 50 is exposed around the circumference of the front wall 1032 as shown in FIG. 27(b), for engagement with the sleeve 16, 1016, as described above. In some embodiments, the front plate 1140 is affixed to the front base 1138 by mechanical means such as by a fastener, threaded fastener, machine screw or self-tapping screws 2801 as shown in FIG. 28.

Figure 30:
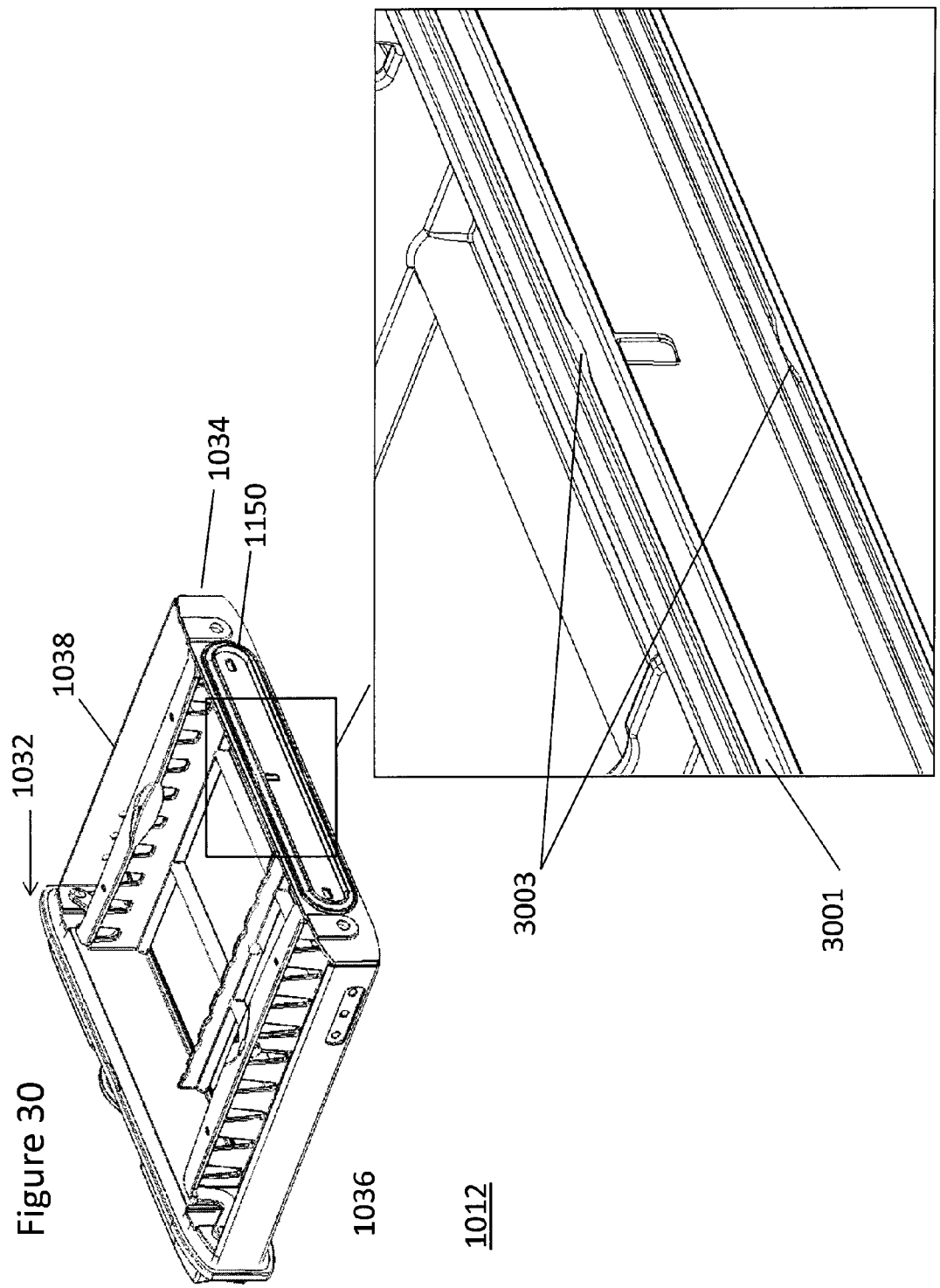
FIG. 30 is a view of the frame of FIG. 27(b) with an enlarged view of a portion of the rear wall of the frame.

In one embodiment as illustrated in FIGS. 27(b), 28 and 30, the rear wall 1034 includes a rear bracket 1150 which is adapted to receive the rear seal 1052. In some embodiments, the rear seal 1052 comprises an o-ring in silicone material. The rear seal may be placed over the bracket 1150 and exposed when the frame 1012 and rear interface 46 of the sleeve 16, 1016 are engaged, as described above. In some embodiments, the rear bracket 1150 includes a channel 3001 for receiving the rear seal 1052. Various means may be provided to retain the rear seal 52 in the channel 3001 and to prevent the rear seal 1052 from becoming dislodged before the frame 1012 and sleeve 16, 1016 are engaged, such as by indenting or angling one or more portions of the rear bracket 1150 inwardly towards the rear seal 1052. In one embodiment, as shown in FIG. 30, the rear bracket 1150 and channel 3001 may include one or more small protrusions 3003 wherein the walls of the channel 3001 are indented slightly towards the rear seal 1052. The width of the channel 3001 is effectively reduced at one or more points to hold the rear seal 1052 in place.

In some embodiments, the front and rear seals 1050, 1052 may be provided on the respective front and rear interfaces, 48, 46 of the sleeve 16, 1016. Providing the front and rear seals 1050, 1052 on the frame 12, 1012 allows for easier access to the seals for inspection and cleaning.

Figure 31:
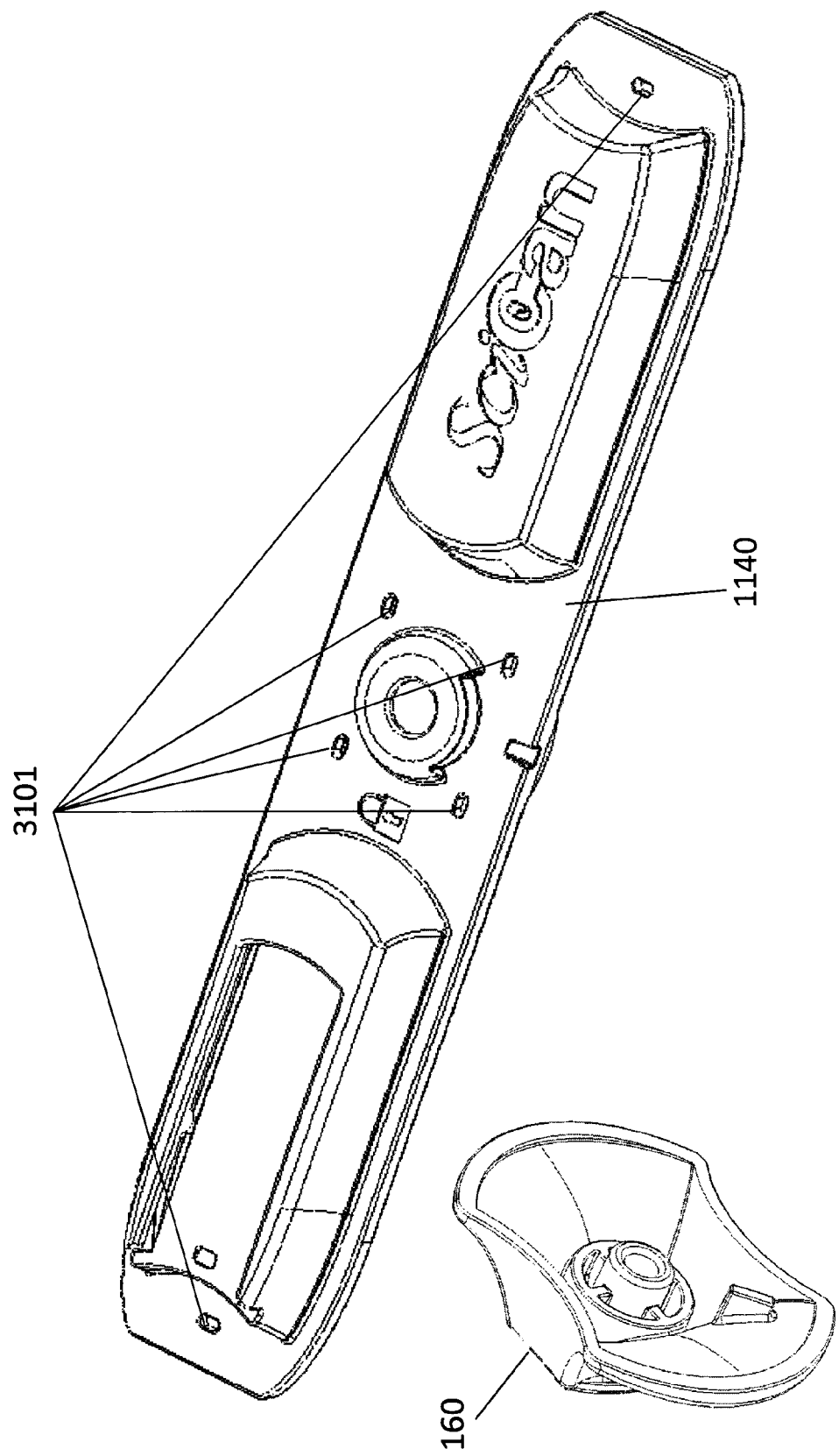
FIG. 31 is a top view of a portion of the front wall of a frame.
Figure 32:
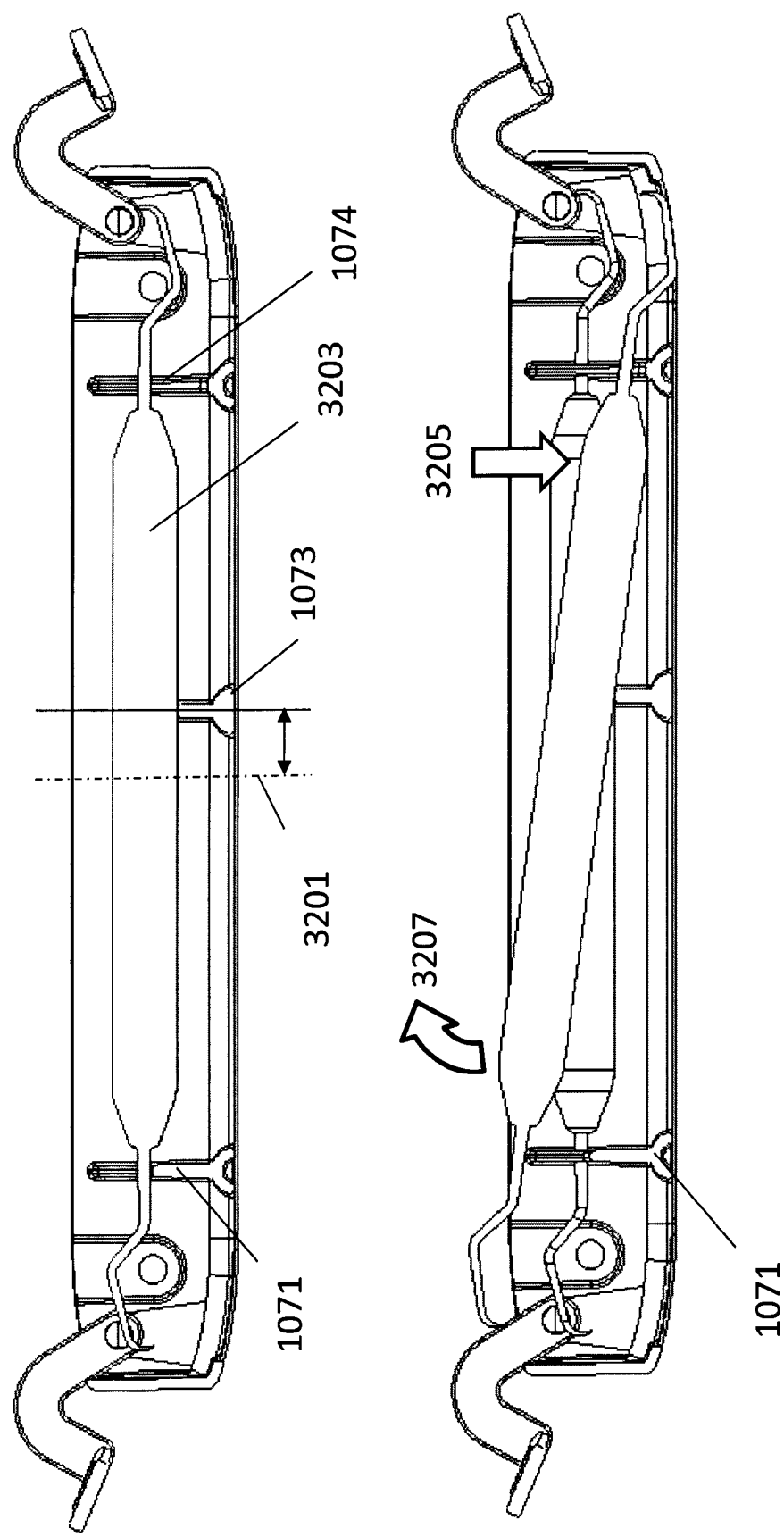
FIG. 32 is a side view of the frame of FIGS. 27(a) and (b), showing instruments loaded in the frame.

FIG. 31 illustrates a top view of the front plate 1140 according to an embodiment of the present disclosure. The front plate 1140 includes one or more condensate drains 3101 to assist with draining condensate from the container 10, 1000, including condensate from the front wall 1032. The drains 3101 may be provided at numerous locations on the front plate 1140 as shown in order to facilitate the draining of condensate in any orientation of the container 10, 1000 as illustrated in FIGS. 2(a) to (h).

In one embodiment, the frame 1012 includes one or more supports, such as a first support 1071 and a second support 1073 to receive articles for sterilization. One or more spacers 1074 may be provided to maintain space between the instruments to allow for the passage of water, steam and air around the instruments during the washing and sterilization processes. Handles 1132, 1134 may be provided and may be pivotally attached to the front and rear walls 1032, 1034. The handles 1132, 1134 may rest on or adjacent the one or more supports 1071, 1073 or spacers 1074. In one embodiment, as illustrated in at least FIGS. 27(a) and 32, the second support 1073 is positioned in the frame 1012 behind the center line 3201 of the frame 1012. The instrument 3203 rests on the supports in a stable fashion since the second support 1073 is positioned behind the center of gravity of the instrument. When a user depresses one end of the instrument 3203, shown by the arrow 3205 in FIG. 32, the second support 1073 acts as a pivot and the instrument 3203 is raised above the first support 1071 and above the frame 1012. The user may then pick up the instrument 3203 by the raised portion of the instrument handle. While the second support 1073 does not function to retain the instruments within the frame 1012, it improves the ability of a user to retrieve an instrument from among instruments which may be densely packed in the frame 1012. It will be appreciated that in some embodiments, the second support 1073 may be positioned differently with respect to the center line 3201 depending on the instruments to be support by the frame 1012.

Figure 33:
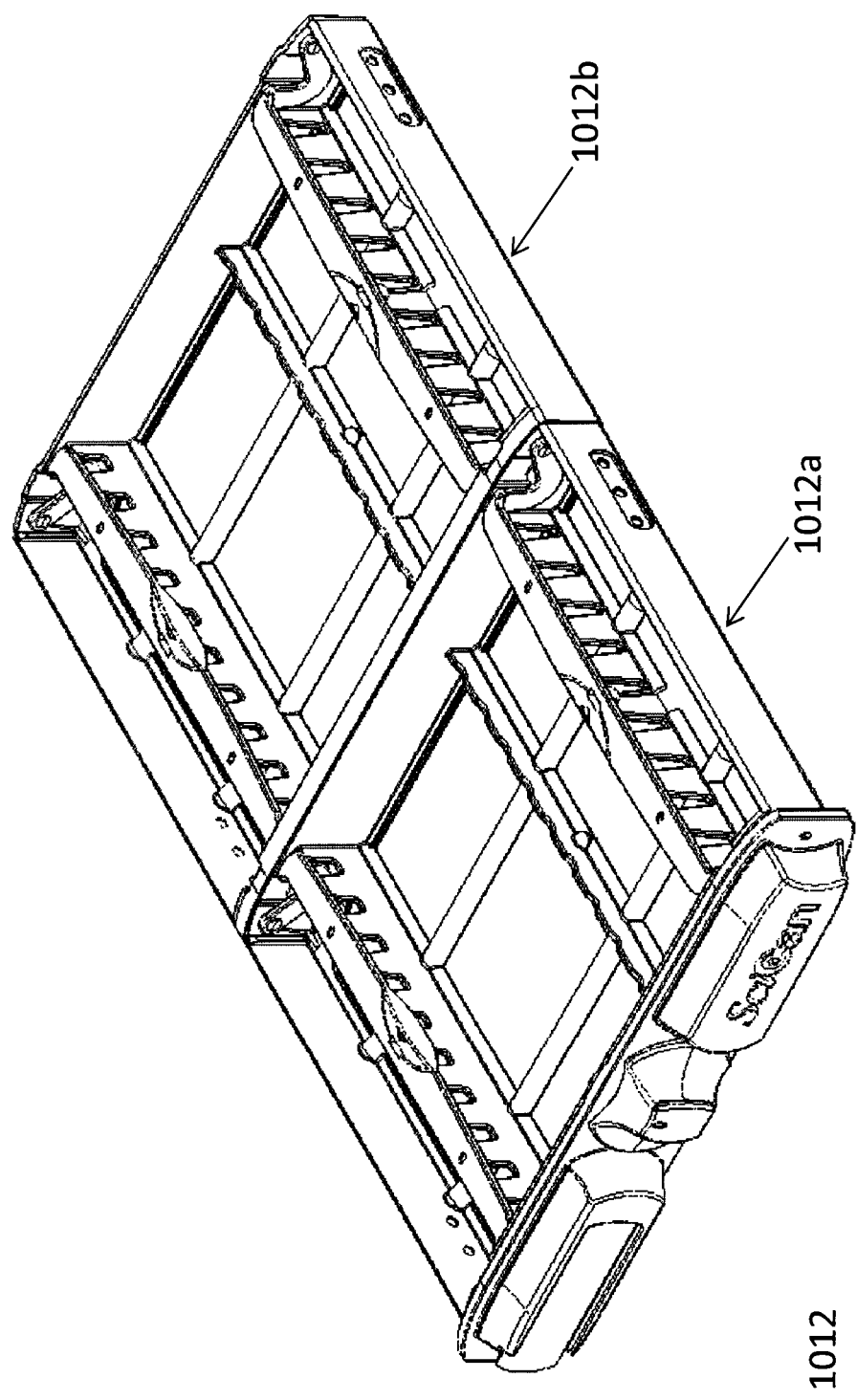
FIG. 33 is a front isometric view of a frame in accordance with an embodiment of the present disclosure.

In another embodiment, the frame 1012 may be comprised of multiple existing frames which are modified and joined together, as illustrated in FIG. 33. In this embodiment, the rear wall 1034 of the one frame 1012a may be mechanically fixed to the front base 1138 of a second frame 1012b. A front plate 1140 and front seal 1050 are provided for the first frame 1012a and a rear bracket 1150 and rear seal 1052 are provided for the second frame 1012b, as described above. It will be appreciated that frames 1012 of various dimensions may be provided and two or more frames may be fixed together with a front plate 1140 and front seal 1050 provided for the first frame and a rear bracket 1150 and rear seal 1052 are provided for the last frame. For example, three smaller sized frames may be combined and inserted into a larger sized sleeve to create the sterilization container. Alternatively, two medium sized frames may be combined and inserted into a larger sized sleeve to create the sterilization container. Thus, flexibility is provided in the configuration of the frame, and contents which may be placed in the frame and container for sterilization. In some embodiments, one or more frames may be adapted to support a basket, such as but not limited to basket 320 as described above. The frame 1012 may also receive other cassettes containing instruments and articles for sterilization. Thus, the frame 1012 may support a combination of one or more supports, racks, baskets, and/or cassettes for receiving instruments prior to the frame being engaged with a sleeve 16, 1016.

It will be appreciated that various configurations of containers for washing, sterilization, transportation and sterile storage of articles may be provided by combining the various sleeves 16, 216, 1016 and frames 12, 212, 312, 412, 1012 and that portions of the sleeves 16, 216, 1016 and frames 12, 212, 312, 412, 1012 may be comprised of metal, plastic and glass materials as described herein.

Thus, it is apparent that there has been provided in accordance with the invention a container for washing, sterilization, transportation and sterile storage of articles that fully satisfy the objects, aims and advantages set forth above. While the invention has been described in conjunction with illustrated embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the invention.

What is claimed is:

1. A reusable container for washing, sterilization, transportation and sterile storage of articles, the reusable container comprising:
    a frame adapted to receive articles for sterilization, the frame having at least a front wall and a rear wall;
    a sleeve having a top panel, a bottom panel, first and second side panels, and a front interface and a rear interface, the top panel, bottom panel and two side panels defining a front open end and a rear open end and defining a cavity for receiving the frame into the sleeve, when the frame is received into the cavity through the front open end the front interface mates with the front wall of the frame and the rear interface mates with the rear wall of the frame to effectively close the front and rear open ends, thereby creating sterile barriers at respective front and rear engagements, and thereby defining a sterilization chamber; and
    at least one opening to permit microorganism-free communication between a sterilization apparatus and the sterilization chamber.

2. The reusable container according to claim 1 wherein the sleeve further comprises:
    a first region, a second region disposed discretely from said first region, and a third region disposed discretely from said second region;
    the front interface is between the first and second regions; and
    the rear interface is between the second and third regions.

3. The reusable container according to claim 2 wherein the front wall and rear wall of the frame sealably mate with the respective front and rear interfaces of the sleeve to create the front and rear engagements and to define the sterilization chamber.

4. The reusable container according to claim 3 further comprising a front seal between the front wall and the front interface and a rear seal between the rear wall and the rear interface.

5. The reusable container according to claim 2 wherein the top panel and bottom panel in the first region are separated by a distance greater than a distance between the top panel and bottom panel in the second region, and the first and second side panels in the first region are separated by a distance greater than a distance between the first and second side panels in the second region.

6. The reusable container according to claim 2 wherein the front interface comprises a portion of the top panel, bottom panel and first and second side panels between the first region and the second region.

7. The reusable container according to claim 6 wherein the front interface has a stepped longitudinal cross-section.

8. The reusable container according to claim 2 wherein the top panel and bottom panel in the third region are separated by a distance greater than a distance between the top panel and bottom panel in the second region, and the first and second side panels in the third region are separated by a distance greater than a distance between the first and second side panels in the second region.

9. The reusable container according to claim 2 wherein the rear interface comprises portions of the top panel, the bottom panel, the first side panel, the second side panel, or combinations thereof, extending inwardly towards the cavity between the second and third regions.

10. The reusable container according to claim 2 wherein a first surface of the front interface faces the first region and wherein the front wall sealably engages the first surface of the front interface.

11. The reusable container according to claim 2 wherein the rear interface comprises a rib extending angularly from the rear interface towards the second region of the sleeve and wherein the rear wall sealably engages the rib.

12. The reusable container according to claim 2 wherein, the front wall of the frame includes a knob for securing the frame and the sleeve, the knob including at least one tab extending in a plane parallel to the front wall, and wherein the sleeve further comprises at least one slot in at least one of the top panel or bottom panel within the first region or third region, the at least one slot adapted to receive a portion of the at least one tab.

13. The reusable container according to claim 2 wherein the sleeve slidably engages the frame.

14. The reusable container according to claim 13 wherein the rear wall of the frame first sealably engages the rear interface of the sleeve and the front wall of the frame then engages the front interface of the sleeve as the frame is slid into the sleeve.

15. The reusable container according to claim 13 wherein the front wall of the frame first sealably engages the front interface of the sleeve and the rear wall of the frame then engages the rear interface of the sleeve as the frame is slid into the sleeve.

16. The reusable container according to claim 1 wherein the front and rear engagements comprise sealed engagements.

17. The reusable container according to claim 1 wherein each of the front and rear engagements defines one or more tortuous paths.

18. The reusable container according to claim 1 wherein the at least one opening defines a tortuous path between the sterilization apparatus and the sterilization chamber.

19. The reusable container according to claim 1 further comprising at least one filter assembly adjacent to the at least one opening.

20. The reusable container according to claim 1 wherein the sleeve comprises a plurality of openings in the top panel, or in the bottom panel, or in both the top and bottom panels, the plurality of openings permitting communication between the sterilization apparatus and the sterilization chamber.

21. The reusable container according to claim 20 wherein the plurality of openings in the top panel, or in the bottom panel, or in both the top and bottom panels define one or more tortuous paths between the sterilization apparatus and the sterilization chamber.

22. The reusable container according to claim 20 wherein the sleeve further comprises one or more filter assemblies adjacent to the plurality of openings in the top panel, or in the bottom panel, or in both the top and bottom panels.

23. The reusable container according to claim 1 wherein the sleeve is comprised of transparent material, or semi-transparent material, or metal, or a combination of transparent material or semi-transparent material, and metal.

24. The reusable container according to claim 1 wherein the top panel, the bottom panel, the first side panel and the second side panel form the sleeve in a one piece construction.

25. The reusable container according to claim 1 wherein in a first configuration, the frame is positioned in the cavity of the sleeve and wherein in a second configuration, the frame is partially nested atop one of the top panel or bottom panel of the sleeve.

26. The reusable container according to claim 25 wherein at least one of the top panel or bottom panel comprises means for retaining the frame in the second configuration.

27. The reusable container according to claim 1 wherein the reusable container further comprises a holder in the sterilization chamber for an indicator, the indicator being visible through a portion of the sleeve to provide a visible change in state in response to a sterilization process.

28. A method for washing and sterilization of articles comprising:
   placing articles in a frame, the frame being adapted to receive articles for sterilization, the frame having at least a front wall and a rear wall;
   washing the frame and articles placed therein in a washing apparatus;
   inserting the washed frame and articles into a sleeve to form a reusable container, the sleeve having a top panel, a bottom panel, first and second side panels, and a front interface and a rear interface, the top panel, bottom panel and two side panels defining a front open end and a rear open end and defining a cavity for receiving the frame into the sleeve, when the frame is received into the cavity through the front open end the front interface mates with the front wall of the frame and the rear interface mates with the rear wall of the frame to effectively close the front and rear open ends thereby creating sterile barriers at respective front and rear engagements, and thereby defining a sterilization chamber, the reusable container having at least one opening to permit microorganism-free communication between a sterilization apparatus and the sterilization chamber; and
   sterilizing the reusable container and articles contained therein in a sterilization apparatus.

29. The method according to claim 28, further comprising storing the reusable container and articles contained therein.

30. The method according to claim 28 wherein the front and rear engagements comprise sealing engagements, one or more tortuous paths, or a combination of sealing engagements and one or more tortuous paths.

31. The method according to claim 30 wherein,
   the at least one opening comprises a plurality of openings in the top panel, or in the bottom panel, or in both the top and bottom panels; and wherein,
   the reusable container comprises one or more filter assemblies adjacent to the plurality of openings in the top panel, or in the bottom panel, or in both the top and bottom panels.

* * * * *